US011963977B2

(12) United States Patent
Vacanti et al.

(10) Patent No.: US 11,963,977 B2
(45) Date of Patent: Apr. 23, 2024

(54) GENERATING PLURIPOTENT CELLS DE NOVO

(71) Applicant: VCell Therapeutics, Inc., Hanover, MD (US)

(72) Inventors: Charles A. Vacanti, Uxbridge, MA (US); Martin P. Vacanti, Manhattan, KS (US); Koji Kojima, Brookline, MA (US)

(73) Assignee: VCell Therapeutics Inc., Hanover, MD (US)

( * ) Notice: Subject to any disclaimer, the term of this patent is extended or adjusted under 35 U.S.C. 154(b) by 0 days.

(21) Appl. No.: 14/397,080

(22) PCT Filed: Apr. 24, 2013

(86) PCT No.: PCT/US2013/037996
§ 371 (c)(1),
(2) Date: Oct. 24, 2014

(87) PCT Pub. No.: WO2013/163296
PCT Pub. Date: Oct. 31, 2013

(65) Prior Publication Data
US 2015/0110749 A1 Apr. 23, 2015

Related U.S. Application Data

(60) Provisional application No. 61/779,533, filed on Mar. 13, 2013, provisional application No. 61/637,631, filed on Apr. 24, 2012.

(51) Int. Cl.
C12N 5/074 (2010.01)
A61K 35/12 (2015.01)

(52) U.S. Cl.
CPC ............ *A61K 35/12* (2013.01); *C12N 5/0607* (2013.01); *C12N 5/0696* (2013.01);
(Continued)

(58) Field of Classification Search
None
See application file for complete search history.

(56) References Cited

U.S. PATENT DOCUMENTS 5,753,431 A * 5/1998 Chiang ................. C07K 14/47
435/6.16
6,090,625 A 7/2000 Abuljadayel
(Continued)

FOREIGN PATENT DOCUMENTS

KR 20100075771 7/2010
RU 2215539 C2 11/2003
(Continued)

OTHER PUBLICATIONS

Bayart E & Cohen-Haguenauer O. 2013. Technological overview of iPS induction form human adult somatic cells. Curr Gene Therap 13: 73-92.*
(Continued)

*Primary Examiner* — Sharmila G Landau
*Assistant Examiner* — Stephanie A McNeil
(74) *Attorney, Agent, or Firm* — PABST PATENT GROUP LLP

(57) ABSTRACT

The technology described herein relates to methods, assays, and compositions relating to causing a cell to assume a more pluripotent state, e.g. without introducing foreign genetic material.

12 Claims, 17 Drawing Sheets
Specification includes a Sequence Listing.

(52) U.S. Cl.
CPC ...... *C12N 2500/02* (2013.01); *C12N 2506/11* (2013.01); *C12N 2521/00* (2013.01); *C12N 2523/00* (2013.01)

(56) References Cited

U.S. PATENT DOCUMENTS

| | | | |
|---|---|---|---|
| 6,294,174 | B1 | 9/2001 | Krsmanovic et al. |
| 7,575,321 | B2 | 8/2009 | Vacanti et al. |
| 2002/0076812 | A1 | 6/2002 | Abuljadayel |
| 2002/0151050 | A1 | 10/2002 | Vacanti et al. |
| 2005/0118561 | A1* | 6/2005 | Kopyov ............... C12N 5/0623 435/1.1 |
| 2006/0084167 | A1 | 4/2006 | Cohenford et al. |
| 2006/0252062 | A1* | 11/2006 | Zaccouto ............ A61L 27/3895 435/325 |
| 2007/0190646 | A1 | 8/2007 | Engler et al. |
| 2008/0242594 | A1* | 10/2008 | McKay ............... C07K 14/4705 514/1.1 |
| 2009/0047263 | A1* | 2/2009 | Yamanaka ......... C07K 14/4702 424/93.21 |
| 2009/0104158 | A1* | 4/2009 | Young ................. C12N 5/0607 424/93.7 |
| 2009/0136947 | A1* | 5/2009 | Tovey ................ G01N 33/5041 435/6.14 |
| 2009/0280518 | A1* | 11/2009 | Adamo ............ G01N 33/48728 435/29 |
| 2009/0298095 | A1* | 12/2009 | Hoke ................... C12N 9/1276 435/7.21 |
| 2011/0070647 | A1 | 3/2011 | Dezawa et al. |
| 2011/0076678 | A1 | 3/2011 | Jaenisch et al. |
| 2011/0143431 | A1 | 6/2011 | Abuljadayel |
| 2012/0003186 | A1 | 1/2012 | Kang |
| 2013/0164731 | A1 | 6/2013 | Cimino et al. |

FOREIGN PATENT DOCUMENTS

| | | | |
|---|---|---|---|
| WO | 02097065 | A2 | 12/2002 |
| WO | 2007047766 | A2 | 4/2007 |
| WO | 2008038148 | A2 | 4/2008 |
| WO | 2008066630 | A2 | 6/2008 |
| WO | 2009057831 | A1 | 5/2009 |
| WO | 2011007900 | A1 | 1/2011 |
| WO | 2011125948 | A1 | 10/2011 |

OTHER PUBLICATIONS

"This Week: STAP retracted." 2014. Nature 511: 5-6.*
Vogel G. 2015. "Sleuthing sheds light on STAP cell fiasco." Available online at <http://www.sciencemag.org/news/2015/09/sleuthing-sheds-light-stap-cell-fiasco>.*
Cyranoski D. 2014. Cell-Induced stress. Nature 511: 140-43.*
Cyranoski D. 2015. Collateral damage. Nature 520: 600-03.*
Vacanti C & Kojima K. 2014. Revised STAP cell protocol. Available online at <https://web.archive.org/web/20140912140636/https://research.bwhanesthesia.org/site_assets/51520d191eea6679ce000001/cterm/Revised_STAP_protocol-28bcd7e61d02a23624eb590717e241fe.pdf>. 4 pages.*
Ludwig T et al. 2006. Derivation of human embryonic stem cells in defined conditions. Nat Biotechnol 24: 185-87 plus supplementary figure 1.*
Zhao et al., A Prominent Low-pH Methotrexate Transport Activity in Human Solid Tumors: Contribution to the Preservation of Methotrexate Pharmacologic Activity in Hela Cells Lacking the Reduced Folate Carrier, 2004, Clinical Cancer Research, 10: 718-727 (Year: 2004).*
Tai et al., Oct4 expression in adult human stem cells: evidence in support of the stem cell theory of carcinogenesis, 2005, Carcinogenesis, 26(2):495-502 (Year: 2005).*
Rosenberg et al., Immunization of Cancer Patients Using Autologous Cancer Cells Modified by Insertion of the Gene for Tumor Necrosis Factor, 1992, Human Gene Therapy, 3: 57-73 (Year: 1992).*
Ogawa et al, A novel mechanism for regulating clonal propagation of mouse ES cells, 2004, Genes to Cells, 9:471-477 (Year: 2004).*
Sell et al., Stem cell origin of cancer and differentiation therapy, 2004, Critical Reviews in Oncology/Hematology, 51: 1-28 (Year: 2004).*
Vogel, 2015, "Sleuthing sheds light on STAP cell fiasco," Science, 349(6255):1430-31 (Year: 2015).*
Niwa, 2016, "Investigation of the cellular reprogramming phenomenon referred to as stimulus-triggered acquisition of pluripotency (STAP)" Scientific Reports, 6: 28003 (Year: 2016).*
Bilbao et al, ATP stimulates the proliferation of MCF-7 cells through the PI3K/Aktsignaling pathway, 2010, Archives of Biochemistry and Biophysics 499: 40-48 (Year: 2010).*
Yao et al, 2012, ATP conditions intestinal epithelial cells to an inflammatory state that promotes components of DC maturation, Eur. J. Immunol., 42: 3310-3321 (Year: 2012).*
Takenouchi et al, The activation of P2X7 receptor induces cathepsin D-dependent production of a 20-kDa form of IL-1β under acidic extracellular pH in LPS-primed microglial cells, 2011, Journal of Neurochemistry, 117: 712-723 (Year: 2011).*
Rafiee et al., Human esophageal microvascular endothelial cells respond to acidic pH stress by PI3K/AKT and p38 MAPK-regulated induction of Hsp70 and Hsp27, 2006, Am J Physiol Cell Physiol 291: C931-C945 (Year: 2006).*
Christoforou et al, A draft map of the mouse pluripotent stem cell spatial proteome, 2016, Nature Communications 7:8992 (Year: 2016).*
Christoforou et al, A draft map of the mouse pluripotent stem cell spatial proteome, 2016, Nature Communications 7:8992 Supplementary Data Set 1 (Year: 2016).*
Noguchi, ROS-dependent Activation of ASK1 in Inflammatory Signaling, 2008, J. Oral Biosci. 50(2) : 107-114 (Year: 2008).*
Yazd et al, OCT4B1, a novel spliced variant of OCT4, generates a stable truncated protein with a potential role in stress response, 2011, Cancer Letters, 309(2): 170-175 (Year: 2011).*
Wang et al, Alternative Translation of OCT4 by an Internal Ribosome Entry Site and its Novel Function in Stress Response, 2009, Stem Cells, 27:1265-1275 (Year: 2009).*
Cruz et al, ATP Activates a Reactive Oxygen Species-dependent Oxidative Stress Response and Secretion of Proinflammatory Cytokines in Macrophages, 2007, J. Bio. Chem., 282(5): 2871-2879 (Year: 2007).*
Monastyrskaya Cell. Mol. Life Sci. The annexins: spatial and temporal coordination of signaling events during cellular stress, (2009) 66:2623-2642 (Year: 2009).*
Obokata et al: "Bidirectional developmental potential in reprogrammed cells with acquired pluripotency", Nature, vol. 505, No. 7485, pp. 676-680 (2014).
Obokata et al: "Stimulus-triggered fate conversion of somatic cells into pluripotency", Nature, vol. 505, No. 7485, pp. 641-647 (2014).
Obokata et al: "Retraction: Bidirectional developmental potential in reprogrammed cells with acquired pluripotency", Nature, vol. 511, No. 7507, p. 112 (2014).
Ogawa et al: "A novel mechanism for regulating clonal propogation of mouse ES cells", Genes To Cells, vol. 9, No. 5, pp. 471-477 (2004).
Lengerke and Daley: "Autologous blood cell therapies from pluripotent stem cells", Blood Reviews, vol. 24, No. 1, pp. 27-37 (2009).
New Zealand First Examination Report from Appl. No. NZ 702229 dated May 3, 2016.
Barth, "Neural differentiation without organizer", Journal of Experimental Zoology 87(3):371-383 (1941).
Holtfreter, "Neural induction in explants which have passed through a sublethal cytolysis", Journal of Experimental Zoology 106(2): 197-222 (1947).
Reynolds et al., "Generation of neurons and astrocytes from isolated cells of the adult mammalian central nervous system." Science 255, 1707-1710 (1992).
Megeney et al., "MyoD is required for myogenic stem cell function in adult skeletal muscle." Genes Dev. 10:1173-1183 (1996).
Caplan, "Mesenchymal stem cells." Journal of orthopaedic research: official publication of the Orthopaedic Research Society 9:641-650 (1991).

(56) References Cited

OTHER PUBLICATIONS

Lavker et al., "Epidermal stem cells." The Journal of investigative dermatology 81(1 suppl):121s-127s (1983).
Lengner et al., "The pluripotency regulator Oct4: a role in somatic stem cells?" Cell Cycle 7:725-728 (2008).
Berg et al., "An argument against a role for Oct4 in somatic stem cells." Cell stein cell 1:359-360 (2007).
Jiang et al. Pluripotency of mesenchymal stem cells derived from adult marrow. Nature 418:41-49 (2002).
D'Ippolito et al. "Marrow-isolated adult multilineage inducible (MIAMI) cells, a unique population of postnatal young and old human cells with extensive expansion and differentiation potential." Journal of cell science 117:2971-2981 (2004).
Johnson et al. "Oocyte generation in adult mammalian ovaries by putative germ cells in bone marrow and peripheral blood." Cell 122:303-315 (2005).
Kucia et al. "A population of very small embryonic-like (VSEL) CXCR4(+)SSEA-1(+)Oct-4+ stem cells identified in adult bone marrow." Leukemia 20:857-869 (2006).
Kuroda et al. "Unique multipotent cells in adult human mesenchymal cell populations." PNAS 107:8639-8643 (2010).
Obokata et al. "The potential of stem cells in adult tissues representative of the three germ layers." Tissue engineering Part A 17(5-6):607-615 (2011).
Rahnemai-Azar et al. "Human marrow-isolated adult multilineage-inducible (MIAMI) cells protect against peripheral vascular ischemia in a mouse model." Cytotherapy 13(2):179-192 (2011).
Huang et al."Bone marrow transplantation temporarily improves pancreatic function in streptozotocin-induced diabetes: potential involvement of very small embryonic-like cells." Transplantation 89(6):677-685 (2010).
Zuba-Surma et al. "Transplantation of expanded bone marrow-derived very small embryonic-like stem cells (VSEL-SCs) improves left ventricular function and remodelling after myocardial infarction." J Cell Mol Med. 15:1319-1328 (2011).
Paczkowska et al. "Aldehyde dehydrogenase (ALDH)—a promising new candidate for use in preclinical and clinical selection of pluripotent very small embryonic-like stem cells (VSEL SCs) of high long-term repopulating hematopoietic potential." Annals of transplantation: quarterly of the Polish Transplantation Society 16:59-71 (2011).
D'Ippolito et al., "Isolation and characterization of marrow-isolated adult multilineage inducible (MIAMI) cells." Experimental hematology 34:1608-1610 (2006).
Hitoshi Niwa, "Investigation of the cellular reporgramming phenomenon referred to as stimulus-triggered acquisition of pluripotency (STAP)", Scientific Reports, vol. 6, No. 28003, pp. 1-10, Jun. 13, 2016.
New Zealand Further Examination Report from Appl. No. NZ 702229 dated Dec. 22, 2016.
JP Office Action issued in corresponding Application No. 509109/2015 dated Mar. 7, 2017, 14 pages.
Hitoshi Niwa, "Investigation of the Cellular Reprogramming Phenomenon Referred to as Stimulus-Triggered Acquisition of Pluripotency (STAP)", Sci Rep., Jun. 13, 2016, vol. 6, Article No. 28003.
Written Opinion issued in corresponding Application No. 11201407768Q dated Feb. 28, 2017, 8 pages.

Australian Examination Report issued in corresponding Appl. No. 2013251649 dated Mar. 23, 2018 (5 pages).
Office Action and Search Report issued in corresponding RU Application No. 2014147093 dated Mar. 6, 2017.
Decision of Refusal issued in Japanese Appl. No. 509109/2015 dated Feb. 20, 2018 together with English Translation (13 pages).
Further Examination Report issued in New Zealand Appl. No. 727170 dated Feb. 23, 2018 (9 pages).
Office Action issued in corresponding Russian Appl. No .: 2014147093 dated May 10, 2018, together with English translation (6 pages).
Russian Office Action issued in corresponding application, RU 2014147093, dated Nov. 17, 2017, together with English translation (6 pages).
European Examination Report issued in Appl. No. EP 13 780 959.6 dated Mar. 20, 2018 (8 pages).
Examination Report No. 2 issued in corresponding Australian Appl. No. 2013251649 dated Feb. 27, 2019 (8 pages).
A.B. Hjelmeland, et al., "Acidic stress promotes a glioma stem cell phenotype", Cell Death and Differentiation, vol. 18, No. 5, pp. 829-840 (2011).
Boon Chin Heng, et al., "Induced pluripotent stem cells: a new tool for toxicology screening?", Arch Toxicol, vol. 33, No. 7, pp. 641-644 (2009).
Dong Li, et al., "Role of mechanical factors in fate decisions of stem cells", Regen. Med., vol. 2, No. 2, pp. 229-240 (2011).
Dekel Dado, et al., "Mechanical control of stem cell differentiation", Regenerative Medicine, vol. 7, No. 1, pp. 101-116 (2012).
European Search Report issued in corresponding Appl. No. EP 18 20 3532, date of completion Feb. 19, 2019 (6 pages).
Fourth Office Action issued in corresponding Chinese Appl. No. 201380033613.9 dated Jun. 21, 2018, together with English language translation (10 pages).
Fourth Examination Report issued in corresponding New Zealand Appl. No. 727170 dated Jul. 19, 2018 (6 pages).
Canadian Office Action issued in corresponding Appl. No. 2,885,576 dated Feb. 27, 2019 (6 pages).
David Cyranoski, "Gene tests suggest acid-bath stem cells never existed", Nature Breaking News, Jun. 17, 2014.
Tang, M. K. et al., Transient Acid Treatment Cannot Induce Neonatal Somatic Cells To Become Pluripotent Stem Cells. F1000Research, May 8, 2013, vol. 3, No. 102, pp. 1-11.
Report on STAP Cell Research Paper Investigation. Dec. 25, 2014.
Obokata, H. et al., Retraction: Stimulus-Triggered Fate Conversion Of Somatic Cells Into Pluripotency. Nature, Jul. 2, 2014, vol. 511, No. 7507, pp. 641-647.
Konno D. et al., STAP cells are derived from ES cells. Nature, Sep. 24, 2015, vol. 525, No. 7570, pp. E4-E5.
Angeles A. D. L. et al., Failure to replicate the STAP cell phenomenon. Nature, Sep. 24, 2015, vol. 525, No. 7570, pp. E6-E9.
First Written Opinion of the Intellectual Property Office of Singapore for Application No. 11201407768Q dated Aug. 14, 2015.
Second Written Opinion of the Intellectual Property Office of Singapore for Application No. 11201407768Q dated Apr. 27, 2016.
Indian Examination report issued in corresponding Appl. No. 8511/CHENP/2014 dated Mar. 19, 2019, with English language translation (9 pages).

\* cited by examiner

SEQUENCE LISTING

```
<160> NUMBER OF SEQ ID NOS: 90

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gttgttttgt tttggttttg gatat                                           25

<210> SEQ ID NO 2
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 2
atgggttgaa atattgggtt tattta                                         26

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ccaccctcta accttaacct ctaac                                          25

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gaggatgttt tttaagtttt tttt                                           24

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
aatgtttatg gtggattttg taggt                                          25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
cccacactca tatcaatata ataac                                          25

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtcatccttg atctgcccct                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
```

```
              primer

<400> SEQUENCE: 8
ggtacttacg atgcccagca                                                  20

<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccctgaatat ccctctgct                                                   19

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
agatggctac atctctcggt                                                  20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cactctggac ttggagatgc                                                  20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cttgtcgttg gtgatggtga                                                  20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gttgaagcag ttaatatggc                                                  20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 14
agatgagacc aacctggacc                                           20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
aggtggagat catcgccaac                                           20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cgttgaattt gccgtgagtg                                           20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
attgccaagt cgttctacga                                           20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aggtcgctta cagattgctg                                           20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gtctctttag aaaagtgtga                                           20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 20
tacagctttc ttcctggcca                                               20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atgtcagcct tgtggaaatt                                               20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtctgacaga ccaataccat                                               20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aacggctgcg tggtgaagcg                                               20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggacctccct tagagaggga                                               20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
acagtgcctt caggttagtc                                               20

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
```
gcatacaaag aagctgtgag                                               20

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tctttccacc aggcccccgg ct                                            22

<210> SEQ ID NO 28
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
tgtggggccc tgaaaggcga gctgagat                                      28

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gaagtctggt tccttggcag gatg                                          24

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
caggtgtttg agggtagctc                                               20

<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
actgcccctc atcagactgc tact                                          24

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
gttccaacct gtgcctcgcg tctt                                          24

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgtggtgagc atcttcggag tgg                                           23

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
acgagtggca gtttcttctt ggga                                          24

<210> SEQ ID NO 35
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atggacgcaa ctgtgaacat gatgttcgca                                    30

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgctgcggtc caggccatca agag                                          24

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
tagagctaga ctccgggcga tga                                           23

<210> SEQ ID NO 38
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gcgaactcac acaggcgaga aacc                                          24
```

```
<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
gctgtgtctc agggattgt                                                20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gagacgacct gctacacctg                                               20

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tccctacctg actgcttacg                                               20

<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
tatgtctgct cgtaccccctt                                              20

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
tcagacctcg gttcatcttc                                               20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cttggacctt cgaaggacga                                               20
```

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
tcaaagcgca gaccacctcg                                              20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gcatgtcgtc cgcagtaact                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tcgacttcgt cttgttcggt                                              20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
tctacctgtt ccgcgtctag                                              20

<210> SEQ ID NO 49
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
tggtgaaggt cggtgtgaac                                              20

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gtaggacaga aacggatgga                                              20

```
<210> SEQ ID NO 51
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtgtcgatcg ttcttcact                                                   19

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
attgcagctg caaatccctg                                                  20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tacgattcac ggaccgtgcc                                                  20

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
aacgataact gatccctggg                                                  20

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
cagttctacc tgtaggacag                                                  20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
cctccttcca ggtctccgga                                                  20

<210> SEQ ID NO 57
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
agcatgccag ccagagtcac t                                              21

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
actccaatct gagcaagacc                                                20

<210> SEQ ID NO 59
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gttatatgct gaacgaggtc                                                20

<210> SEQ ID NO 60
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
tgcgggcgga catggggaga tcc                                            23

<210> SEQ ID NO 61
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
atgggccgcc atacgacgac gctcaact                                       28

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
actcgataca ctggcctagc                                                20

<210> SEQ ID NO 63
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cggttcatca tggtacagtc                                                   20

<210> SEQ ID NO 64
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
cactgccttg tactcgggta gctg                                              24

<210> SEQ ID NO 65
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
agcgaggcat ggagagagcg gagcag                                            26

<210> SEQ ID NO 66
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ccttcttggt ccgcccgttc tta                                               23

<210> SEQ ID NO 67
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
tatgactcac ttccaggggg cact                                              24

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ctttgaggtc ctggtccatc acgtgaccat                                        30

<210> SEQ ID NO 69
<211> LENGTH: 24
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 69
gggcactgtt cagttcagcg gatc                                          24

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ttgccttaaa caagaccacg aaa                                           23

<210> SEQ ID NO 71
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tcgcttcctc ttcctccgac aca                                           23

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cactctcggc ctgtcttttc                                               20

<210> SEQ ID NO 73
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gttgttttgt tttggttttg gatat                                         25

<210> SEQ ID NO 74
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
atgggttgaa atattgggtt tattta                                        26

<210> SEQ ID NO 75
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 75
ccaccctcta accttaacct ctaac                                               25

<210> SEQ ID NO 76
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gaggatgttt tttaagtttt tttt                                                24

<210> SEQ ID NO 77
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
aatgtttatg gtggattttg taggt                                               25

<210> SEQ ID NO 78
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
cccacactca tatcaatata ataac                                               25

<210> SEQ ID NO 79
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gttgttttgt tttggttttg gatat                                               25

<210> SEQ ID NO 80
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
atgggttgaa atattgggtt tattta                                              26

<210> SEQ ID NO 81
<211> LENGTH: 25
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 81
ccaccctcta accttaacct ctaac                                              25

<210> SEQ ID NO 82
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gaggatgttt tttaagtttt tttt                                               24

<210> SEQ ID NO 83
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
aatgtttatg gtggattttg taggt                                              25

<210> SEQ ID NO 84
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cccacactca tatcaatata ataac                                              25

<210> SEQ ID NO 85
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gcacctgtgg ggaagaaact                                                    20

<210> SEQ ID NO 86
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
tgagagctgt ctcctactat cgatt                                              25

<210> SEQ ID NO 87
<211> LENGTH: 21
<212> TYPE: DNA
<213> ORGANISM: Artificial Sequence
<220> FEATURE:
<223> OTHER INFORMATION: Description of Artificial Sequence: Synthetic -continued

```
        primer

<400> SEQUENCE: 87
agaactggga ccactccagt g                                              21

<210> SEQ ID NO 88
<211> LENGTH: 24
<212> TYPE: DNA
<213> ORGANISM: Artificial Sequence
<220> FEATURE:
<223> OTHER INFORMATION: Description of Artificial Sequence: Synthetic
        primer

<400> SEQUENCE: 88
ttcaccctct ccactgacag atct                                           24

<210> SEQ ID NO 89
<211> LENGTH: 24
<212> TYPE: DNA
<213> ORGANISM: Artificial Sequence
<220> FEATURE:
<223> OTHER INFORMATION: Description of Artificial Sequence: Synthetic
        primer

<400> SEQUENCE: 89
ctaggccaca gaattgaaag atct                                           24

<210> SEQ ID NO 90
<211> LENGTH: 25
<212> TYPE: DNA
<213> ORGANISM: Artificial Sequence
<220> FEATURE:
<223> OTHER INFORMATION: Description of Artificial Sequence: Synthetic
        primer

<400> SEQUENCE: 90
gtaggtggaa attctagcat catcc                                          25
```

GENERATING PLURIPOTENT CELLS DE NOVO

CROSS-REFERENCE TO RELATED APPLICATIONS

This application is a 35 U.S.C. § 371 National Phase entry of International Application No. PCT/US2013/037966 filed Apr. 24, 2013, which claims benefit under 35 U.S.C. § 119(e) of U.S. Provisional Application Nos. 61/637,631 filed Apr. 24, 2012 and 61/779,533 filed Mar. 13, 2013, the contents of which are incorporated herein by reference in their entireties.

SEQUENCE LISTING

The instant application contains a Sequence Listing which has been submitted electronically in ASCII format and is hereby incorporated by reference in its entirety. Said ASCII copy, created on Oct. 22, 2014, is named 043214-071763-US_SL.txt and is 20,796 bytes.

TECHNICAL FIELD

The technology described herein relates to the production of pluripotent cells.

BACKGROUND

Current methods of obtaining pluripotent cells rely primarily upon tissues of limited availability (e.g. embryonic tissue or cord blood) or the addition of reprogramming factors (Hanna, J. et al. Cell 2008 133, 250-264; Hockemeyer, D. et al. Cell stem cell 2008 3, 346-353; Kim, D. et al. Cell stem cell 2009 4, 472-476; Kim, J. B. Nature 2009 461, 649-643; Okabe, M. et al. Blood 2009 114, 1764-1767), which involves introduction of exogenous nucleic acids. Methods of readily producing stem cells, particularly autologous stem cells, without the complications introduced by the addition of exogenous reprogramming factors, would accelerate research into cellular differentiation and the development of stem-cell based therapies. While it is hypothesized that damage to cells as a result of exposure to irritants, such as burns, chemical injury, trauma and radiation, may alter normal somatic cells to become cancer cells, there is no direct evidence that healthy adult somatic cells can be converted to other states without the specific manipulation of reprogramming factors.

Previously, researchers have reported finding "adult stem cells" in adult tissues (Reynolds, B. A. & Weiss, S. Science 1992 255, 1707-1710; Megeney, L. A. et al., Genes & development 1996 10, 1173-1183; Caplan, A. I. Journal of orthopaedic research 1991 9, 641-650; Lavker, R. M. & Sun, T. T. The Journal of investigative dermatology 1983 81, 121s-127s). Such reports remain controversial. For example, researchers looking for cells expressing the stem cell marker Oct4 failed to find Oct4-expressing cells in adult bone marrow in normal homeostasis, (Lengner, C. J. et al. Cell Cycle 2008 7, 725-728; Berg, J. S. & Goodell, M. A. Cell stem cell 2007 1, 359-360), while others report the ability to isolate Oct4-expressing cells from different adult tissues (Jiang, Y. et al. Nature 2010 418, 41-49; D'Ippolito, G. et al. Journal of cell science 2004 117, 2971-2981; Johnson, J. et al. Cell 2005 122, 303-315; Kucia, M. et al. Leukemia 2006 20, 857-869; Kuroda, Y. et al. PNAS 2011 107, 8639-8643; Obokata, H. et al. Tissue engineering. 2011 Part A 17, 607-615; Rahnemai-Azar, A. et al. Cytotherapy 2011 13, 179-192; Huang, Y. et al. Transplantation 2010 89, 677-685; Zuba-Surma, E. K. et al. Journal of cellular and molecular medicine 2011 15, 1319-1328; Paczkowska, E. et al. Annals of transplantation 2011 16, 59-71). It has been hypothesized that these cells represent either a population of adult stem cells or are merely an artifact of the techniques being used. In either case, they remain rare and do not represent an adequate source of pluripotent cells for research and therapeutic purposes.

SUMMARY

Described herein are methods of generating or producing pluripotent cells de novo, from, e.g., differentiated or adult cells. The methods described herein can further relate to increasing the pluripotency of a cell (or, e.g. decreasing the maturity of a cell), e.g. causing a multipotent cell to become pluripotent. Aspects of the technology described herein which relate to the production of pluripotent cells are based upon the inventors' recognition that environmental stresses can induce a cell to assume a more pluripotent phenotype.

In one aspect, described herein is a method to generate a pluripotent cell, comprising subjecting a cell to a stress comprising ATP, alone or in combination with another stress. In some embodiments, the method can further comprise selecting cells exhibiting pluripotency. In some embodiments, the cell is not present as part of a tissue. In some embodiments, the stress comprises removing at least about 40% of the cytoplasm from the cell. In some embodiments, the stress comprises removing at least about 40% of the mitochondria from the cell. In some embodiments, the stress is sufficient to disrupt the cellular membrane of at least 10% of cells exposed to the stress. In some embodiments, the cell is a somatic cell, a stem cell, a progenitor cell or an embryonic cell. In some embodiments, the cell is an isolated cell. In some embodiments, the cell is present in a heterogeneous population of cells. In some embodiments, the cell is present in a homogenous population of cells. In some embodiments, selecting the cells exhibiting pluripotency comprises selecting cells expressing Oct4 or Nanog, or Oct4 and Nanog expression. In some embodiments, selecting cells exhibiting pluripotency comprises selecting cell which are not adherent.

In some embodiments, at least about 50% of the cytoplasm is removed from the cell. In some embodiments, at least about 60% of the cytoplasm is removed from the cell. In some embodiments, between 60-80% of the cytoplasm is removed from the cell. In some embodiments, at least about 80% of the cytoplasm is removed from the cell. In some embodiments, at least about 90% of the cytoplasm is removed from the cell.

In some embodiments, the stress comprises exposure of the cell to at least one environmental stimulus selected from: trauma, mechanical stimuli, chemical exposure, ultrasonic stimulation, oxygen-deprivation, radiation, and exposure to extreme temperatures. In some embodiments, the stress comprises exposing the cell to a pH of from about 4.5 to about 6.0. In some embodiments, the stress comprises exposing the cell to a pH of from about 5.4 to about 5.8. In some embodiments, the cell is exposed for 1 day or less. In some embodiments, the cell is exposed for 1 hour or less. In some embodiments, the cell is exposed for about 30 minutes.

In some embodiments, the exposure to extreme temperatures comprises exposing the cell to temperatures below 35° C. or above 42° C. In some embodiments, the exposure to extreme temperatures comprises exposing the cell to temperatures at, or below freezing or exposure of the cell to temperatures at least about 85° C. In some embodiments, the mechanical stimulus comprises passing the cell through at least one device with a smaller aperture than the size of the cell. In some embodiments, the mechanical stimulus comprises passing the cell through several devices having progressively smaller apertures.

In some embodiments, the removal of a portion of the cytoplasm removes at least about 50% of the mitochondria from the cytoplasm. In some embodiments, the removal of cytoplasm or mitochondria removes about 50%-90% of the mitochondria from the cytoplasm. In some embodiments, the removal of cytoplasm or mitochondria removes more than 90% of the mitochondria from the cytoplasm.

In some embodiments, the method can further comprise culturing the pluripotent cell to allow propagation of the pluripotent cell. In some embodiments, the pluripotent cell expresses one or more pluripotent stem cell markers selected from the group consisting of Oct4 and Nanog.

In some embodiments, the cell is a mammalian cell. In some embodiments, the cell is a human cell. In some embodiments, the cell is an adult cell or a neonatal cell. In some embodiments, the method can further comprise maintaining the pluripotent cell in vitro. In some embodiments, the epigenetic state of the cell is altered to more closely resemble the epigenetic state of an embryonic stem cell. In some embodiments, the epigenetic state comprises methylation patterns.

In one aspect, described herein is an assay comprising contacting a pluripotent cell produced by the method described herein with a candidate agent. In some embodiments, the assay can be used to identify agents which affect one or more of the viability, differentiation, proliferation of the pluripotent cell.

In one aspect, described herein is the use of a pluripotent cell produced by the method described herein in a method of cell therapy for a subject.

In one aspect, described herein is a method of autologous cell therapy in a subject in need of cell therapy, comprising generating a pluripotent cell from a cell according to the method described herein, wherein the cell is obtained from the subject, and administering a composition comprising the pluripotent cell or a differentiated progeny thereof to the subject. In some embodiments, the method can further comprise differentiating the pluripotent cell along a predefined cell lineage prior to administering the composition to the subject.

In one aspect, described herein is a composition comprising a pluripotent cell, wherein the pluripotent cell is generated from a cell by the methods described herein.

In one aspect, described herein is a method of increasing the self-renewal ability of a pluripotent cell, the method comprising culturing the cell in the presence of adrenocorticotropic hormone (ACTH) or 3i medium. In some embodiments, the cell is cultured in LIF medium comprising ACTH. In some embodiments, the ACTH is present at a concentration of from about 0.1 µM to about 100 µM. In some embodiments, the cell is a cell generated by the method described herein. In some embodiments, the cell is a totipotent cell. In some embodiments, the cell is cultured in the presence of ACTH or 3i medium for at least 3 days. In some embodiments, the cell is cultured in the presence of ACTH or 3i medium for at least 5 days. In some embodiments, the cell is cultured in the presence of ACTH or 3i medium for at least 7 days. In some embodiments, after the culturing step, the cell expresses detectable level of a stem cell marker selected from the group consisting of Oct3/4; Nanog; Rex1; Klf4; Sox2; Klf2; Esrr-beta; Tbx3; and Klf5.

In some embodiments, the cells used in the methods described herein are in vivo. In some embodiments, the cells used in the methods described herein are in vitro.

BRIEF DESCRIPTION OF THE DRAWINGS

FIG. 1A depicts Oct4-GFP expression of stress treated cells. Stress-treated cells express Oct4-GFP, while untreated controls did not. Magnification of an Oct4-expressing colony is shown in the upper right in the stress-treated group. Scale bar indicates 100 µm. FIG. 1B depicts population analysis of stress-treated cells and non-stress treated control. A GFP expressing cell population is observed only in the stress treated group at day 5. FIG. 1C depicts cell-size analysis of CD 45 positive cells before and after the stress treatment at day 7. FIG. 1D depicts chronological change of CD45 positive cells after the stress treatment.

FIG. 2A depicts chronological gene expression change of pluripotent marker genes. The messenger RNA levels were normalized to GAPDH. (n=3, the average+S.D.) FIG. 2B depicts methylation analysis of Oct4 and Nanog promoter genes.

FIG. 3A depicts relative gene expression of stress defense genes during the ACCs generation phase. Samples were collected at day 3 and day 7 and compared with CD45 positive cells. (n=3, the average+S.D.) FIG. 3 B depicts total cellular ATP measurement. (n=3, the average+S.D.) FIG. 3C depicts ROS measurement. Error bars indicate SD. FIG. 3D depicts relative gene expression of mtDNA replication factors. (n=3, the average+S.D.)

FIG. 4A depicts a scheme of chimera mouse generation. Panel (i) demonstrates that ACs were dissociated into single cells with trypsin or (panel ii) ACs were cut into small pieces then injected into blastocysts. FIG. 4B depicts chimera contribution analysis. Tissues from 9 pups were analyzed by FACS.

FIG. 5A demonstrates that CD45 positive cells were exposed to various stresses and Oct4-GFP expression was analyzed by FACS. Percentage of Oct4-GFP expressing cells in survived cells after stress treatment. (n=3, the average+S.D.) FIG. 5B depicts the determination of pH condition. CD45 positive cells were exposed to different pH solutions. At 3 days after stress treatment, Oct4-GFP expression was analyzed by FACS. FIG. 5C depicts the determination of culture condition. Stress treated cells were cultured in various mediums. The number of GFP-expressing ACs was counted at day 14. (n=3, the average+S.D.)

FIG. 6A depicts chronological change of CD45 positive cells after stress treatment. The expression of E-cadherin and SSEA-1 was analyzed by FACS. FIG. 6B demonstrates that Oct4 gene expression of E-Cadherin/SSEA1 double positive cells was confirmed by RT-PCR. (n=3, the average+S.D.)

FIG. 7A depicts the ratio of Oct4-GFP expressing cells after stress treatment. Somatic cells were isolated from various tissues, and exposed to various stresses. Oct4-GFP expression was analyzed by FACS. FIG. 7B depicts embryonic gene expression of ACCs derived from various tissues. Gene expressions were normalized by GAPDH. (n=3, the average+S.D.)

DETAILED DESCRIPTION

Figure 1A:
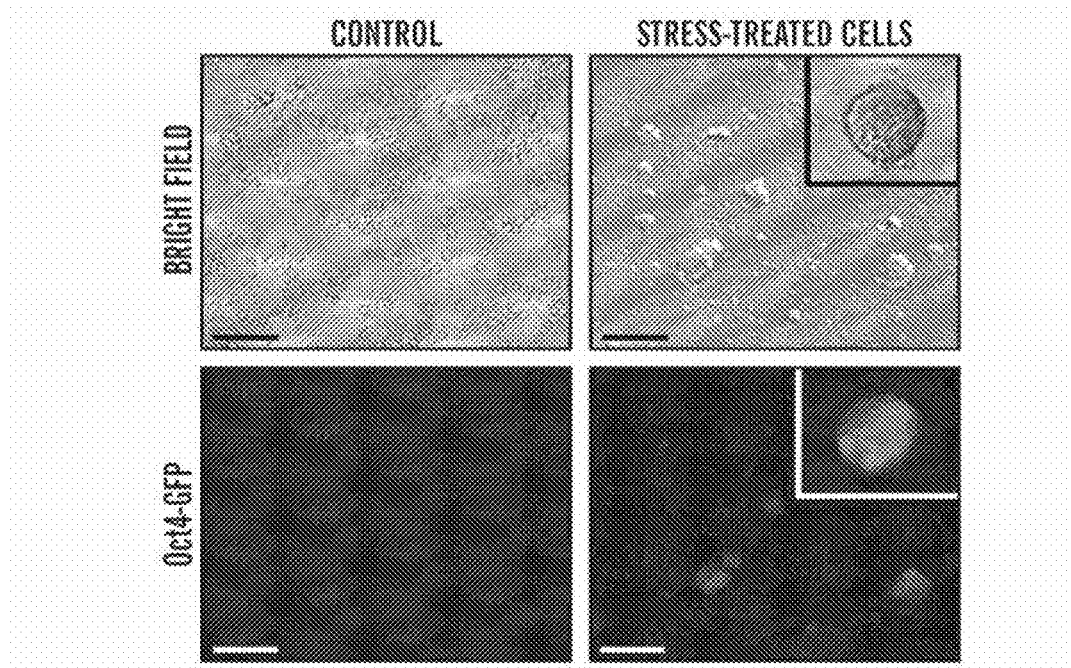
FIGS. 1A-1D depict Oct4 expressing cell generation from CD45 positive somatic cells.

Aspects of the technology described herein relate to the production or generation of pluripotent cells from cells. The aspects of the technology described herein are based upon the inventors' discovery that stress can induce the production of pluripotent stem cells from cells without the need to introduce an exogenous gene, a transcript, a protein, a nuclear component or cytoplasm to the cell, or without the need of cell fusion. In some embodiments, the stress induces a reduction in the amount of cytoplasm and/or mitochondria in a cell; triggering a dedifferentiation process and resulting in pluripotent cells. In some embodiments, the stress causes a disruption of the cell membrane, e.g. in at least 10% of the cells exposed to the stress. These pluripotent cells are characterized by one or more of, the ability to differentiate into each of the three germ layers (in vitro and/or in vivo), the generation of teratoma-like cell masses in vivo, and the ability to generate viable embryos and/or chimeric mice.

Described herein are experiments demonstrating that treatment of cells with certain environmental stresses, including, but not limited to stresses which reduce the amount of cytoplasm and/or mitochondria in the cell, can reduce mitochondrial activity, demethylate regions of the genome associated with dedifferentiation, cause the cells to display markers of known dedifferentiation pathways. Accordingly, in some embodiments, provided herein are methods of generating pluripotent cells from cells, the methods comprising removing at least about 40% of the cytoplasm and/or mitochondria from a cell, and selecting pluripotency or cells exhibiting pluripotency markers, wherein the cell is not present in a tissue. Also described herein are other stress treatments that can generate pluripotent cells from cells.

For convenience, certain terms employed herein, in the specification, examples and appended claims are collected here. Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are essential to the method or composition, yet open to the inclusion of unspecified elements, whether essential or not.

As used herein the term "consisting essentially of" refers to those elements required for a given embodiment. The term permits the presence of elements that do not materially affect the basic and novel or functional characteristic(s) of that embodiment.

The term "consisting of" refers to compositions, methods, and respective components thereof as described herein, which are exclusive of any element not recited in that description of the embodiment.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), and The Encyclopedia of Molecular Biology, published by Blackwell Science Ltd., 1994 (ISBN 0-632-02182-9). Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

The terms "decrease," "reduce," "reduced", and "reduction" are all used herein generally to mean a decrease by a statistically significant amount relative to a reference. However, for avoidance of doubt, "reduce," "reduction", or "decrease" typically means a decrease by at least 10% as compared to the absence of a given treatment and can include, for example, a decrease by at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, up to and including, for example, the complete absence of the given entity or parameter as compared to the absence of a given treatment, or any decrease between 10-99% as compared to the absence of a given treatment.

The terms "increased", "increase", or "enhance" are all used herein to generally mean an increase by a statically significant amount; for the avoidance of any doubt, the terms "increased", "increase", or "enhance" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

As used herein, the terms "treat," "treatment," "treating," or "amelioration" when used in reference to a disease, disorder or medical condition, refer to therapeutic treatments for a condition, wherein the object is to reverse, alleviate, ameliorate, inhibit, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a condition is reduced or halted. That is, "treatment" includes not just the improvement of symptoms or markers, but also a cessation or at least slowing of progress or worsening of symptoms that would be expected in the absence of treatment. Beneficial or desired clinical results include, but are not limited to, alleviation of one or more symptom(s), diminishment of extent of the deficit, stabilized (i.e., not worsening) state of health, delay or slowing of the disease progression, and amelioration or palliation of symptoms. Treatment can also include the subject surviving beyond when mortality would be expected statistically.

As used herein, the term "administering," refers to the placement of a pluripotent cell produced according to the methods described herein and/or the at least partially differentiated progeny of such a pluripotent cell into a subject by a method or route which results in at least partial localization of the cells at a desired site. A pharmaceutical composition comprising a pluripotent cell produced according to the methods described herein and/or the at least partially differentiated progeny of such a pluripotent cell can be administered by any appropriate route which results in an effective treatment in the subject.

As used herein, a "subject" means a human or animal. Usually the animal is a vertebrate such as a primate, rodent, domestic animal or game animal. Primates, for example, include chimpanzees, cynomologous monkeys, spider monkeys, and macaques, e.g., Rhesus monkeys. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above. In certain embodiments, the subject is a mammal, e.g., a primate, e.g., a human.

Preferably, the subject is a mammal. The mammal can be a human, non-human primate, mouse, rat, dog, cat, horse, or cow, but is not limited to these examples. Mammals other than humans can be advantageously used as subjects that represent animal models of a disease associated with a deficiency, malfunction, and/or failure of a given cell or tissue or a deficiency, malfunction, or failure of a stem cell compartment. In addition, the methods described herein can be used to treat domesticated animals and/or pets. A subject can be male or female. A subject can be one who has been previously diagnosed with or identified as suffering from or having a deficiency, malfunction, and/or failure of a cell type, tissue, or stem cell compartment or one or more diseases or conditions associated with such a condition, and optionally, but need not have already undergone treatment for such a condition. A subject can also be one who has been diagnosed with or identified as suffering from a condition including a deficiency, malfunction, and/or failure of a cell type or tissue or of a stem cell compartment, but who shows improvements in known risk factors as a result of receiving one or more treatments for such a condition. Alternatively, a subject can also be one who has not been previously diagnosed as having such a condition. For example, a subject can be one who exhibits one or more risk factors for such a condition or a subject who does not exhibit risk factors for such conditions.

As used herein, the term "select", when used in reference to a cell or population of cells, refers to choosing, separating, segregating, and/or selectively propagating one or more cells having a desired characteristic. The term "select" as used herein does not necessarily imply that cells without the desired characteristic are unable to propagate in the provided conditions.

As used herein, "maintain" refers to continuing the viability of a cell or population of cells. A maintained population will have a number of metabolically active cells. The number of these cells can be roughly stable over a period of at least one day or can grow.

As used herein, a "detectable level" refers to a level of a substance or activity in a sample that allows the amount of the substance or activity to be distinguished from a reference level, e.g. the level of substance or activity in a cell that has not been exposed to a stress. In some embodiments, a detectable level can be a level at least 10% greater than a reference level, e.g. 10% greater, 20% greater, 50% greater, 100% greater, 200% greater, or 300% or greater.

The term "statistically significant" or "significantly" refers to statistical significance and generally means a two standard deviation (2SD) difference above or below a reference, e.g. a concentration or abundance of a marker, e.g. a stem cell marker or differentiation marker. The term refers to statistical evidence that there is a difference. It is defined as the probability of making a decision to reject the null hypothesis when the null hypothesis is actually true. The decision is often made using the p-value.

Other than in the operating examples, or where otherwise indicated, all numbers expressing quantities of ingredients or reaction conditions used herein should be understood as modified in all instances by the term "about." The term "about" when used in connection with percentages can mean ±1%.

Other terms are defined herein within the description of the various aspects of the technology described herein.

The aspects of the technology described herein relate to methods of generating a pluripotent cell from a cell as well as uses and methods of using those pluripotent cells. In contrast with existing methods of generating pluripotent cells (i.e. induced pluripotent stem cells or iPS cells) which rely upon increasing the expression of reprogramming factors, for example, by introducing nucleic acid constructs encoding one or more reprogramming factors (e.g. Oct4), the methods described herein subject the cells to a stress but do not require introduction of foreign reprogramming agents.

In some embodiments, the stress reduces the volume of the cell's cytoplasm and/or the number of the cell's mitochondria. The reduction of the volume of the cell's cytoplasm or the number of the cell's mitochondria induces a stress response during which the cell acquires at least pluripotent capabilities. In one aspect, described herein is a method to generate a pluripotent cell, comprising removing at least about 40% of the cytoplasm from a cell, and selecting cells exhibiting pluripotency, wherein the cell is not present in a tissue. In one aspect, the invention as described herein relates to a method to generate a pluripotent cell, comprising removing at least about 40% of the mitochondria from a cell, and selecting cells exhibiting pluripotency, wherein the cell is not present in a tissue.

The cells used in the methods, assays, and compositions described herein can be any type of cell, e.g. an adult cell, an embryonic cell, a differentiated cell, a stem cell, a progenitor cell, and/or a somatic cell. A cell can be described by combinations of the terms described above, e.g. a cell can be an embryonic stem cell or a differentiated somatic cell. The cell used in the methods, assays, and compositions described herein can be obtained from a subject. In some embodiments, the cell is a mammalian cell. In some embodiments, the cell is a human cell. In some embodiments, the cell is an adult cell. In some embodiments, the cell is a neonatal cell. In some embodiments, the cell is a fetal cell. In some embodiments, the cell is an amniotic cell. In some embodiments, the cell is a cord blood cell.

"Adult" refers to tissues and cells derived from or within an animal subject at any time after birth. "Embryonic" refers to tissues and cells derived from or within an animal subject at any time prior to birth.

As used herein, the term "somatic cell" refers to any cell other than a germ cell, a cell present in or obtained from a pre-implantation embryo, or a cell resulting from proliferation of such a cell in vitro. Stated another way, a somatic cell refers to any cells forming the body of an organism, as opposed to germline cells. In mammals, germline cells (also known as "gametes") are the spermatozoa and ova which fuse during fertilization to produce a cell called a zygote, from which the entire mammalian embryo develops. Every other cell type in the mammalian body—apart from the sperm and ova, the cells from which they are made (gametocytes) and undifferentiated stem cells—is a somatic cell: internal organs, skin, bones, blood, and connective tissue are all made up of somatic cells. In some embodiments the somatic cell is a "non-embryonic somatic cell," by which is meant a somatic cell that is not present in or obtained from an embryo and does not result from proliferation of such a cell in vitro. In some embodiments the somatic cell is an "adult somatic cell," by which is meant a cell that is present in or obtained from an organism other than an embryo or a fetus or results from proliferation of such a cell in vitro. It is noted that adult and neonatal or embryonic cells can be distinguished by structural differences, e.g. epigenetic organization such as methylation patterns. In some embodiments, the somatic cell is a mammalian somatic cell. In some embodiments, the somatic cell is a human somatic cell. In some embodiments, the somatic cell is an adult somatic cell. In some embodiments, the somatic cell is a neonatal somatic cell.

As used herein, a "differentiated cell" refers to a cell that is more specialized in its fate or function than at a previous point in its development, and includes both cells that are terminally differentiated and cells that, although not terminally differentiated, are more specialized than at a previous point in their development. The development of a cell from an uncommitted cell (for example, a stem cell), to a cell with an increasing degree of commitment to a particular differentiated cell type, and finally to a terminally differentiated cell is known as progressive differentiation or progressive commitment. In the context of cell ontogeny, the adjective "differentiated", or "differentiating" is a relative term. A "differentiated cell" is a cell that has progressed further down the developmental pathway than the cell it is being compared with. Thus, stem cells can differentiate to lineage-restricted precursor cells (such as a mesodermal stem cell), which in turn can differentiate into other types of precursor cells further down the pathway (such as an cardiomyocyte precursor), and then to an end-stage differentiated cell, which plays a characteristic role in a certain tissue type, and may or may not retain the capacity to proliferate further.

As used herein, the term "stem cell" refers to a cell in an undifferentiated or partially differentiated state that has the property of self-renewal and has the developmental potential to naturally differentiate into a more differentiated cell type, without a specific implied meaning regarding developmental potential (i.e., totipotent, pluripotent, multipotent, etc.). By self-renewal is meant that a stem cell is capable of proliferation and giving rise to more such stem cells, while maintaining its developmental potential. Accordingly, the term "stem cell" refers to any subset of cells that have the developmental potential, under particular circumstances, to differentiate to a more specialized or differentiated phenotype, and which retain the capacity, under certain circumstances, to proliferate without substantially differentiating. The term "somatic stem cell" is used herein to refer to any stem cell derived from non-embryonic tissue, including fetal, juvenile, and adult tissue. Natural somatic stem cells have been isolated from a wide variety of adult tissues including blood, bone marrow, brain, olfactory epithelium, skin, pancreas, skeletal muscle, and cardiac muscle. Exemplary naturally occurring somatic stem cells include, but are not limited to, mesenchymal stem cells and hematopoietic stem cells. In some embodiments, the stem or progenitor cells can be embryonic stem cells. As used herein, "embryonic stem cells" refers to stem cells derived from tissue formed after fertilization but before the end of gestation, including pre-embryonic tissue (such as, for example, a blastocyst), embryonic tissue, or fetal tissue taken any time during gestation, typically but not necessarily before approximately 10-12 weeks gestation. Most frequently, embryonic stem cells are totipotent cells derived from the early embryo or blastocyst. Embryonic stem cells can be obtained directly from suitable tissue, including, but not limited to human tissue, or from established embryonic cell lines. In one embodiment, embryonic stem cells are obtained as described by Thomson et al. (U.S. Pat. Nos. 5,843,780 and 6,200,806; Science 282:1145, 1998; Curr. Top. Dev. Biol. 38:133 ff, 1998; Proc. Natl. Acad. Sci. U.S.A. 92:7844, 1995 which are incorporated by reference herein in their entirety).

Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, central nervous system stem cells, peripheral nervous system stem cells, and the like. Descriptions of stem cells, including method for isolating and culturing them, may be found in, among other places, Embryonic Stem Cells, Methods and Protocols, Turksen, ed., Humana Press, 2002; Weisman et al., Annu. Rev. Cell. Dev. Biol. 17:387 403; Pittinger et al., Science, 284:143 47, 1999; Animal Cell Culture, Masters, ed., Oxford University Press, 2000; Jackson et al., PNAS 96(25): 14482 86, 1999; Zuk et al., Tissue Engineering, 7:211 228, 2001 ("Zuk et al."); Atala et al., particularly Chapters 33 41; and U.S. Pat. Nos. 5,559,022, 5,672,346 and 5,827,735. Descriptions of stromal cells, including methods for isolating them, may be found in, among other places, Prockop, Science, 276:71 74, 1997; Theise et al., Hepatology, 31:235 40, 2000; Current Protocols in Cell Biology, Bonifacino et al., eds., John Wiley & Sons, 2000 (including updates through March, 2002); and U.S. Pat. No. 4,963,489.

As used herein, "progenitor cells" refers to cells in an undifferentiated or partially differentiated state and that have the developmental potential to differentiate into at least one more differentiated phenotype, without a specific implied meaning regarding developmental potential (i.e., totipotent, pluripotent, multipotent, etc.) and that does not have the property of self-renewal. Accordingly, the term "progenitor cell" refers to any subset of cells that have the developmental potential, under particular circumstances, to differentiate to a more specialized or differentiated phenotype. In some embodiments, the stem or progenitor cells are pluripotent stem cells. In some embodiments, the stem or progenitor cells are totipotent stem cells.

The term "totipotent" refers to a stem cell that can give rise to any tissue or cell type in the body. "Pluripotent" stem cells can give rise to any type of cell in the body except germ line cells. Stem cells that can give rise to a smaller or limited number of different cell types are generally termed "multipotent." Thus, totipotent cells differentiate into pluripotent cells that can give rise to most, but not all, of the tissues necessary for fetal development. Pluripotent cells undergo further differentiation into multipotent cells that are committed to give rise to cells that have a particular function. For example, multipotent hematopoietic stem cells give rise to the red blood cells, white blood cells and platelets in the blood.

The term "pluripotent" as used herein refers to a cell with the capacity, under different conditions, to differentiate to cell types characteristic of all three germ cell layers (i.e., endoderm (e.g., gut tissue), mesoderm (e.g., blood, muscle, and vessels), and ectoderm (e.g., skin and nerve)). Pluripotent cells are characterized primarily by their ability to differentiate to all three germ layers, using, for example, a nude mouse teratoma formation assay. Pluripotency is also evidenced by the expression of embryonic stem (ES) cell markers, although the preferred test for pluripotency is the demonstration of the capacity to differentiate into cells of each of the three germ layers.

The "ACC" and "STAP" cells described in the Examples herein, are non-limiting examples of pluripotent cells. The "STAP stem cells" are non-limiting examples of pluripotent stem cells. The term pluripotent cell and the term pluripotent stem cell may be used herein interchangeably because both cells can be used suitably for the purpose of the present invention.

The term "pluripotency" or a "pluripotent state" as used herein refers to a cell with the ability to differentiate into all three embryonic germ layers: endoderm (gut tissue), mesoderm (including blood, muscle, and vessels), and ectoderm (such as skin and nerve).

The term "multipotent" when used in reference to a "multipotent cell" refers to a cell that is able to differentiate into some but not all of the cells derived from all three germ layers. Thus, a multipotent cell is a partially differentiated cell. Multipotent cells are well known in the art, and non-limiting examples of multipotent cells can include adult stem cells, such as for example, hematopoietic stem cells and neural stem cells. Multipotent means a stem cell may form many types of cells in a given lineage, but not cells of other lineages. For example, a multipotent blood stem cell can form the many different types of blood cells (red, white, platelets, etc. . . . ), but it cannot form neurons. The term "multipotency" refers to a cell with the degree of developmental versatility that is less than totipotent and pluripotent.

The term "totipotency" refers to a cell with the degree of differentiation describing a capacity to make all of the cells in the adult body as well as the extra-embryonic tissues including the placenta. The fertilized egg (zygote) is totipotent as are the early cleaved cells (blastomeres)

The cell used in the methods described herein can be a cell which is not present in a tissue. As used herein, a "tissue" refers to an organized biomaterial (e.g. a group, layer, or aggregation) of similarly specialized cells united in the performance of at least one particular function. When cells are removed from an organized superstructure, or otherwise separated from an organized superstructure which exists in vivo, they are no longer present in a tissue. For example, when a blood sample is separated into two or more non-identical fractions, or a spleen is minced and mechanically-dissociated with Pasteur pipettes, the cells are no longer present in a tissue. In some embodiments, cells which are not present in a tissue are isolated cells. The term "isolated" as used herein in reference to cells refers to a cell that is mechanically or physically separated from another group of cells with which they are normally associated in vivo. Methods for isolating one or more cells from another group of cells are well known in the art. See, e.g., *Culture of Animal Cells: a manual of basic techniques* (3rd edition), 1994, R. I. Freshney (ed.), Wiley-Liss, Inc.; *Cells: a laboratory manual* (vol. 1), 1998, D. L. Spector, R. D. Goldman, L. A. Leinwand (eds.), Cold Spring Harbor Laboratory Press; *Animal Cells: culture and media,* 1994, D. C. Darling, S. J. Morgan, John Wiley and Sons, Ltd. Optionally the isolated cell has been cultured in vitro, e.g., in the presence of other cells.

In some embodiments, a cell, while not present in a tissue, is present in a population of cells. In some embodiments, the population of cells is a population of cells. As used herein, a "population of cells" refers to a group of at least 2 cells, e.g. 2 cells, 3 cells, 4 cells, 10 cells, 100 cells, 1000 cells, 10,000 cells, 100,000 cells or any value in between, or more cells. Optionally, a population of cells can be cells which have a common origin, e.g. they can be descended from the same parental cell, they can be clonal, they can be isolated from or descended from cells isolated from the same tissue, or they can be isolated from or descended from cells isolated from the same tissue sample. A population of cells can comprise 1 or more cell types, e.g. 1 cell type, 2 cell types, 3 cell types, 4 cell types or more cell types. A population of cells can be heterogeneous or homogeneous. A population of cells can be substantially homogeneous if it comprises at least 90% of the same cell type, e.g. 90%, 92%, 95%, 98%, 99%, or more of the cells in the population are of the same cell type. A population of cells can be heterogeneous if less than 90% of the cells present in the population are of the same cell type.

In some embodiments, the methods described herein can relate to making a non-pluripotent cell (e.g. a differentiated cell) assume a pluripotent phenotype. In some embodiments, generating a pluripotent cell can include generating a cell with a more pluripotent phenotype, i.e. causing a cell to assume a phenotype which has broader differentiation potential. By way of non-limiting example, very small embryonic-like cells (VSEL) cells can be unipotent instead of pluripotent, and/or be limited in their ability to differentiate into certain differentiated cell types (possibly due the epigenetic state of VSELs more closely resembling differentiated cells than embryonic stem cells). In accordance with the methods described herein, a unipotent cell and/or cell with limited differentiation ability can be caused to assume a more pluripotent phenotype. A more pluripotent phenotype can be a phenotype that is able to differentiate into a greater number of differentiated cell types e.g. of two unipotent cells, the one that can differentiate into a greater number of differentiated cell types of that lineage is more pluripotent and/or a pluripotent cell is more pluripotent than a unipotent cell.

The methods of generating a pluripotent cell (or more pluripotent cell) described herein can comprise, for example, removing part of the cytoplasm from a cell and/or removing mitochondria from a cell. In some embodiments, the removal of part of the cytoplasm or mitochondria from a cell removes partial epigenetic control of the cell. In some embodiments, at least about 40% of the cytoplasm is removed, e.g. at least about 40%, at least about 50%, at least about 60%, at least about 70%, at least about 80%, at least about 90% or more of the cytoplasm of a cell is removed. In some embodiments, between 60% and 80% of the cytoplasm of a cell is removed. In some embodiments, at least about 40% of the mitochondria are removed, e.g. at least about 40%, at least about 50%, at least about 60%, at least about 70%, at least about 80%, at least about 90% or more of the mitochondria of a cell are removed. In some embodiments, between 50% and 90% of the mitochondria of a cell are removed.

The method of subjecting the cell to stress and/or removing part of the cytoplasm or mitochondria from a cell can be any environmental stimulus that will cause pores and/or ruptures in the membrane of a cell below the threshold of lethality. The stress may comprise unphysiological stress in tissue or cell culture. Non-limiting examples of suitable environmental stimuli include trauma, mechanical stimuli, chemical exposure, ultrasonic stimulation, oxygen-deprivation, nutrient-deprivation, radiation, exposure to extreme temperatures, dissociation, trituration, physical stress, hyper osmosis, hypo osmosis, membrane damage, toxin, extreme ion concentration, active oxygen, UV exposure, strong visible light, deprivation of essential nutrition, or unphysiologically acidic environment. In some embodiments, one environmental stimulus can be applied to a cell. In some embodiments, multiple environmental stimuli can be applied to a cell, e.g. 2 stimuli, 3 stimuli, 4 stimuli or more stimuli can be applied. Multiple environmental stimuli can be applied concurrently or separately.

In some embodiments, the stress can be a stress that will cause membrane disruption in at least 10% of the cells exposed to the stress. As used herein, "membrane disruption" refers to compromising, rupturing, or disrupting a membrane such that pores or gaps form, sufficient to released a detectable amount of organelles and/or cellular material, including but not limited to mitochondria and DNA into the extracellular environment. Methods of detecting the release of cellular material, e.g. mitochondria are known in the art and described elsewhere herein. The released cellular material can be free or encapsulated or surrounded by membranes.

The stress can cause membrane disruption in at least 10% of the cells exposed to the stress, e.g. 10% or more, 20% or more, 30% or more, 40% or more 50% or more, 60% or more, 70% or more, 80% or more, or 90% or more. In some embodiments, the cells exposed to the stress can be cells of the same type and characteristics as the cells to be made more pluripotent as described herein, e.g. the stress suitable for one type of cell may not be suitable for another type of cell.

The length of time for which the cells are exposed to stress can vary depending upon the stimulus being used. For example, when using low nutrition conditions to stress cells according to the methods described herein, the cells can be cultured under low nutrition conditions for 1 week or more, e.g. 1 week, 2 weeks, or 3 weeks or longer. In some embodiments, the cells are cultured under low nutrition conditions for about 3 weeks. In another non-limiting example, cells exposed to low pH or hypoxic conditions according to the methods described herein can be exposed for minutes or long, e.g. including for several hours, e.g. for at least 2 minutes, for at least 5 minutes, for at least 20 minutes, for at least 1 hour, for at least 2 hours, for at least 6 hours or longer.

Mechanical stimuli that induce the generation of pluripotent cells can include any form of contact of a substance or surface with the cell membrane which will mechanically disrupt the integrity of the membrane. Mechanical stimulus can comprise exposing the cell to shear stress and/or high pressure. An exemplary form of mechanical stimulus is trituration. Trituration is a process of grinding and/or abrading the surface of a particle via friction. A non-limiting example of a process for trituration of a cell is to cause the cell to pass through a device wherein the device has an aperture smaller than the size of the cell. For example, a cell can be caused, by vacuum pressure and/or the flow of a fluid, to pass through a pipette in which at least part of the interior space of the pipette has a diameter smaller than the diameter of the cell. In some embodiments, the cell is passed through at least one device with a smaller aperture than the size of the cell. In some embodiments, the cell is passed through several devices having progressively smaller apertures. In some embodiments, cells can be triturated for 5 or more minutes, e.g. 5 minutes, 10 minutes, 20 minutes, 30 minutes, or 60 minutes. In some embodiments, the cells can be triturated by passing them through a Pasteur pipette with an internal diameter of 50 µm. In some embodiments, the cells can be triturated by passing them through a Pasteur pipette with an internal diameter of 50 µm for 20 minutes.

Other methods of applying stress necessary to induce cells to generate pluripotent cells include, for example, exposure to certain chemicals, or physico-chemical conditions (e.g. high or low pH, osmotic shock, temperature extremes, oxygen deprivation, etc). Treatments of this kind and others that induce the generation of pluripotent cells are discussed further below. Chemical exposure can include, for example, any combination of pH, osmotic pressure, and/or pore-forming compounds that disrupt or compromise the integrity of the cell membrane. By way of non-limiting example, the cells can be exposed to unphysiolosically acidic environment or low pH, streptolysin O, or distilled water (i.e. osmotic shock).

Low pH can include a pH lower than 6.8, e.g. 6.7, 6.5, 6.3, 6.0, 5.8, 5.4, 5.0, 4.5, 4.0, or lower. In some embodiments, the low pH is from about 3.0 to about 6.0. In some embodiments, the low pH is from about 4.5 to about 6.0. In some embodiments, the low pH is from 5.4 to 5.8. In some embodiments, the low pH is from 5.4 to 5.6. In some embodiments, the low pH is about 5.6. In some embodiments, the low pH is about 5.7. In some embodiments, the low pH is about 5.5. In some embodiments, the cells can be exposed to low pH conditions for up to several days, e.g. for 6 days or less, for 4 days or less, for 3 days or less, for 2 days or less, for 1 day or less, for 12 hours or less, for 6 hours or less, for 3 hours or less, for 2 hours or less, for 1 hour or less, for 30 minutes or less, for 20 minutes or less, or less than 10 minutes. In some embodiments, the cells can be exposed to a pH from 5.4 to 5.6 for 3 days or less. In some embodiments, the cells can be exposed to a pH of from about 5.6 to 6.8 for 3 days or less. In some embodiments, the cells can be exposed of a pH of from about 5.6 to 6.8 for 1 hour or less. In some embodiments, the cells can be exposed of a pH of from about 5.6 to 6.8 for about 30 minutes. In some embodiments, the cells can be exposed of a pH of from about 5.6 to 6.8 for about 20 minutes. In some embodiments, the cells can be exposed to a pH of from about 5.6 to 5.8 for 3 days or less. In some embodiments, the cells can be exposed of a pH of from about 5.6 to 5.8 for 1 hour or less. In some embodiments, the cells can be exposed of a pH of from about 5.6 to 5.8 for about 30 minutes. In some embodiments, the cells can be exposed of a pH of from about 5.6 to 5.8 for about 20 minutes.

In some embodiments, cells can be exposed to ATP to induce the generation of pluripotent cells. In some embodiments, cells can be exposed to ATP at concentrations from about 20 µM to about 200 mM. In some embodiments, cells can be exposed to ATP at concentrations from about 200 µM to about 20 mM. In some embodiments, cells can be exposed to ATP at concentrations of about 2.4 mM. In some embodiments, cell can be exposed to ATP diluted in HBSS. In some embodiments, cells can be exposed to ATP for 1 minute or longer, e.g. at least 1 minute, at least 2 minutes, at least 5 minutes, at least 15 minutes, at least 30 minutes, at least 45 minutes, at least 1 hour or longer. In some embodiments, the cells can be exposed to ATP for from about 5 minutes to about 30 minutes. In some embodiments, the cells can be exposed to ATP for about 15 minutes. In some embodiments, the cells can be exposed to about 2.4 mM ATP for about 15 minutes.

In some embodiments, cells can be exposed to $CaCl_2$ to induce the generation of pluripotent cells. In some embodiments, cells can be exposed to $CaCl_2$ at concentrations from about 20 µM to about 200 mM. In some embodiments, cells can be exposed to $CaCl_2$ at concentrations from about 200 µM to about 20 mM. In some embodiments, cells can be exposed to $CaCl_2$ at concentrations of about 2 mM. In some embodiments, cells can be exposed to $CaCl_2$ diluted in HBSS. In some embodiments, cells can be exposed to $CaCl_2$ for 1 day or longer, e.g. at least 1 day, at least 2 days, at least 1 week, at least 2 weeks, at least 3 weeks or longer. In some embodiments, the cells can be exposed to $CaCl_2$) for from about 1 week to 3 weeks. In some embodiments, the cells can be exposed to $CaCl_2$ for about 2 weeks. In some embodiments, the cells can be exposed to about 2 mM $CaCl_2$) for about 2 weeks. In some embodiments, the cells can be exposed to about 2 mM $CaCl_2$) for about 1 week.

Examples of pore-forming compounds include streptolysin O (SLO), saponin, digitonin, filipin, Ae I, cytolysin of sea anemone, aerolysin, amatoxin, amoebapore, amoebapore homolog from *Entamoeba dispar*, brevinin-1E, brevinin-2E, barbatolysin, cytolysin of *Enterococcus faecalis*, delta hemolysin, diphtheria toxin, El Tor cytolysin of *Vibrio cholerae*, equinatoxin, enterotoxin of *Aeromonas hydrophila*, esculentin, granulysin, haemolysin of *Vibrio parahaemolyticus*, intermedilysin of *Streptococcus intermedins*, the lentivirus lytic peptide, leukotoxin of *Actinobacillus actinomycetemcomitans*, magainin, melittin, membrane-associated lymphotoxin, Met-enkephalin, neokyotorphin, neokyotorphin fragment 1, neokyotorphin fragment 2, neokyotorphin fragment 3, neokyotorphin fragment 4, NKlysin, paradaxin, alpha cytolysin of *Staphylococcus aureus*, alpha cytolysin of *Clostridium septicum*, *Bacillus thuringiensis* toxin, colicin, complement, defensin, histolysin, listeriolysin, magainin, melittin, pneumolysin, yeast killer toxin, valinomycin, Peterson's crown ethers, perforin, perfringolysin O, theta-toxin of *Clostridium perfringens*, phallolysin, phallotoxin, and other molecules, such as those described in Regen et al. Biochem Biophys Res Commun 1989 159:566-571; which is incorporated herein by reference in its entirety. Methods of purifying or synthesizing pore-forming compounds are well known to one of ordinary skill in the art. Further, pore-forming compounds are commercially available, e.g. streptolysin O (Cat No. 55265; Sigma-Aldrich; St. Louis, MO). By way of non-limiting example, cells can be exposed to SLO for about 5 minutes or more, e.g. at least 5 minutes, at least 10 minutes, at least 20 minutes, at least 30 minutes, at least 45 minutes, at least 1 hour, at least 2 hours, at least 3 hours, or longer. In some embodiments, cells are exposed to SLO for from about 30 minutes to 2 hours. In some embodiments, cells are exposed to SLO for about 50 minutes. By way of non-limiting example, cells can be exposed to SLO at concentrations of from about 10 ng/mL to 1 mg/mL. In some embodiments, cells can be exposed to SLO at concentrations of from about 1 µg/mL to 100 µg/mL. In some embodiments, cells can be exposed to SLO at about 10 µg/mL. In some embodiments, cells can be exposed to SLO at about 10 µg/mL for about 50 minutes.

Oxygen-deprivation conditions that induce the generation of pluripotent cells can include culturing cells under reduced oxygen conditions, e.g. culturing cells in 10% oxygen or less. In some embodiments, the cells are cultured under 5% oxygen or less. The length of culturing under reduced oxygen conditions can be 1 hour or longer, e.g. 1 hour, 12 hours, 1 day, 2 days, 1 week, 2 weeks, 3 weeks, 1 month, 2 months or longer. In some embodiments, the cells can be cultured under reduced oxygen conditions for from 1 week to 1 month. In some embodiments, the cells can be cultured under reduced oxygen conditions for about 3 weeks.

Nutrient-deprivation conditions that induce the generation of pluripotent cells can include the lack of any factor or nutrient that is beneficial to cell growth. In some embodiments, nutrient-deprivation conditions comprise culturing the cells in basal culture medium, e.g. F12 or DMEM without further supplements such as FBS or growth factors. The length of culturing in nutrient-deprivation conditions can be 1 hour or longer, e.g. 1 hour, 12 hours, 1 day, 2 days, 1 week, 2 weeks, 3 weeks, 1 month, 2 months or longer. In some embodiments, the cells can be cultured under nutrient-deprivation conditions for from 1 week to 1 month. In some embodiments, the cells can be cultured under nutrient-deprivation conditions for about 2 weeks. In some embodiments, the cells can be cultured under nutrient-deprivation conditions for about 3 weeks. In some embodiments, nutrient-deprivation conditions can include conditions with no growth factors or conditions with less than 50% of a standard concentration of one or more growth factors for a given cell type.

Exposure to extreme temperatures that induces the generation of pluripotent cells can include exposure to either low temperatures or high temperatures. For a mammalian cell, an extreme low temperature can be a temperature below 35° C., e.g. 34° C., 33° C., 32° C., 31° C., or lower. In some embodiments, an extreme low temperature can be a temperature below freezing. Freezing of cells can cause membrane perforations by ice crystals and provides an avenue for reducing cytoplasm. For a mammalian cell, an extreme high temperature can be a temperature above 42° C., e.g. 43° C., 44° C., 45° C., 46° C. or higher. In some embodiments, the extreme high temperature can be a temperature of about 85° C. or higher. The length of culturing under extreme temperatures can be 20 minutes or longer, e.g. 20 minutes, 30 minutes, 1 hour, 12 hours, 1 day, 2 days, 1 week, 2 weeks, 3 weeks, 1 month, 2 months or longer. Clearly, the higher the temperature, the shorter the exposure that will generally be tolerated to permit the generation of pluripotent cells.

Further examples of stresses that can be used in the methods described herein include, but are not limited to, ultrasonic stimulation and radiation treatment.

In some embodiments, after being exposed to a stress, the cells can be cultured prior to selection according to the methods described below herein. The cells can be cultured for at least 1 hour prior to selection, e.g. the stressful stimulus is removed and the cells are cultured for at least 1 hour, at least 2 hours, at least 6 hours, at least 12 hours, at least 1 day, at least 2 days, at least 7 days or longer prior to selecting as described herein. By way of non-limiting example, cells can be exposed to SLO for about 50 minutes and then cultured in culture medium without SLO for about 7 days prior to selection. In some embodiments, the culture medium used to culture the cells prior to selection does not contain differentiation factors or promote differentiation. In some embodiments, the culture medium is one suitable for the culture of stem cells and/or pluripotent cells. Examples of such media are described below herein.

In some embodiments, the amount of cytoplasm in a cell is reduced. The reduction of cytoplasm in a cell can be determined by monitoring the size of the cell. Methods of determining cell size are well known to one of ordinary skill in the art and include, by way of non-limiting example, cytofluorimetric analysis. In brief, single cells are stained with propidium iodide filtered and measured, for example, on a DAKO GALAXY™ (DAKO) analyzer using FLO-MAX™ software. Cytofluorimetric analysis can then be performed to establish cell size. Microbeads of predefined sizes are re-suspended in isotonic phosphate saline (pH 7.2) and used as a standard for which to compare size of cells contained in spheres using cytofluorimetric analysis. Both cells and beads are analyzed using the same instrument setting (forward scatter, representing cell and bead size, and side scatter, representing cellular granularity). Cell size can be calculated on a curve employing bead size on the x-axis and forward scatter values on the y-axis.

In some embodiments, the amount of mitochondria in a cell is reduced. Methods of determining the number of mitochondria in a cell are well known to one of ordinary skill in the art and include staining with a mitochondria-specific dye and counting the number of mitochondria visible per cell when viewed under a microscope. Mitochondria-specific dyes are commercially available, e.g. MITOTRACKER™ (Cat No M7512 Invitrogen; Grand Island, NY). In some embodiments, the number of mitochondria or the intensity of the signal from mitochondria-specific dyes can be decreased by at least 40% following treatment with the methods described above herein. In some embodiments, cells are selected in which the number of mitochondria or the intensity of the signal from mitochondria-specific dyes decreased by at least 40% following treatment with the methods described above herein.

The amount of mitochondria and/or membrane disruption can also be detected by measuring redox activity in the extracellular environment. As mitochondria are released into the extracellular environment by the stress described herein, the level of ROS in the extracellular environment can increase and can be used to measure the effectiveness of a given stress.

In some embodiments of any of the aspects described herein, the cell can be subjected to a stress while in the presence of LIF (leukemia inhibitory factor).

In some aspects, after removing a portion of the cytoplasm and/or mitochondria of a cell, the method further comprises selecting cells exhibiting pluripotency. Pluripotent cells can be selected by selecting cells which display markers, phenotypes, or functions of pluripotent cells. Selecting cells can comprise isolating and propagating cells displaying the desired characteristics or culturing a population of cells with unknown characteristics under conditions such that cells with the desired characteristic(s) will survive and/or propagate at a higher rate than those cells not having the desired characteristic(s). Non-limiting examples of markers and characteristics of pluripotent cells are described herein below. In some embodiments, selecting the cells for pluripotency comprises, at least in part, selecting cells which express Oct4. In some embodiments, selecting the cells for pluripotency comprises, at least in part, selecting cells which express Nanog. In some embodiments, selecting the cells for pluripotency comprises, at least in part, selecting cells which express Oct4, Nanog, E-cadherin, and/or SSEA. In some embodiments, pluripotent cells can be selected by selecting cells expressing SSEA-1 and E-cadherin using antibodies specific for those markers and FACS. In some embodiments cells can be selected on the basis of size using FACS or other cell sorting devices as known in the art and/or described herein. Cells can also be selected by their inability to adhere to culture dishes.

Cells can also be selected on the basis of smaller size after being subjected to stress. That is, stressed cells that progress to pluripotency are smaller than their non-pluripotent somatic precursors. In some embodiments, cells with a diameter of less than 8 μm are selected, e.g. cells with a diameter of 8 μm or less, 7 μm or less, 6 μm or less, 5 μm or less, or smaller. Cells can be selected on the basis of size after being cultured for a brief period (e.g. several minutes to several days) or after being allowed to rest following the stress treatment. In some embodiments, the cells can be selected on the basis of size immediately following the stress treatment. Cells can be selected on the basis of size by any method known in the art, e.g. the use of a filter or by FACS.

In some embodiments of the methods described herein, a pluripotent cell generated according to the methods described herein can be cultured to permit propagation of that pluripotent cell (i.e. propagation of a stem cell). In some embodiments, a pluripotent cell generated according to the methods described herein can be maintained in vitro. In one aspect, the technology described herein relates to a composition comprising a pluripotent cell and/or the at least partially differentiated progeny thereof. In some embodiments, the pluripotent cell and/or the at least partially differentiated progeny thereof can be maintained in vitro, e.g. as a cell line. Cell lines can be used to screen for and/or test candidate agents, e.g. therapeutic agents for a given disease and/or agents that modulate stem cells, as described below herein. In some embodiments, the pluripotent cell and/or the at least partially differentiated progeny thereof can be derived from a cell obtained from a subject with a disease, e.g. a disease associated with the failure of a naturally occurring cell or tissue type or a naturally occurring pluripotent and/or multipotent cell (as described herein below), and/or a disease involving cells which have genetic mutations, e.g. cancer. The compositions described herein, can be used, e.g. in disease modeling, drug discovery, diagnostics, and individualized therapy.

Conditions suitable for the propagation and or maintaining of stem and/or pluripotent cells are known in the art. Propagation of stem cells permits expansion of cell numbers without substantially inducing or permitting differentiation By way of non-limiting example, conditions suitable for propagation of pluripotent cells include plating cells at $1 \times 10^6$ cells/cm$^2$ in F12/DMEM (1:1, v/v) supplemented with 2% B27, 20 ng/mL basic fibroblast growth factor, and 10 ng/mL epidermal growth factor. About 50% of the medium can be replaced every 2-3 days for the duration of the culture. In some embodiments, the conditions suitable for the propagation of stem and/or pluripotent cells comprise culturing the cells in B27-LIF (i.e. serum-free medium containing LIP ($1 \times 10^3$ units/mL, Chemicon; Cat No: ESG1107 EMD Millipore, Billerica, MA) and B27 supplement (Cat No: 0080085-SA; Invitrogen; Grand Island, NY) as described in Hitoshi, S. et al. *Genes & development* 2004 18, 1806-1811; which is incorporated by reference herein in its entirety. Other media suitable for culturing the cells described herein are described in the Examples herein, e.g. ES establishment culture medium, 2i, 3i and ACTH, ES culture condition, ES-LIF, embryonic neural stem cell culture condition, and EpiSCs culture condition. In some embodiments, conditions for the propagation or maintenance of pluripotent cells can include culture the cells in the presence of LIF (leukemia inhibitory factor).

During propagation, the pluripotent cell generated according to the methods described herein will continue to express the same pluripotent stem cell marker(s). Non-limiting examples of pluripotent stem cell markers include SSEA-1, SSEA-2, SSEA-3, SSEA-4 (collectively referred to herein as SSEA), AP, E-cadherin antigen, Oct4, Nanog, Ecat1, Rex1, Zfp296, GDF3, Dppa3, Dppa4, Dppa5, Sox2, Esrrb, Dnmt3b, Dnmt31, Utf1, Tcl1, Bat1, Fgf4, Neo, Cripto, Cdx2, and Slc2a3. Methods of determining if a cell is expressing a pluripotent stem cell marker are well known to one of ordinary skill in the art and include, for example, RT-PCR, the use of reporter gene constructs (e.g. expression of the Oct4-GFP construct described herein coupled with FACS or fluorescence microscopy), and FACS or fluorescence microscopy using antibodies specific for cell surface markers of interest.

Pluripotent cell markers also include elongated telomeres, as compared to cells. Telomere length can be determined, for example, by isolating genomic DNA, digesting the gDNA with restriction enzymes such as Hinf1 and Rsa1, and detecting telomeres with a telomere length assay reagent. Such reagents are known in the art and are commercially available, e.g. the TELOTAGGG™ TELOMERE LENGTH ASSAY kit (Cat No. 12209136001 Roche; Indianapolis, IN).

In some embodiments, a cell treated according to the methods described herein can be altered to more closely resemble the epigenetic state of an embryonic stem cell than it did prior to being treated in accordance with the disclosed methods. The epigenetic state of a cell refers to the chemical marking of the genome as opposed to changes in the nucleotide sequence of the genome. Epigenetic marks can include DNA methylation (imprints) as well as methylation and acetylation of proteins associated with DNA, such as histones. The term 'DNA methylation' refers to the addition of a methyl ($CH_3$) group to a specific base in the DNA. In mammals, methylation occurs almost exclusively at the 5 position on a cytosine when this is followed by a guanine (CpG). In some embodiments, the epigenetic state can comprise epigenetic methylation patterns, e.g. DNA methylation patterns. Assays for determining the presence and location of epigenetic markings are known in the art, and can include bisulfite sequencing. Briefly, DNA is treated with the CpGenome™ DNA Modification Kit (Chemicon, Temecula, CA) and regions of interest (e.g. the Nanog and Oct4 genes) are amplified and sequenced.

Some aspects of the technology described herein relate to assays using a pluripotent stem cell produced by the methods described herein. For example, a pluripotent stem cell produced by the methods described herein can be used to screen and/or identify agents which modulate the viability, differentiation, or propagation of pluripotent stem cells. Such assays can comprise contacting a pluripotent cell produced according to the methods described herein with a candidate agent and determining whether the viability, differentiation and/or propagation of the pluripotent cell contacted with the candidate agent varies from the viability, differentiation and/or propagation of a pluripotent cell not contacted with the candidate agent. In some embodiments, an agent can increase the viability, differentiation, and/or propagation of the pluripotent stem cell. In some embodiments, an agent can decrease the viability, differentiation, and/or propagation of the pluripotent stem cell. In some embodiments, the pluripotent stem cell can be contacted with multiple candidate agents, e.g. to determine synergistic or antagonistic effects or to screen candidate agents in pools.

A candidate agent is identified as an agent that modulates the viability of a pluripotent cell produced if the number of pluripotent cells which are viable, i.e. alive is higher or lower in the presence of the candidate agent relative to its absence. Methods of determining the viability of a cell are well known in the art and include, by way of non-limiting example determining the number of viable cells at at least two time points, by detecting the strength of a signal from a live cell marker, or the number or proportion of cells stained by a live cell marker. Live cell markers are available commercially, e.g. PRESTO BLUE™ (Cat No A-13261; Life Technologies; Grand Island, NY). A candidate agent is identified as an agent that modulates the propagation of a pluripotent cell produced if the rate of propagation of the pluripotent cell is altered, i.e. the number of progeny cells produced in a given time is higher or lower in the presence of the candidate agent. Methods of determining the rate of propagation of a cell are known in the art and include, by way of non-limiting example, determining an increase in live cell number over time.

A candidate agent is identified as an agent that modulates the differentiation of a pluripotent cell if the rate or character of the differentiation of the pluripotent cell is higher or lower in the presence of the candidate agent. Methods of determining the rate or character of differentiation of a cell are known in the art and include, by way of non-limiting example, detecting markers or morphology of a particular lineage and comparing the number of cells and/or the rate of appearance of cells with such markers or morphology in the population contacted with a candidate agent to a population not contacted with the candidate agent. Markers and morphological characteristics of various cell fate lineages and mature cell types are known in the art. By way of non-limiting example, mesodermal cells are distinguished from pluripotent cells by the expression of actin, myosin, and desmin. Chondrocytes can be distinguished from their precursor cell types by staining with safranin-O and or FAST-GREEN™ dyes (Fisher; Pittsburgh, PA; F99). Osteocytes can be distinguished from their precursor cell types by staining with Alizarin Red S (Sigma; St. Louis, MO: Cat No A5533).

In some embodiments, a candidate agent can be an potential inhibitor of tumor stem cells, e.g. the methods described herein can be used to create pluripotent cells from mature tumor cells, and used to screen for agents which inhibit the creation and/or viability of tumor cells. The methods described herein can also be used to screen for agents which kill mature tumor cells but which do not promote the development and/or survival of tumor stem cells.

In some embodiments, the pluripotent cells are contacted with one or more candidate agents and cultured under conditions which promote differentiation to a particular cell lineage or mature cell type. Conditions suitable for differentiation are known in the art. By way of non-limiting example, conditions suitable for differentiation to the mesoderm lineage include DMEM supplemented with 20% fetal calf serum (FCS), with the medium exchanged every 3 days. By way of further non-limiting example, conditions suitable for differentiation to the neural lineage include plating cells on ornithin-coated chamber slides in F12/DMEM (1:1, v/v) supplemented 2% B27, 10% FCS, 10 ng/mL bFGF, and 20 ng/m LEGF. The medium can be exchanged every 3 days.

As used herein, a "candidate agent" refers to any entity which is normally not present or not present at the levels being administered to a cell, tissue or subject. A candidate agent can be selected from a group comprising: chemicals; small organic or inorganic molecules; nucleic acid sequences; nucleic acid analogues; proteins; peptides; aptamers; peptidomimetic, peptide derivative, peptide analogs, antibodies; intrabodies; biological macromolecules, extracts made from biological materials such as bacteria, plants, fungi, or animal cells or tissues; naturally occurring or synthetic compositions or functional fragments thereof. In some embodiments, the candidate agent is any chemical entity or moiety, including without limitation synthetic and naturally-occurring non-proteinaceous entities. In certain embodiments the candidate agent is a small molecule having a chemical moiety. For example, chemical moieties include unsubstituted or substituted alkyl, aromatic, or heterocyclyl moieties including macrolides, leptomycins and related natural products or analogues thereof. Candidate agents can be known to have a desired activity and/or property, or can be selected from a library of diverse compounds.

Candidate agents can be screened for their ability to modulate the viability, propagation, and/or differentiation of a pluripotent cell. In one embodiment, candidate agents are screened using the assays for viability, differentiation, and/or propagation described above and in the Examples herein.

Generally, compounds can be tested at any concentration that can modulate cellular function, gene expression or protein activity relative to a control over an appropriate time period. In some embodiments, compounds are tested at concentrations in the range of about 0.1 nM to about 1000 mM. In one embodiment, the compound is tested in the range of about 0.1 µM to about 20 µM, about 0.1 µM to about 10 µM, or about 0.1 µM to about 5 µM.

Depending upon the particular embodiment being practiced, the candidate or test agents can be provided free in solution, or can be attached to a carrier, or a solid support, e.g., beads. A number of suitable solid supports can be employed for immobilization of the test agents. Examples of suitable solid supports include agarose, cellulose, dextran (commercially available as, e.g., Sephadex, Sepharose) carboxymethyl cellulose, polystyrene, polyethylene glycol (PEG), filter paper, nitrocellulose, ion exchange resins, plastic films, polyaminemethylvinylether maleic acid copolymer, glass beads, amino acid copolymer, ethylene-maleic acid copolymer, nylon, silk, etc. Additionally, for the methods described herein, test agents can be screened individually, or in groups or pools. Group screening is particularly useful where hit rates for effective test agents are expected to be low, such that one would not expect more than one positive result for a given group.

Methods for developing small molecule, polymeric and genome based libraries are described, for example, in Ding, et al. J Am. Chem. Soc. 124: 1594-1596 (2002) and Lynn, et al., J. Am. Chem. Soc. 123: 8155-8156 (2001). Commercially available compound libraries can be obtained from, e.g., ArQule (Woburn, MA), Invitrogen (Carlsbad, CA), Ryan Scientific (Mt. Pleasant, SC), and Enzo Life Sciences (Farmingdale, NY). These libraries can be screened for the ability of members to modulate the viability, propagation, and/or differentiation of pluripotent stem cells. The candidate agents can be naturally occurring proteins or their fragments. Such candidate agents can be obtained from a natural source, e.g., a cell or tissue lysate. Libraries of polypeptide agents can also be prepared, e.g., from a cDNA library commercially available or generated with routine methods. The candidate agents can also be peptides, e.g., peptides of from about 5 to about 30 amino acids, with from about 5 to about 20 amino acids being preferred and from about 7 to about 15 being particularly preferred. The peptides can be digests of naturally occurring proteins, random peptides, or "biased" random peptides. In some methods, the candidate agents are polypeptides or proteins. Peptide libraries, e.g. combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The candidate agents can also be nucleic acids. Nucleic acid candidate agents can be naturally occurring nucleic acids, random nucleic acids, or "biased" random nucleic acids. For example, digests of prokaryotic or eukaryotic genomes can be similarly used as described above for proteins.

In some embodiments, the candidate agent that is screened and identified to modulate viability, propagation and/or differentiation of a pluripotent cell according to the methods described herein, can increase viability, propagation and/or differentiation of a pluripotent cell by at least 5%, preferably at least 10%, 20%, 30%, 40%, 50%, 60%, 70%, 80%, 90%, 1-fold, 1.1-fold, 1.5-fold, 2-fold, 3-fold, 4-fold, 5-fold, 10-fold, 50-fold, 100-fold or more relative to an untreated control. In some embodiments, the candidate agent that is screened and identified to modulate viability, propagation and/or differentiation of a pluripotent cell according to the methods described herein, can decrease viability, propagation and/or differentiation of a pluripotent cell by at least 5%, preferably at least 10%, 20%, 30%, 40%, 50%, 50%, 70%, 80%, 90%, 95%, 97%, 98%, 99% or more, up to and including complete reduction (i.e., zero viability, growth, propagation, or differentiation) relative to an untreated control.

In some embodiments, the candidate agent functions directly in the form in which it is administered. Alternatively, the candidate agent can be modified or utilized intracellularly to produce a form that modulates the desired activity, e.g. introduction of a nucleic acid sequence into a cell and its transcription resulting in the production of an inhibitor or activator of gene expression or protein activity within the cell.

It is contemplated that the methods and compositions described herein can be used, e.g. in the development of cancer vaccines. Generating at least partially differentiated progeny of pluripotent tumor cells obtained as described herein (e.g. by treating a mature tumor cell in accordance with the methods described herein) can provide a diverse and changing antigen profile which can permit the development of more powerful APC (antigen presenting cells)-based cancer vaccines.

In some embodiments, the methods described herein relate to increasing the transformation efficiency of a cell. Stressing cells, e.g., inducing pluripotency as described herein can make the cells more receptive to methods of genetic modification including but not limited to transgene insertion, viral vectors, and/or zinc finger endonucleases. It is contemplated that the methods described herein can permit cells to be modified to a genetically receptive state such that naked DNA could be used to transform the resulting pluripotent cells.

Some aspects of the technology described herein relate to methods of cell therapy comprising administering a pluripotent cell, produced by the methods described herein, or the at least partially differentiated progeny of such a cell to a subject in need of cell therapy. In some embodiments, a therapeutically effective amount of pluripotent cells or the at least partially differentiated progeny of the pluripotent cell is provided. In some embodiments, the pluripotent cells and/or their progeny are autologous. In some embodiments, the pluripotent cells and/or their progeny are allogeneic. In some embodiments, the pluripotent cells and/or their progeny are autologous. In some embodiments, the pluripotent cells and/or their progeny are HLA-matched allogeneic. In some embodiments, the pluripotent cells and/or their progeny are syngeneic. In some embodiments, the pluripotent cells and/or their progeny are xenogenic. In some embodiments, the cell therapy can be autologous therapy, e.g. a cell from a subject can be used to generate a pluripotent cell according to the methods described herein and the pluripotent cell and/or at least partially differentiated progeny of that pluripotent cell can be administered to the subject. As used herein, a "subject in need of cell therapy" refers to a subject diagnosed as having, or at risk of having or developing a disease associated with the failure of a naturally occurring cell or tissue type or a naturally occurring pluripotent and/or multipotent cell (e.g. stem cell).

In some embodiments, the methods described herein can be used to treat genetic disorders, e.g. Tay-Sachs or hemophilia, e.g. by administering allogeneic pluripotent cells and/or their progeny obtained as described herein.

In one aspect, described herein is a method of preparing a cell or tissue that is compatible with cell therapy to be administered to a subject, comprising: generating a pluripotent cell (or more pluripotent cell) from a cell according to the methods described herein, wherein the cell is an autologous cell or HLA-matched allogeneic cell. In some embodiments, the pluripotent cell (or more pluripotent cell) can be differentiated along a pre-defined cell lineage prior to administering the cell or tissue to the subject.

Pluripotent cells, e.g. pluripotent stem cells, generated according to the methods described herein can be used in cancer therapy. For example, high dose chemotherapy plus hematopoietic stem cell transplantation to regenerate the bone marrow hematopoietic system can benefit from the use of pluripotent cells generated as described herein.

Non-limiting examples of diseases associated with the failure of a naturally occurring cell or tissue type or a naturally occurring pluripotent and/or multipotent cell include aplastic anemia, Fanconi anemia, and paroxysmal nocturnal hemoglobinuria (PNH). Others include, for example: acute leukemias, including acute lymphoblastic leukemia (ALL), acute myelogenous leukemia (AML), acute biphenotypic leukemia and acute undifferentiated leukemia; chronic leukemias, including chronic myelogenous leukemia (CML), chronic lymphocytic leukemia (CLL), juvenile chronic myelogenous leukemia (JCML) and juvenile myelomonocytic leukemia (JMML); myeloproliferative disorders, including acute myelofibrosis, angiogenic myeloid metaplasia (myelofibrosis), polycythemia vera and essential thrombocythemia; lysosomal storage diseases, including mucopolysaccharidoses (MPS), Hurler's syndrome (MPS-IH), Scheie syndrome (MPS-IS), Hunter's syndrome (MPS-II), Sanfilippo syndrome (MPS-III), Morquio syndrome (MPS-IV), Maroteaux-Lamy Syndrome (MPS-VI), Sly syndrome, beta-glucuronidase deficiency (MPS-VII), adrenoleukodystrophy, mucolipidosis II (I-cell Disease), Krabbe disease, Gaucher's disease, Niemann-Pick disease, Wolman disease and metachromatic leukodystrophy; histiocytic disorders, including familial erythrophagocytic lymphohistiocytosis, histiocytosis-X and hemophagocytosis; phagocyte disorders, including Chediak-Higashi syndrome, chronic granulomatous disease, neutrophil actin deficiency and reticular dysgenesis; inherited platelet abnormalities, including amegakaryocytosis/congenital thrombocytopenia; plasma cell disorders, including multiple myeloma, plasma cell leukemia, and Waldenstrom's macroglobulinemia. Other malignancies treatable with stem cell therapies include but are not limited to breast cancer, Ewing sarcoma, neuroblastoma and renal cell carcinoma, among others. Also treatable with stem cell therapy are: lung disorders, including COPD and bronchial asthma; congenital immune disorders, including ataxia-telangiectasia, Kostmann syndrome, leukocyte adhesion deficiency, DiGeorge syndrome, bare lymphocyte syndrome, Omenn's syndrome, severe combined immunodeficiency (SCID), SCID with adenosine deaminase deficiency, absence of T & B cells SCID, absence of T cells, normal B cell SCID, common variable immunodeficiency and X-linked lymphoproliferative disorder; other inherited disorders, including Lesch-Nyhan syndrome, cartilage-hair hypoplasia, Glanzmann thrombasthenia, and osteopetrosis; neurological conditions, including acute and chronic stroke, traumatic brain injury, cerebral palsy, multiple sclerosis, amyotrophic lateral sclerosis and epilepsy; cardiac conditions, including atherosclerosis, congestive heart failure and myocardial infarction;

metabolic disorders, including diabetes; and ocular disorders including macular degeneration and optic atrophy. Such diseases or disorders can be treated either by administration of pluripotent cells themselves, permitting in vivo differentiation to the desired cell type with or without the administration of agents to promote the desired differentiation, and/or by administering pluripotent cells differentiated to, or at least partially differentiated towards the desired cell type in vitro. Methods of diagnosing such conditions are well known to medical practitioners of ordinary skill in the art. In some embodiments, the subject can be one who was treated with radiation therapy or other therapies which have ablated a population of cells or stem cells, e.g. the subject can be a subject with cancer whose bone marrow has been ablated by radiation therapy.

In some embodiments, pluripotent cells are administered to the subject. In some embodiments, an at least partially differentiated cell is administered to the subject. In some embodiments, the method of cell therapy can further comprise differentiating the pluripotent cell along a pre-defined cell lineage prior to administering the cell. Methods of differentiating stem cells along desired cell lineages are known in the art and examples are described herein.

In some embodiments, a composition comprising a pluripotent cell obtained according to the methods described herein or an at least partially differentiated cell which is the progeny of the pluripotent cell is administered to the subject.

In some embodiments, a composition comprising a pluripotent cell obtained according to the methods described herein, or an at least partially differentiated cell which is the progeny of the pluripotent cell, can optionally further comprise G-CSF, GM-CSF and/or M-CSF and/or can be administered to a subject who has or will be administered G-CSF, GM-CSF and/or M-CSF in a separate composition. Administration of G-CSF, GM-CSF and/or M-CSF can, e.g. induce a state of inflammation favorable to organ regeneration and removal of tissue debris, waste and buildup.

In some embodiments, administration of the pluripotent cells and/or their at least partially differentiated progeny can occur within a relatively short period of time following production of the pluripotent cell in culture according to the methods described herein (e.g. 1, 2, 5, 10, 24 or 48 hours after production). In some embodiments, administration of the at least partially differentiated progeny can occur within a relatively short period of time following differentiation of the pluripotent cell in culture according to the methods described herein (e.g. 1, 2, 5, 10, 24 or 48 hours after production). In some embodiments, the pluripotent cells and/or their at least partially differentiated progeny can be cryogenically preserved prior to administration.

In some aspects, the technology described herein relates to a composition comprising a pluripotent cell generated according to the methods described herein and/or the at least partially differentiated progeny of the pluripotent cell. In some embodiments, a pharmaceutical composition comprises a pluripotent cell generated according to the methods described herein and/or the at least partially differentiated progeny of the pluripotent cell, and optionally a pharmaceutically acceptable carrier. The compositions can further comprise at least one pharmaceutically acceptable excipient.

The pharmaceutical composition can include suitable excipients, or stabilizers, and can be, for example, solutions, suspensions, gels, or emulsions. Typically, the composition will contain from about 0.01 to 99 percent, preferably from about 5 to 95 percent of cells, together with the carrier. The cells, when combined with pharmaceutically or physiologically acceptable carriers, excipients, or stabilizer, can be administered parenterally, subcutaneously, by implantation or by injection. For most therapeutic purposes, the cells can be administered via injection as a solution or suspension in liquid form. The term "pharmaceutically acceptable carrier" refers to a carrier for administration of the pluripotent cell generated according to the methods described herein and/or the at least partially differentiated progeny of the pluripotent cell. Such carriers include, but are not limited to, saline, buffered saline, dextrose, water, glycerol, and combinations thereof. Each carrier must be "acceptable" in the sense of being compatible with the other ingredients of the formulation, for example the carrier does not decrease the impact of the agent on the subject. In other words, a carrier is pharmaceutically inert and compatible with live cells.

Suitable formulations also include aqueous and non-aqueous sterile injection solutions which can contain antioxidants, buffers, bacteriostats, bactericidal antibiotics and solutes which render the formulation isotonic with the bodily fluids of the intended recipient. Aqueous and non-aqueous sterile suspensions can include suspending agents and thickening agents. The formulations can be presented in unit-dose or multi-dose containers.

Examples of parenteral dosage forms include, but are not limited to, solutions ready for injection, suspensions ready for injection, and emulsions. Parenteral dosage forms can be prepared, e.g., using bioresorbable scaffold materials to hold pluripotent cells generated according to the methods described herein and/or the at least partially differentiated progeny of the pluripotent cell.

The term 'epigenetic modification' refers to the chemical marking of the genome. Epigenetic marks can include DNA methylation (imprints) as well as methylation and acetylation of proteins associated with DNA, such as histones. Parent-of-origin-specific gene expression (either from the maternal or paternal chromosome) is often observed in mammals and is due to epigenetic modifications. In the parental germlines, epigenetic modification can lead to stable gene silencing or activation.

As used herein, the term "administer" or "transplant" refers to the placement of cells into a subject by a method or route which results in at least partial localization of the cells at a desired site such that a desired effect is produced.

The pluripotent stem cells described herein, and/or their at least partially differentiated progeny, can be administered in any manner found appropriate by a clinician and can include local administration, e.g. by injection of a suspension of cells or, for example, by implantation of a preparation of cells deposited or grown on or within an implantable scaffold or support. Implantable scaffolds can include any of a number of degradable or resorbable polymers, or, for example, a silk scaffold, among others. Suitable routes for administration of a pharmaceutical composition comprising pluripotent stem cells described herein, and/or their at least partially differentiated progeny include but are not limited to local administration, e.g. intraperitoneal, parenteral, intracavity or subcutaneous administration. The phrases "parenteral administration" and "administered parenterally" as used herein, refer to modes of administration other than enteral and topical administration, usually by injection, and includes, without limitation, intraperitoneal, intradermal, subcutaneous injection and infusion. Administration can involve the use of needles, catheters and syringes suitable for injection, or surgical implantation. The use of a combination of delivery means and sites of delivery are contemplated to achieve the desired clinical effect.

The term 'epigenetic modification' refers to the chemical marking of the genome Epigenetic marks can include DNA methylation (imprints) as well as methylation and acetylation of proteins associated with DNA, such as histones. Parent-of-origin-specific gene expression (either from the maternal or paternal chromosome) is often observed in mammals and is due to epigenetic modifications. In the parental germlines, epigenetic modification can lead to stable gene silencing or activation.

In one embodiment, a therapeutically effective amount of pluripotent stem cells described herein, and/or their at least partially differentiated progeny is administered to a subject. A "therapeutically effective amount" is an amount of pluripotent stem cells described herein, and/or their at least partially differentiated progeny, sufficient to produce a measurable improvement in a symptom or marker of the condition being treated. Actual dosage levels of cells in a therapeutic composition can be varied so as to administer an amount of the cells that is effective to achieve the desired therapeutic response for a particular subject. The selected dosage level will depend upon a variety of factors including, but not limited to, the activity of the therapeutic composition, formulation, the route of administration, combination with other drugs or treatments, severity of the condition being treated, the physical condition of the subject, prior medical history of the subject being treated and the experience and judgment of the clinician or practitioner administering the therapy. Generally, the dose and administration scheduled should be sufficient to result in slowing, and preferably inhibiting progression of the condition and also preferably causing a decrease in one or more symptoms or markers of the condition. Determination and adjustment of a therapeutically effective dose, as well as evaluation of when and how to make such adjustments, are known to those of ordinary skill in the art of medicine.

The dosage of pluripotent stem cells described herein, and/or their at least partially differentiated progeny administered according to the methods described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to administer another dose of cells, increase or decrease dosage, discontinue treatment, resume treatment, or make other alteration to the treatment regimen. Where cells administered are expected to engraft and survive for medium to long term, repeat dosages can be necessary. However, administration can be repeated as necessary and as tolerated by the subject. The dosage should not be so large as to cause substantial adverse side effects. The dosage can also be adjusted by the individual physician in the event of any complication. Typically, however, the dosage can range from 100 to $1 \times 10^9$ pluripotent stem cells as described herein, and/or their at least partially differentiated progeny for an adult human, e.g. 100 to 10,000 cells, 1,000 to 100,000 cells, 10,000 to 1,000,000 cells, or 1,000,000 to $1 \times 10^9$ cells. Effective doses can be extrapolated from dose-response curves derived from, for example, animal model test bioassays or systems.

Therapeutic compositions comprising pluripotent stem cells described herein, and/or their at least partially differentiated progeny prepared as described herein are optionally tested in one or more appropriate in vitro and/or in vivo animal models of disease, such as a SCID mouse model, to confirm efficacy, evaluate in vivo growth of the transplanted cells, and to estimate dosages, according to methods well known in the art. In particular, dosages can be initially determined by activity, stability or other suitable measures of treatment vs. non-treatment (e.g., comparison of treated vs. untreated animal models), in a relevant assay. In determining the effective amount of pluripotent stem cells described herein, and/or their at least partially differentiated progeny, the physician evaluates, among other criteria, the growth and volume of the transplanted cells and progression of the condition being treated. The dosage can vary with the dosage form employed and the route of administration utilized.

With respect to the therapeutic methods described herein, it is not intended that the administration of pluripotent stem cells described herein, and/or their at least partially differentiated progeny be limited to a particular mode of administration, dosage, or frequency of dosing. All modes of administration are contemplated, including intramuscular, intravenous, intraperitoneal, intravesicular, intraarticular, intralesional, subcutaneous, or any other route sufficient to provide a dose adequate to treat the condition being treated.

In some embodiments, the methods described herein can be used to generate pluripotent cells in vivo, e.g. a cell present in a subject can be subjected to a stress as described herein such that acquires a pluripotent phenotype. Methods of applying the stresses described herein to cells in vivo are readily apparent, e.g. mild acid solutions can be introduced to a tissue via injection and/or direct application, temperatures can be altered by probes which can heat or cool the surrounding tissue or via the use of non-invasive methods, e.g. focus beam radiation. In vivo modulation of pluripotency can be used to, e.g. increase tissue regeneration or wound healing. Non-limiting examples can include the injection of a mild acid into an arthritic knee joint to induce knee joint cells (e.g. synovial or cartilage cells) to assume a pluripotent phenotype and generate new tissues. A further non-limiting example can include the treatment of a subject with a stroke or central nervous system injury (e.g. spinal cord injury). After inflammation has resolved, the cells adjacent to the injured area can be treated with a stress as described herein, generating pluripotent cells that can repopulate the damaged tissue and/or regenerate or repair the damaged tissue.

In a further non-limiting example, changes in epigenetic status (e.g. by treatment with a demethylase) can cause non-insulin secreting cells (e.g. alpha glugagon cells of the pancreas) to convert to insulin-secreting cells (e.g. beta cells). Accordingly, treating a non-insulin secreting cell (e.g. an alpha glugagon cell of the pancreas) in accordance with the methods described herein can result in the cell becoming an insulin-secreting cell, e.g. a beta-like cell, either in vivo or in vitro.

Further, it is contemplated that the pluripotent cells described herein can fuse with other cells (i.e. "recipient cells"), e.g. cells not treated according to the methods described herein, non-pluripotent cells, mature cells, malignant cells, and/or damaged cells. The fusion of the cells can result in an increased level of cellular repair enzyme expression and/or activity in the recipient cell as compared to prior to the fusion. This can increase the health and/or function of the recipient cell, e.g. by increasing repair of cellular damage, mutations, and/or modification of the epigenetic status of the recipient cell.

In some embodiments, by increasing the pluripotency of cells in vivo, the epigenetic markers (e.g. DNA methylation, demethylation, and/or hydroxymethylation status) of those cells can be modulated. Modulation of epigenetic markers has been implicated in, e.g. malignancy, arthritis, autoimmune disease, aging, etc and the treatment of such epigenetically-linked conditions in accordance with the methods described herein is contemplated.

In some embodiments, multiple tissues can be treated in vivo at the same time, e.g. a mildly acidic state could be induced in multiple organs, e.g. successively or in synchrony (e.g. brain, heart, liver, lung, and/or thyroid) to treat widespread damage or aging.

It is further contemplated that the in vivo treatment of cells as described herein can be combined with the administration of pluripotent cells and/or the at least partially differentiated progeny thereof which have been produced as described herein.

It is contemplated herein that the methods described herein can be used to treat, e.g. a fetus or embryo in utero.

Efficacy of treatment can be assessed, for example by measuring a marker, indicator, symptom or incidence of, the condition being treated as described herein or any other measurable parameter appropriate, e.g. number of pluripotent cell progeny. It is well within the ability of one skilled in the art to monitor efficacy of treatment or prevention by measuring any one of such parameters, or any combination of parameters.

Effective treatment is evident when there is a statistically significant improvement in one or more markers, indicators, or symptoms of the condition being treated, or by a failure to worsen or to develop symptoms where they would otherwise be anticipated. As an example, a favorable change of at least about 10% in a measurable parameter of a condition, and preferably at least about 20%, about 30%, about 40%, about 50% or more can be indicative of effective treatment. Efficacy for pluripotent cells generated according to the methods described herein and/or the at least partially differentiated progeny of the pluripotent cell can also be judged using an experimental animal model known in the art for a condition described herein. When using an experimental animal model, efficacy of treatment is evidenced when a statistically significant change in a marker is observed, e.g. the number of hematopoietic cells present in a mouse following bone marrow ablation and treatment with pluripotent cells as described herein.

In one aspect, described herein is a method of producing a pluripotent cell capable of differentiating into a placental cell, the method comprising culturing a pluripotent cell obtained according to the methods described herein in the presence of FGF4. In some embodiments, the pluripotent cell is capable of differentiating into an embryonic stem cell. In some embodiments, the concentration of FGF4 is from about 1 nM to about 1 uM. In some embodiments, the concentration of FGF4 is from 1 nM to 1 uM. In some embodiments, the concentration of FGF4 is from about 5 nM to about 500 nM. In some embodiments, the concentration of FGF4 is from about 10 nM to about 100 nM.

In some aspects, the technology described herein relates to a system for generating a pluripotent cell from a cell, comprising removing a portion of the cytoplasm and/or mitochondria from the cell.

A system for generating a pluripotent cell from a cell, according to the methods described herein, can comprise a container in which the cells are subjected to stress. The container can be suitable for culture of somatic and/or pluripotent cells, as for example, when cells are cultured for days or longer under low oxygen conditions in order to reduce the amount of cytoplasm and/or mitochondria according to the methods described herein. Alternatively, the container can be suitable for stressing the cells, but not for culturing the cells, as for example, when cells are triturated in a device having a narrow aperture for a limited period, e.g. less than 1 hour. A container can be, for example, a vessel, a tube, a microfluidics device, a pipette, a bioreactor, or a cell culture dish. A container can be maintained in an environment that provides conditions suitable for the culture of somatic and/or pluripotent cells (e.g. contained within an incubator) or in an environment that provides conditions which will cause environmental stress on the cell (e.g. contained within an incubator providing a low oxygen content environment). A container can be configured to provide 1 or more of the environmental stresses described above herein, e.g. 1 stress, 2 stresses, 3 stresses, or more. Containers suitable for manipulation and/or culturing somatic and/or pluripotent cells are well known to one of ordinary skill in the art and are available commercially (e.g. Cat No CLS430597 Sigma-Aldrich; St. Louis, MO). In some embodiments, the container is a microfluidics device. In some embodiments, the container is a cell culture dish, flask, or plate.

In some embodiments, the system can further comprise a means for selecting pluripotent cells, e.g. the system can comprise a FACS system which can select cells expressing a pluripotency marker (e.g. Oct4-GFP) or select by size as described above herein. Methods and devices for selection of cells are well known to one of ordinary skill in the art and are available commercially, e.g. BD FACSARIA SORP™ coupled with BD LSRII™ and BD FACSDIVA™ Software (Cat No. 643629) produced by BD Biosciences; Franklin Lakes, NJ.

In some embodiments, cells which are not present in a tissue are provided to the system. In some embodiments, tissues are provided to the system and the system further comprises a means of isolating one or more types of cells. By way of non-limiting example, the system can comprise a tissue homogenizer. Tissue homogenizers and methods of using them are known in the art and are commercially available (e.g. FASTH21™, Cat No. 21-82041 Omni International; Kennesaw, GA). Alternatively, the system can comprise a centrifuge to process blood or fluid samples.

In some embodiments, the system can be automated. Methods of automating cell isolation, cell culture, and selection devices are known in the art and are commercially available. For example, the FASTH21™ Tissue Homogenizer (Cat No. 21-82041 Omni International; Kennesaw, GA) and the BD FACSARIA SORP™.

In some embodiments, the system can be sterile, e.g. it can be operated in a sterile environment or the system can be operated as a closed, sterile system.

In one aspect, described herein is a method of increasing the self-renewal ability of a pluripotent cell, the method comprising culturing the cell in the presence of adrenocorticotropic hormone (ACTH), 2i or 3i medium. As used herein, "self-renewal ability" refers to the length of time a cell can be cultured and passaged in vitro, e.g. the number of passages a cell and it's progeny can be subjected to and continue to produce viable cells. The cell which is caused to have an increased self-renewal ability according to the method described herein can be, e.g. a totipotent cell and/or a cell generated by exposing it to stress as described elsewhere herein.

In some embodiments, culturing in the presence of ACTH can comprise culturing the cell in a cell medium comprising from about 0.1 μM to about 1,000 μM, e.g. from about 0.1 μM to about 100 μM, from about 0.1 μM to about 10 μM, or about 10 μM. In some embodiments, culturing the cell in the presence of ACTH can comprise culturing the cell in LIF medium comprising ACTH. LIF, ACTH, 2i and 3i are commercially available and well known in the art, e.g.

ACTH can be purchased from Sigma-Aldrich (Cat No. A0673; St. Louis, MO) and LIF media can be purchased from Millipore (e.g. Cat Nos ESG1107; Billerica, MA), and 3i can be purchased from Stem Cells Inc. (e.g. as "iSTEM Stem Cell Culture Medium, Cat No. SCS-SF-ES-01; Newark, CA).

In some embodiments, the culturing step can proceed for at least 3 days, e.g. at least 3 days, at least 4 days, at least 5 days, at least 6 days, at least 7 days, or longer. After the culturing step, the cells can be maintained under conditions suitable for maintaining pluripotent cells as described elsewhere herein.

In some embodiments, after the culturing step, the cell can express a detectable and/or increased level of a stem cell marker. Stem cell markers and methods of detecting them are described elsewhere herein. In some embodiments, the stem cell marker can be selected from the group consisting of Oct3/4; Nanog; Rex1; Klf4; Sox2; Klf2; Esrr-beta; Tbx3; and Klf5.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

EXAMPLES

Example 1

All organisms possess a primitive survival instinct. When plants are subjected to significant external stresses they activate a mechanism to survive that causes dedifferentiation of cells and enables regeneration of the injured area or the entire organism. While such mechanisms appear to be essential for lower organisms to survive extreme environmental changes, they have yet to be documented in mammals.

The inventors hypothesized that physical stress may cause mature mammalian cells to revert to a stem cell state, similar to that seen in plants and lower organisms. To examine this hypothesis, mature cells procured from seven adult somatic tissues were studied. To first focus on which physical stresses might be most effective in altering mature cells to revert to a less mature state, CD45 positive lymphocytes harvested from Oct4-GFP mice were studied. Cells from these mice provide a readout of reversion to a stem cell phenotype when the stem cell specific Oct4 promoter is activated. The mature, fully differentiated cells were exposed to several significant external stimuli.

For example, CD45 positive lymphocytes were exposed to low pH solution to provide a strong chemical stress. Within 3 days of exposure, GFP expressing cells were observed, and within 5 days, spherical colonies composed of GFP expressing cells were observed. Cells generated in this manner were referred to in this Example as Stress Altered Stem Cells (SASCs or SACs). SACs can also be referred to as rejuvenated stem cells (RSCs) or animal callus cells (ACCs). SACs expressed several markers normally associated with embryonic stem cells. SACs exhibited a differentiation potency equivalent to ES cells, contributed to the generation of chimera mice and were capable of generating whole fetuses when injected into 4N blastocysts. Cells generated in this manner initially showed low mitochondrial activity and other conditions normally associated with the induction of cell based injury defense mechanisms. They then exhibited demethylation of the Oct4 and Nanog gene promoters. The reprogramming of stress altered cells appeared to be induced via mesenchymal-epithelial transition. The findings are consistent with descriptions of cells contained in the plant callus, in response to injury (external stimuli). A plant callus is formed from a stress induced conversion of cells to pluripotent plant stem cells, capable of forming clonal bodies. Such a spherical colony, generated from mature fully differentiated somatic mammalian cells in response to significant external stimuli, is referred to herein as an Animal Callus, and to the stress altered cells contained in such a colony or callus, as "Animal Callus Cells" (ACCs) or SACs.

Thus, significant physical and chemical stresses caused normal mature adult cells to be reprogrammed to pluripotent stem cells capable of embryogenesis. While not wishing to be bound by theory, the mechanism of reprogramming appears to include the induction of a cellular survival and repair process normally seen in response to injury. It is demonstrated herein that mammalian cells possess a survival mechanism very similar to that of plants, to revert to reprogrammed state in response to significant stressful external stimuli.

Various types of cells have reportedly been reprogrammed to a pluripotent stem cell state through induction or forced expression of specific genes[1-5]. It is also believed that damage to cells as a result of exposure to irritants, such as burns, chemical injury, trauma and radiation, may alter normal cells to become cancer cells.

Introduction

All organisms appear to have a common instinct to survive injury related to stressful stimuli by adapting themselves to the environment and regenerating their bodies. In plants, ontogenesis is observed not only in zygotes but also in fully differentiated cells and immature pollen. In vertebrates, newts are capable of regenerating several anatomical structures and organs, including their limbs[1]. Of particular note is that the remarkable regenerative capacity demonstrated by both plants and newts is induced by external stimuli, which cause cellular dedifferentiation of previously fully differentiated somatic cells. While billions of years have passed from the earliest form of life, and different organisms have evolved in unique ways, this survival instinct may be inherited from a common ancestor to modern-era organisms. Although terminally differentiated mammalian cells are normally believed to be incapable of reversing the differentiation process, mammals may retain a previously unappreciated program to escape death in response to drastic environmental changes.

The plant callus, a mass of proliferating cells formed in response to external stimuli, such as wounding, which can be stimulated in culture by the plant hormones[2]. The callus contains reprogrammed somatic cells, referred to as callus cells, each of which is capable of clonally regenerating the entire body. Callus cells are not inherent in plants, but are generated from somatic cells in response to external stimuli. Although recent studies demonstrated that mammalian somatic cells can be reprogrammed by exogenous processes, such as gene induction[3-7], reprogramming of mammalian somatic cells in response to external physical and or chemical stimuli, in a manner that parallels plants, has not been reported. Interestingly, it is believed that extreme external stimuli, such as exposure to irritants, including burns, chemical injury, trauma and radiation, may alter normal somatic cells to become cancer cells. Such experiences seem to indicate that external stimuli will result in mammalian cellular change.

In this study, it was hypothesized that mammalian cells retain a mechanism to survive exposure to significant external stress, in the same manner as plants. This report presents evidence that application of significant physical and chemical stimuli can cause reprogramming of mature, fully differentiated mammalian somatic cells, procured from various tissues, and that such stress altered cells are capable of forming an animal callus containing "animal callus cells", which can regenerate the clonal body.

Results

Figure 5A:
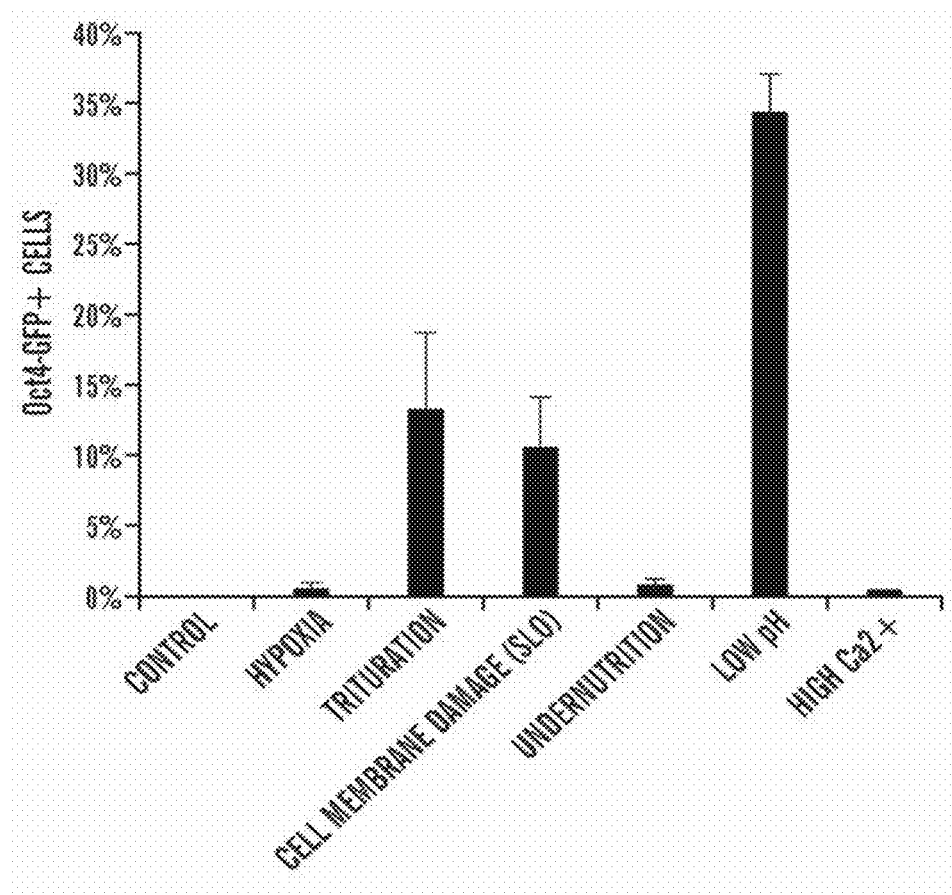
FIGS. 5A-5C experiments with ACC-generating conditions.

Significant physical and chemical stimuli applied to mature somatic cells. Since the embryonic transcription factor Oct4 is thought to be crucial in regulation of the pluripotent status of cells, the initial strategy was to identify which external stimuli most efficiently altered mature cells to become reprogrammed to express Oct4. CD45 positive hematopoietic lineage cells were first studied in order to avoid contamination with undifferentiated cells. CD45 positive cells harvested from spleens procured from Oct4-GFP (GOF) mice[8], were exposed to various significant physical and chemical stimuli. The exposures included: osmotic pressure treatment, treatment with significant mechanical trituration, exposure to low pH, application of cell membrane damage using streptolysin O (SLO), exposure to under nutrition and exposure to hypoxia and high $Ca^{2+}$ concentration. Next, GFP expressing cells were identified, sorted and collected using FACS. Gene expression of Oct4 was confirmed by R-T PCR. Exposure to each of the applied stimuli resulted in reprogramming of the mature cells to express GFP to some degree (FIG. 5A). Exposure of the mature cells to the chemical stress of low pH and the physical stress of significant mechanical trituration appeared to be the most effective treatments in altering mature cells to express Oct4.

Figure 5B:
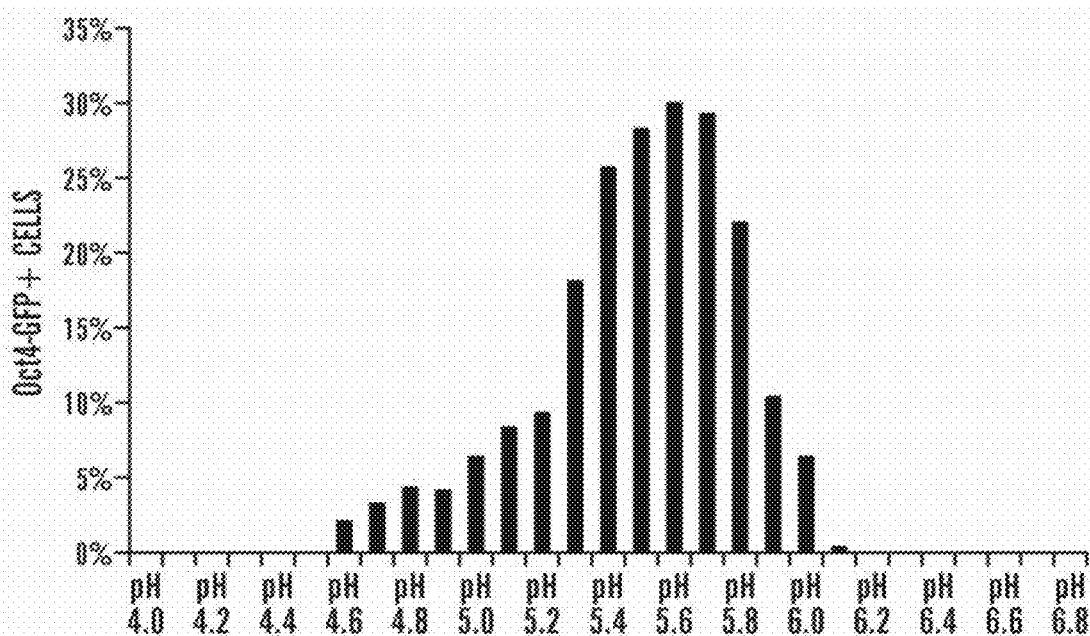

To determine the optimal pH for inducing conversion to Oct4 expressing cells, CD45 positive cells were exposed to solutions of varying acidity, from pH 4.0 to pH 6.8. At 3 days after exposure to an acidic solution, GFP expression of cells was analyzed using FACS. An acid solution with a pH 5.4-5.6 most efficiently altered cells to express GFP (FIG. 5B). Consequently, exposure to low pH was focused upon as the stress treatment of choice for the remainder of the study.

Figure 5C:
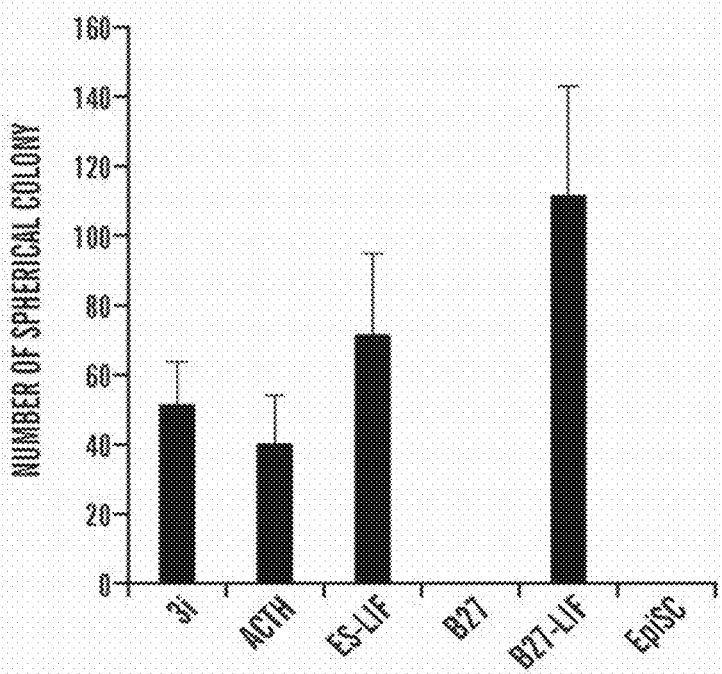

The optimum culture conditions for maintaining stress altered Oct4 expressing cells were then determined. Several previously described culture media, including: ES establishment culture medium, 3i[9] and ACTH[10], ES culture condition, ES-LIF[11], embryonic neural stem cell culture condition, B27-LIF[12], and EpiSCs culture condition[13], were studied. Cells were plated into each medium, and GFP expressed colonies were counted (FIG. 5C). The medium B27-LIF appeared to be the most effective in generating GFP expressing spherical colonies. Therefore B27-LIF medium was utilized for culture of the treated cells.

Figure 1B:
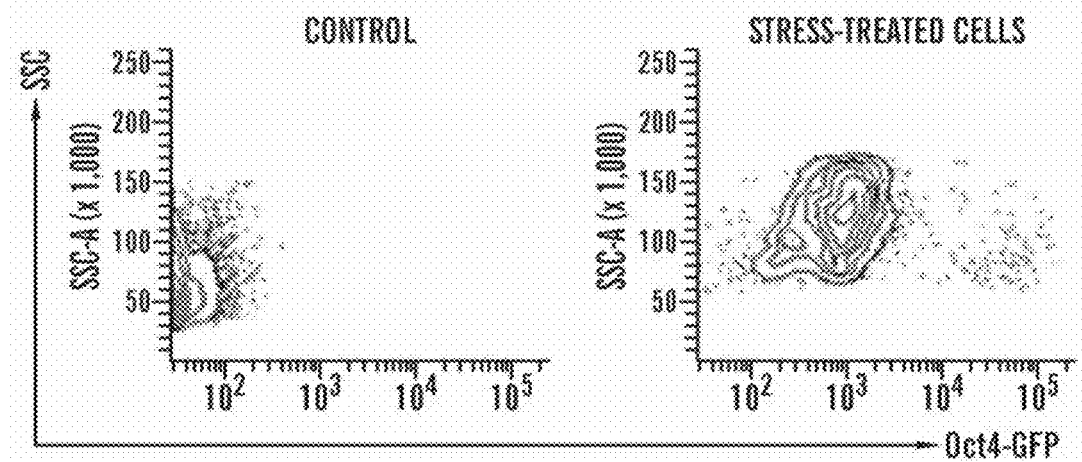
Figure 1C:
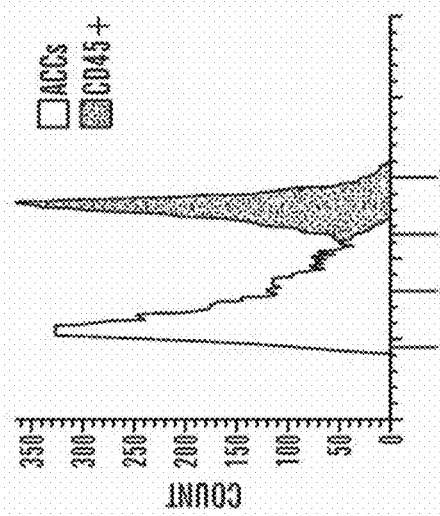

Stress treated CD45 positive cells were cultured in B27-LIF medium, and within 5 days, GFP expressing spherical colonies were observed while no GFP expressing colonies were observed in the untreated control (FIG. 1A). Spherical colonies grew to approximately 70 μm in diameter over the first 7 days, and spherical colonies could be maintained for another 7 days in that culture condition. The configuration of the colonies was slightly baroque, appearing more similar in shape to the callus seen in botany, rather than spheres. A cell colony generated by stress treatment was therefore referred to as an Animal Callus (AC). Cultured cells were dissociated and population analysis was then performed using FACS. The analysis revealed that the application of certain significant stimuli resulted in the generation of stress altered cells, now referred to as Animal Callus Cells (ACCs), that did not previously exist in the CD45 positive cell populations (FIG. 1B). The phenotypic change of CD45 positive cells as a result stress treatment was observed at the single cell level. While CD45 positive cells did not express GFP, ACCs expressed GFP associated with a diminished expression of CD45 (data not shown). Examination of single cells revealed that the cell size of treated cells appeared smaller than untreated cells. Therefore, cell size of ACCs population was analyzed by FACS. The cell size of ACCs was quite small, with 80% of cells being less than 8 μm in diameter (FIG. 1C).

Figure 1D:
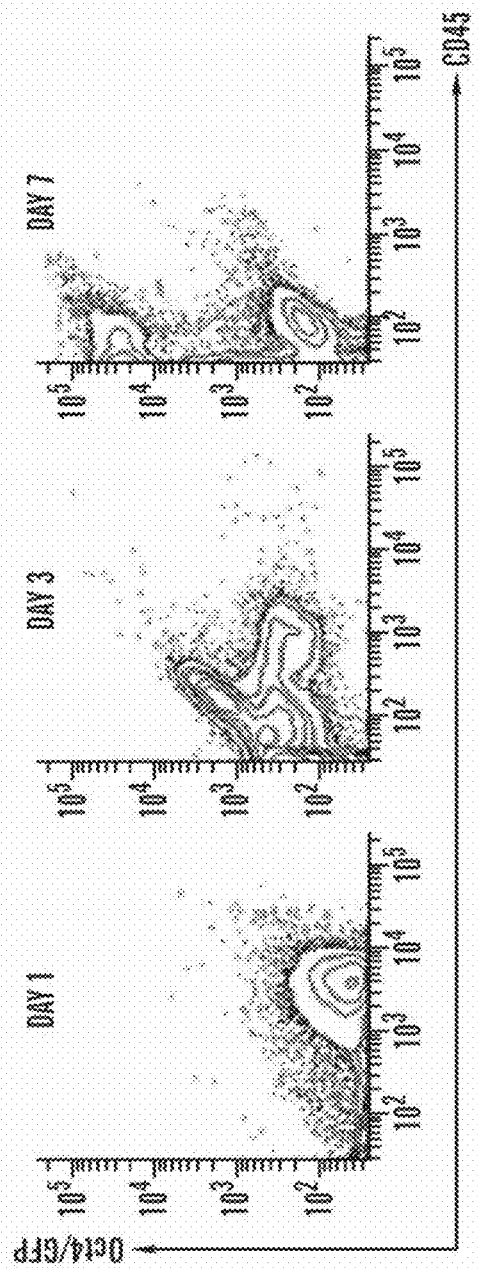

To examine chronological phenotypic change associated with CD45 diminution and Oct4 expression, stress treated CD45 positive cells were analyzed at day 1, day 3 and day 7. At day 1, most of cells still expressed CD45, but not Oct4. At day 3, marker expression transitioned to reveal CD45 negative cells or CD45 negative/Oct4positive (dim) cells. At day 7, CD45 expression disappeared, and Oct4 expressing cells were observed (FIG. 1D). Notably, during the first 7 days of culture, the number of PI positive cells (dead cells) gradually increased (Data not shown), which suggested that the stress treatment and the culture condition gradually changed the character of cells and selected for successfully altered cells, which expressed Oct4.

Figure 2A:
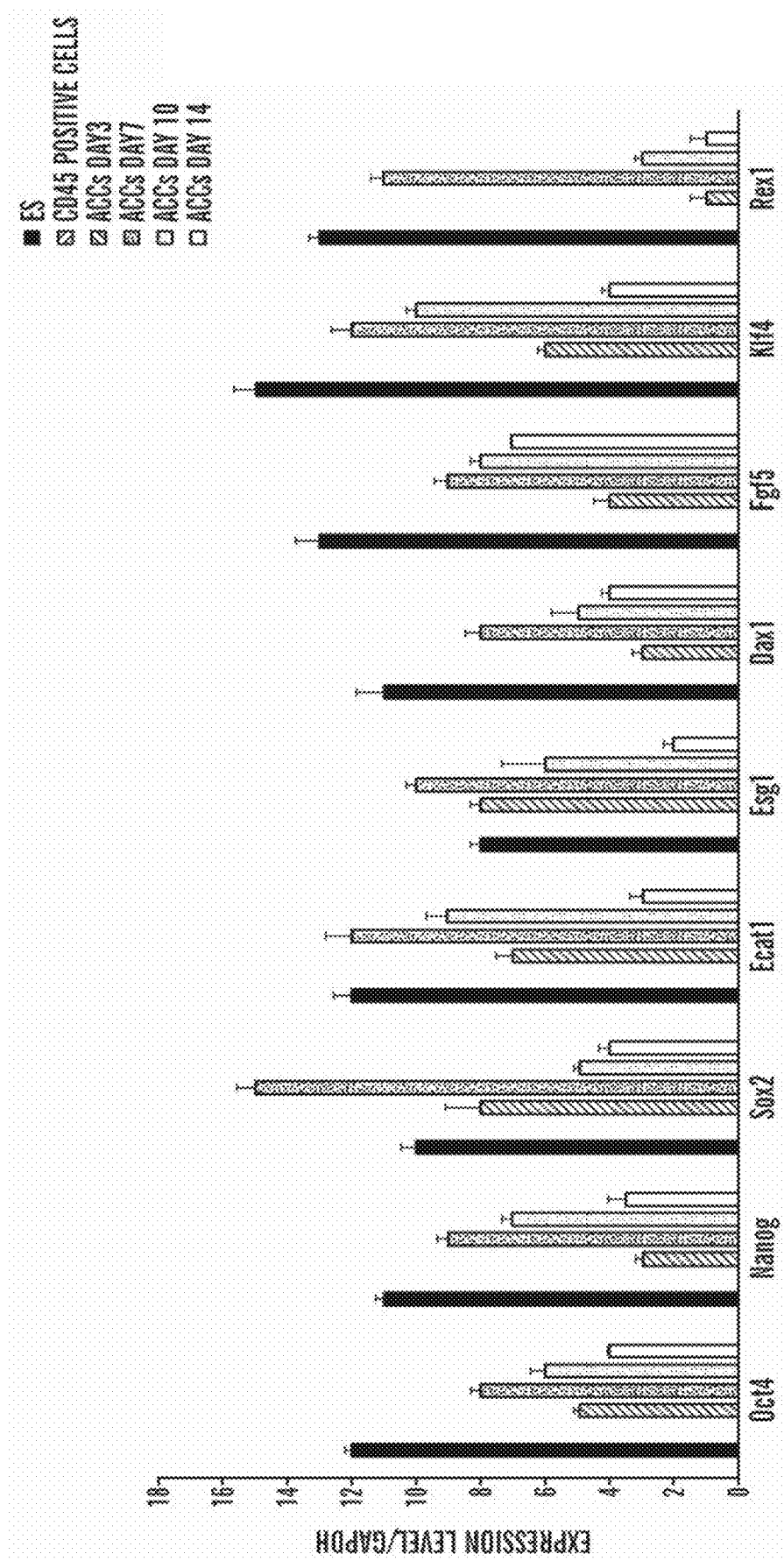
FIGS. 2A-2B depict characterization of animal callus cells (ACCs).
Figure 2B:
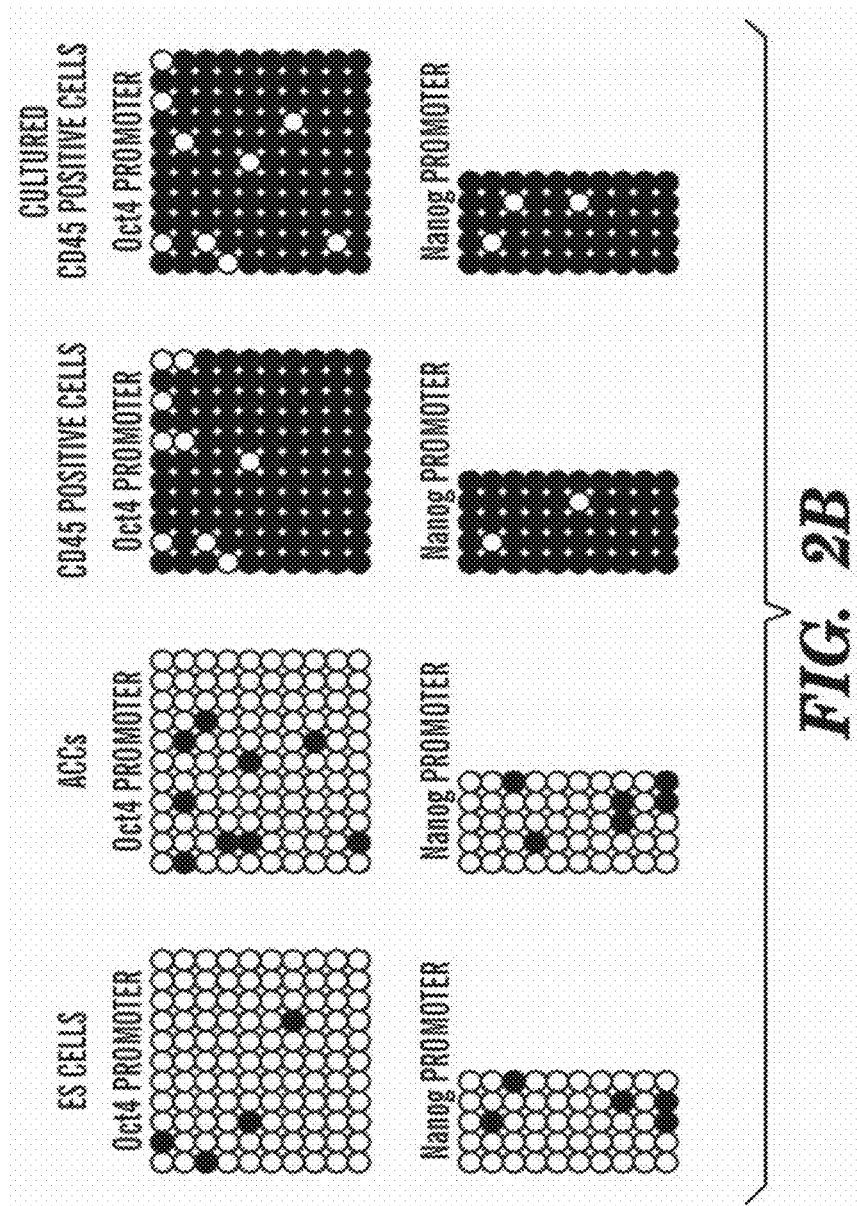

Characterization of ACCs. To confirm the reprogramming of somatic cells as a result of exposure to external stimuli, early embryogenesis marker gene expression of ACCs was investigated. As a positive control of early embryogenesis, ES cells were utilized in following experiments. Marker expression and DNA methylation was characterized as follows Immunofluorescence staining at day 7, showed that spherical colonies containing ACCs, uniformly expressed pluripotent cell markers, E-cadherin antigen, Nanog, SSEA- 1, PCAM-1, and AP, and were positive for Oct4-GFP (data not shown). Gene expression analysis showed that ACCs and ES cells, but not primary CD45 positive cells, expressed comparable levels of Oct4, Nanog, Sox2, Ecat1, Esg1, Dax1, Fgf5, Klf4 and Rex1 genes (FIG. 2A). Gene expression of ES specific genes in ACCs reached a peak at day 7 (FIG. 2A). Bisulfite sequencing was performed to determine the methylation status of Oct4 and Nanog gene promoters in ACCs. Native lymphocytes and cultured lymphocyte control samples displayed extensive methylation at both promoters, whereas ACCs showed widespread demethylation of these regions similar to that seen in ES cells (FIG. 2B). Thus, it is demonstrated that mammalian somatic cells were reprogrammed by external stress.

Figure 6A:
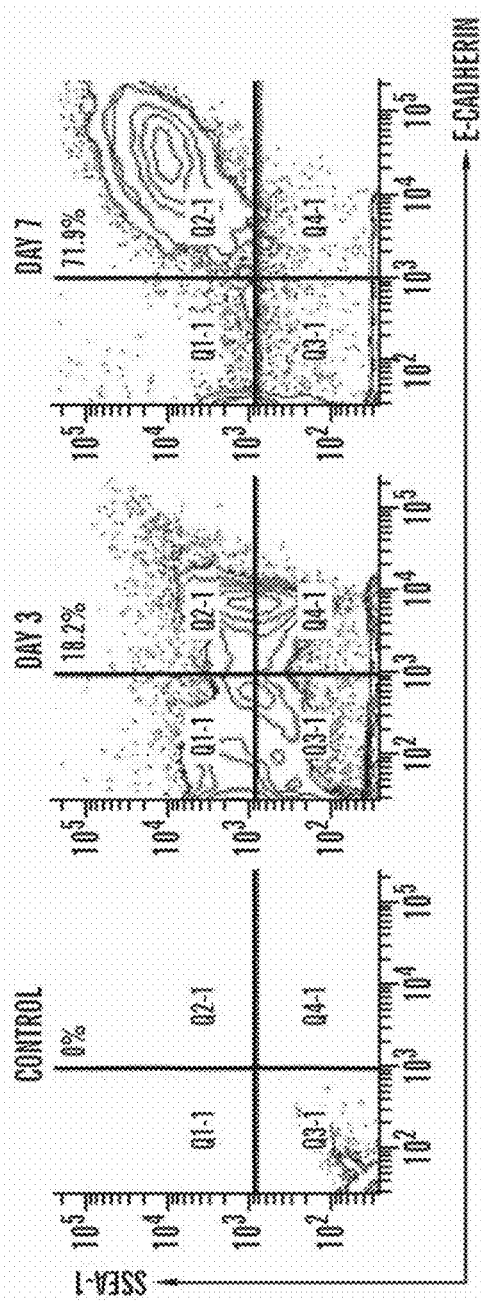
FIGS. 6A-6B depict ACCs generation from CD45 positive cells derived from ICR mice.
Figure 6B:
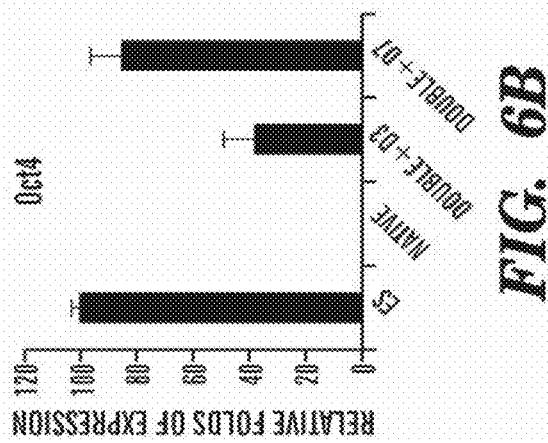

To confirm that the Oct4 gene expression resulted from stress treatment of mature cells not only in GOF mice but also in wild type mice, CD45 positive lymphocytes were harvested from spleens procured from ICR mice. The lymphocytes were then exposed to the stress treatment and chronologically analyzed until day 7 using FACS. A SSEA-1 positive/E-cadherin positive cell population was seen in the stress treated group, while SSEA-1/E-cadherin expression was not observed in the non-stress treated control group (FIG. 6A). Those double positive cells expressed Oct4 gene expression, which was confirmed by R-T PCR (FIG. 6B). These results demonstrated that as a result of the stress treatment, ACCs, Oct4 positive and pluripotent marker expressing cells, were generated from CD45 positive cells irrespective of mouse strain.

These results imply that the mature fully differentiated adult somatic cells reverted to "stemness" as a result of the stress treatment.

To assess the stemness of ACCs, their self-renewal potency and their differentiation potency were examined. To study their self-renewal potency, ACCs colonies derived from previously mature CD45 positive lymphocytes were dissociated into single cells, and plated into 96 well plates, with one cell per well in an effort to generate clonally derived populations. Ten days after plating, spherical colonies were seen in 4 of the 96 wells. The dividing time of ACCs varied from well to well. Some divided in 12-16 h and others divided in 30-34 h. ACCs were passaged at least 5 times, with continued expression of Oct4 observed. Consequently, ACCs demonstrated a potential for self-renewal, and the potential to differentiate into cells from all three germ layers in vitro.

ACs derived from mature GOF lymphocytes were again dissociated into single cells, sorted to contain only a population of cells that expressed GFP and then cultured in differentiation media. At 14-21 days after plating, cells expressed the ectoderm marker, βIII-tubulin and GFAP, the mesoderm marker, α-smooth muscle actin, and the endoderm marker, α-fetoprotein and Cytokeratin 7 (data not shown). Thus, ACCs differentiated into cells representative of the three germ layers in vitro.

Figure 7A:
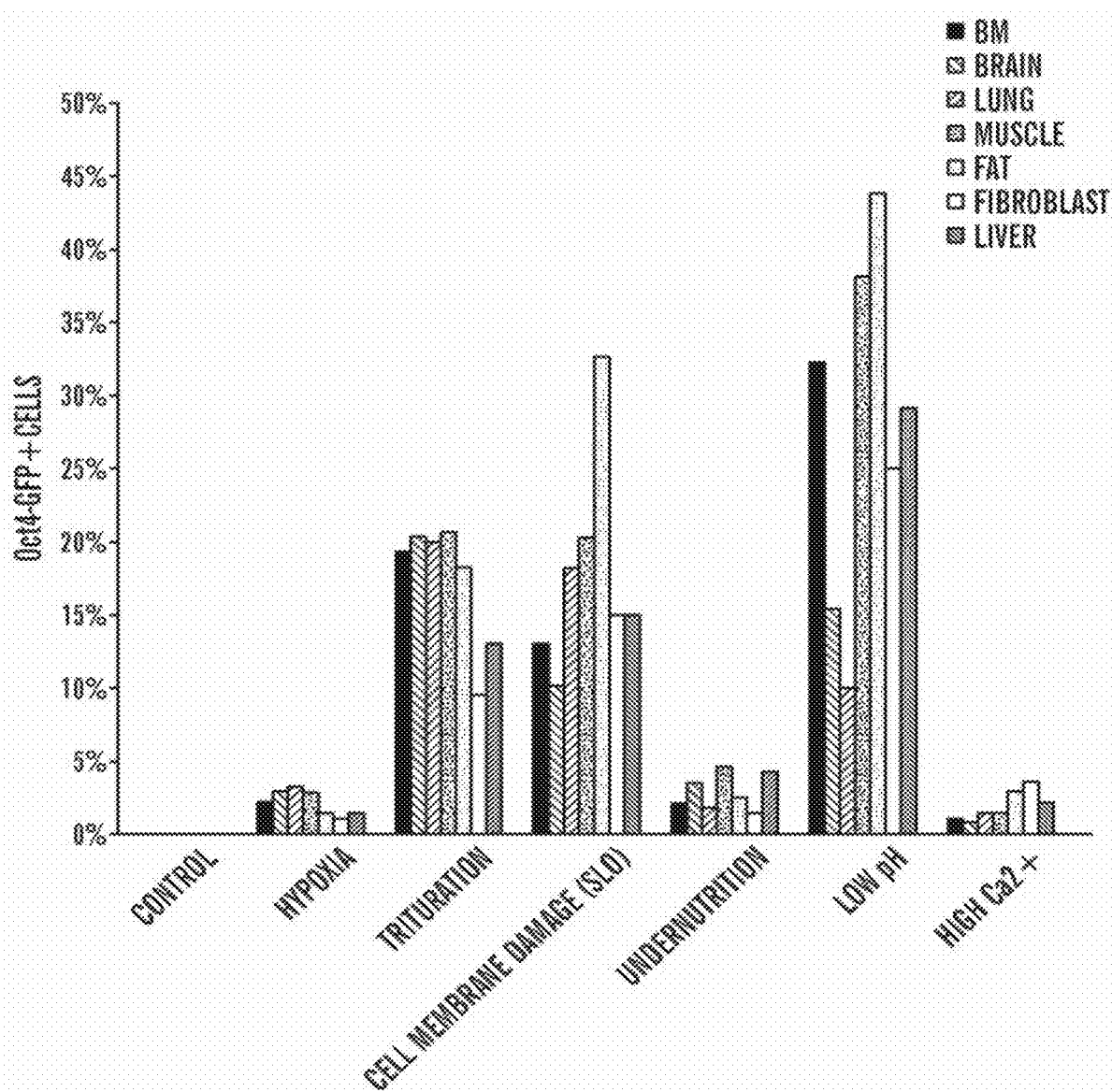
FIGS. 7A-7B depict ACC generation from various tissues derived from GOF mice.
Figure 7B:
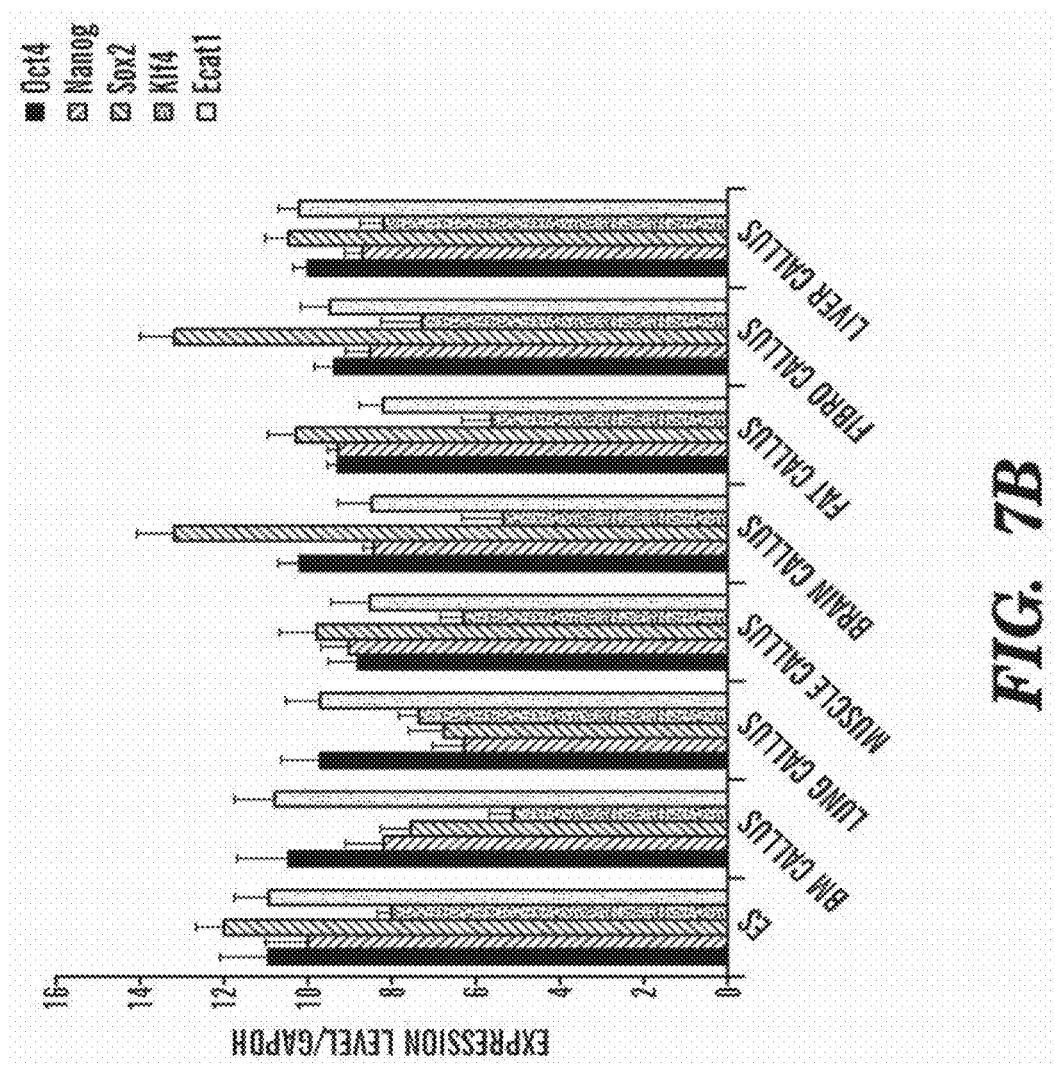

Stress alteration of mature somatic cells procured from various adult tissues. To examine whether ACCs could be generated not only mature lymphocytes but also other types of somatic cells, brain, skin, muscle, fat, bone marrow, lung and liver were harvested from Oct4-GFP (GOF) mice[8]. Cells were isolated from the tissue samples, dissociated into single cells, and treated with different physical and or chemical stress conditions. The efficiency of the process to alter the cells differed as a function of both the source of cells and the stress condition(s) to which the cells were exposed (FIG. 7A). The ability of stress to alter mature cells to express Oct4, differed depending on the derivation of cells, but stress was able to alter cells to express Oct4 to some degree in mature cells derived from all three germ layers (FIG. 7A). ACC colonies derived from any mature tissue expressed pluripotent markers, E-cadherin, Nanog, PCAM-1 and AP (data not shown), and ES specific marker genes (FIG. 7B). Significant physical and chemical stresses altered mature somatic cells to revert to a stem cell state, despite of the source of tissues and derivation of the germ layers.

Cellular modification in the initial phase of ACCs generation. These results demonstrate that strong physical and chemical stimuli result in reprogramming of somatic cells. Stress treated lymphocytes were observed to form an AC within 5 days. It was hypothesized that drastic change of molecular events occurred as a result of the stress exposure. Studies were therefore focused on the initial phase of the reprogramming, which was the during the first 7 days after the exposure to the stimuli.

Figure 3A:
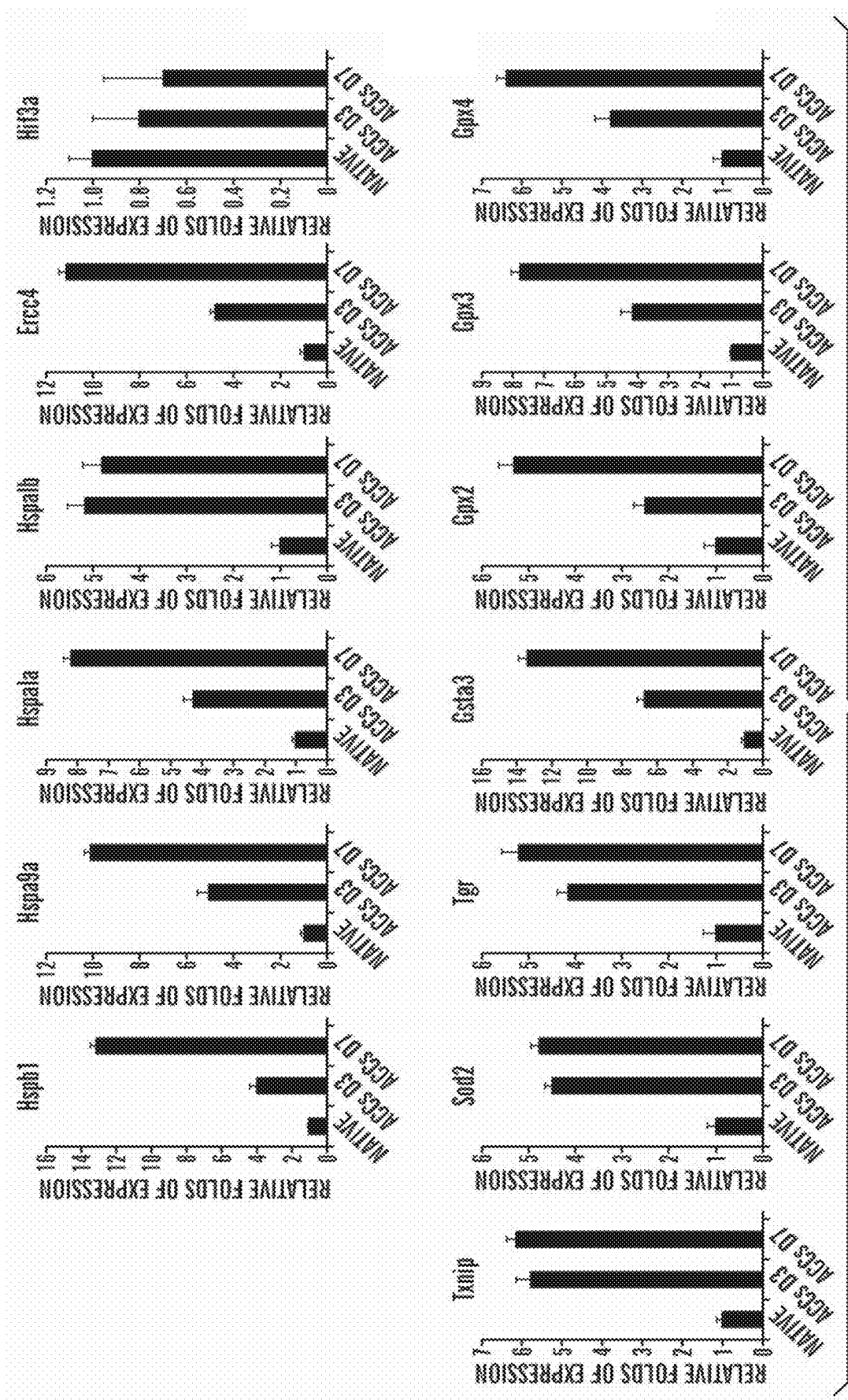
FIGS. 3A-3D depict cellular modifications after stress treatment.
Figure 8:
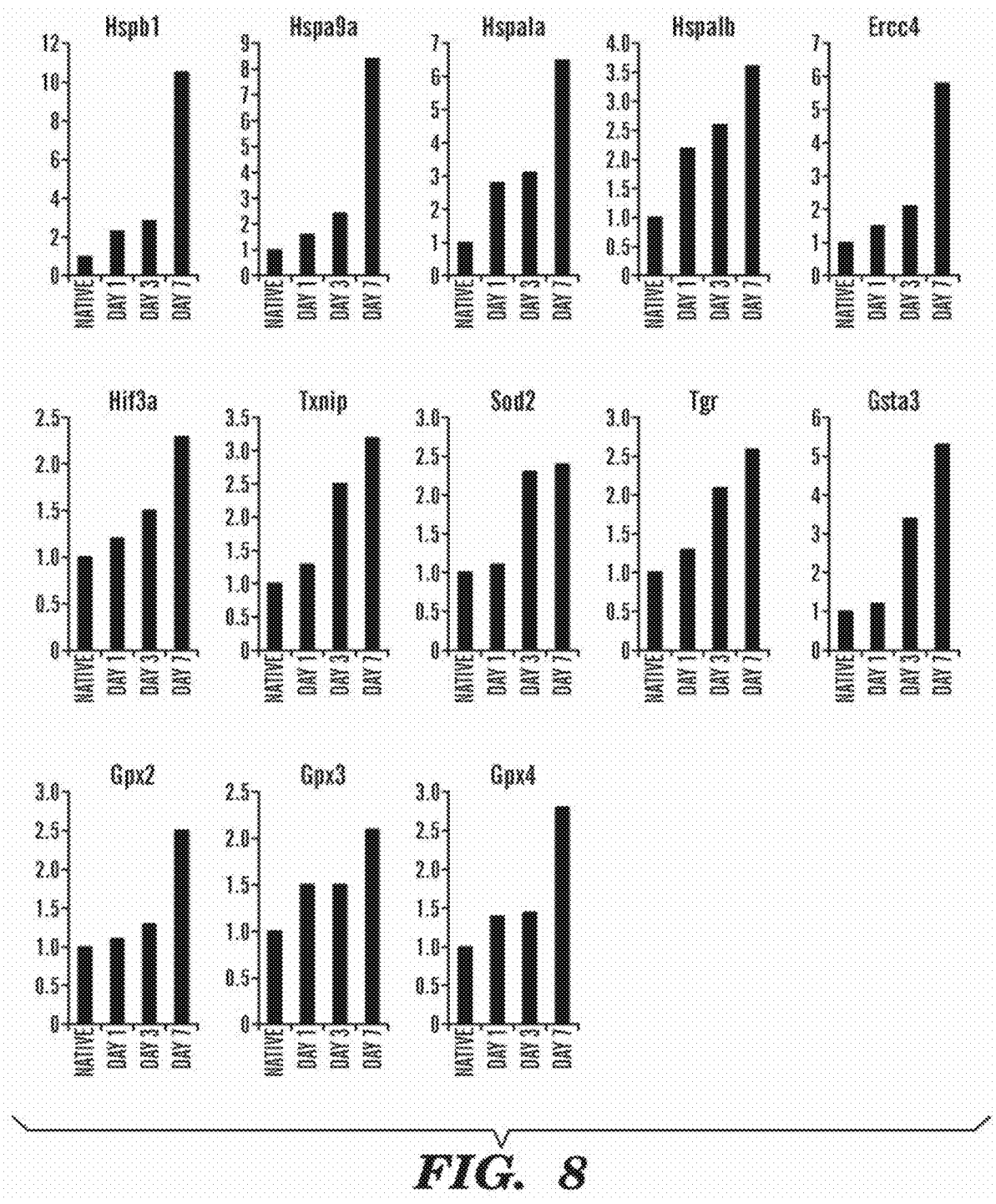
FIG. 8 depicts relative gene expression of stress defense genes during the first 7 days. After stress treatment, cells were collected at day 1, 3 and 7, and gene expression was compared with native CD45 positive cells. Blue graphs indicate the gene expressions of heat shock proteins. Green graph indicates DNA repair gene expression. Red graphs indicate the gene expression of redox genes. Y-axis indicates relative folds of expression.

Because ACCs survived after the significant stress exposure, it was speculated that survival mechanisms normally turned on to repair cellular damage were induced during the ACCs generation. First the expression of a number of candidate genes involved in cellular response to stress and DNA repair 14 was compared in in native CD45 positive cells and stress-treated CD45 positive cells at day 1, day 3 and day 7. Cellular response gene expression was already observed at day 1, and those genes were up-regulated over 7 days when the mixtures of ACC generating cells and other cells were analyzed (FIG. 8). Because the up-regulation of cellular response genes was correlated with ACCs generation, ACCs at day 3 and day 7 were sorted, and gene expression was analyzed. With the exception of Hif3a, all candidate genes were up-regulated to various degrees during the ACCs generation (FIG. 3A). Four heat shock genes and one DNA repair gene were found to be up-regulated during the ACCs generation. Furthermore, seven of the up-regulated genes are known to be directly involved in the regulation of the cellular redox state. These results suggested that the self-repair or self-defense potency was induced during the ACCs generation.

Figure 3B:
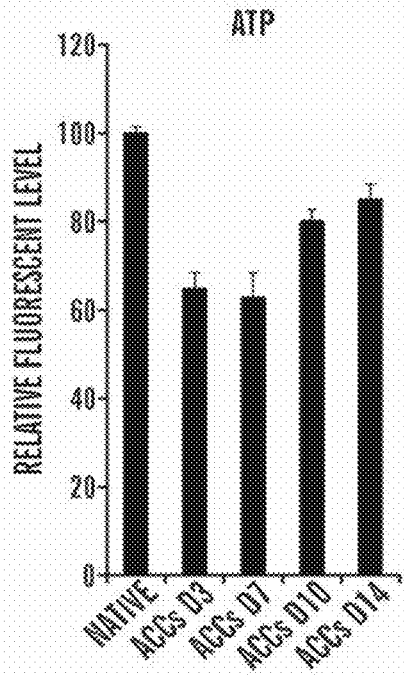
Figure 3C:
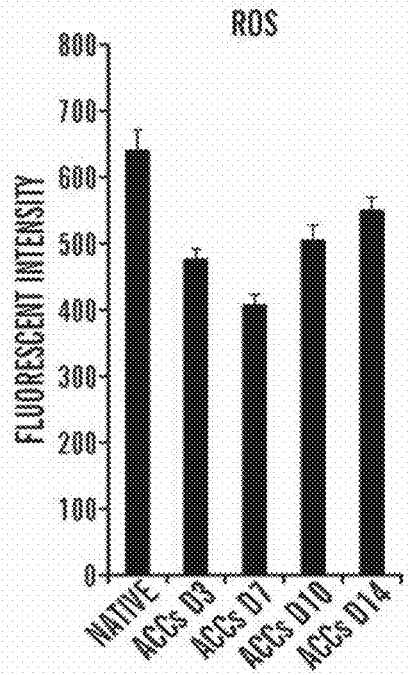
Figure 3D:
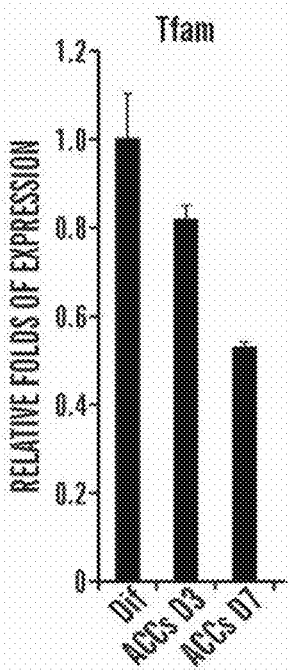
Figure 3D:
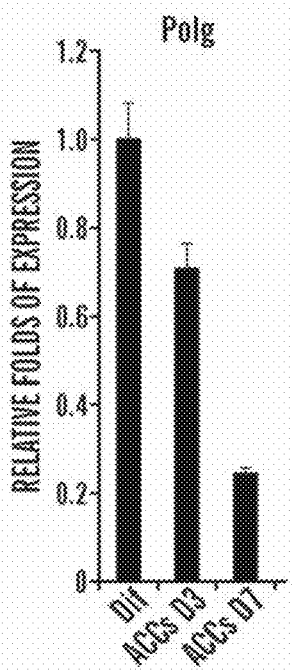
Figure 3D:
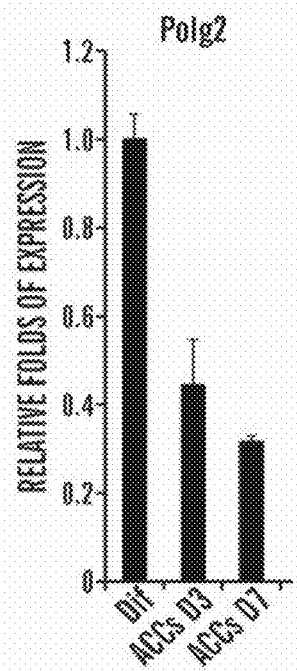

Since ACCs exhibited the up-regulation of cellular redox associated genes, the mitochondrial function of ACCs was next examined. Mitochondria are organelles responsible for production of the vast majority of ATP via the redox reaction using oxygen within eukaryotic cells. GFP expression of ACC spherical colonies gradually diminished from peripheral located cells after 7 days when colonies were cultured without passage. ACCs contained at day 10 contained GFP expressing central cells and non-GFP differentiated peripheral cells (data not shown). Mitochondrial morphology was evaluated in ACCs and differentiated cells by staining with a mitochondrial-specific dye, MitoTracker Red. ACC mitochondria were observed as peri-nuclear clusters that appear punctate and globular while differentiated cell contained many mitochondria which were filamentous and widespread in cytoplasm. ATP production of ACCs was less than that in native CD45 positive cells (FIG. 3B). Also, reactive oxygen species (ROS) production of ACCs was less than in native CD45 positive cells (FIG. 3C). Finally the key factors involved in mtDNA replication were assessed; which are mitochondrial transcription factor A (Tfam), the mitochondrial-specific DNA polymerase gamma (Polg) and its accessory unit (Polg2). The gene expression of Tfam, Polg, and Polg2 in ACCs was lower than those in differentiated cells (FIG. 3D). Consequently, ACCs contained small numbers of mitochondria and ACCs' mitochondrial activity was lower than differentiated cells. These results implied that ACCs acquired a metabolic system distinct from differentiated cells to survive after the severe stress response.

Developmental potential of ACCs. Finally, it was assessed whether ACCs possessed a developmental potential similar to that of plant callus cells. As an initial test for developmental potency, ACCs implanted subcutaneously in immunodeficient (SCID) mice were studied. Six weeks after transplantation, ACCs generated tissues representing all three germ layers (data not shown).

Figure 4A:
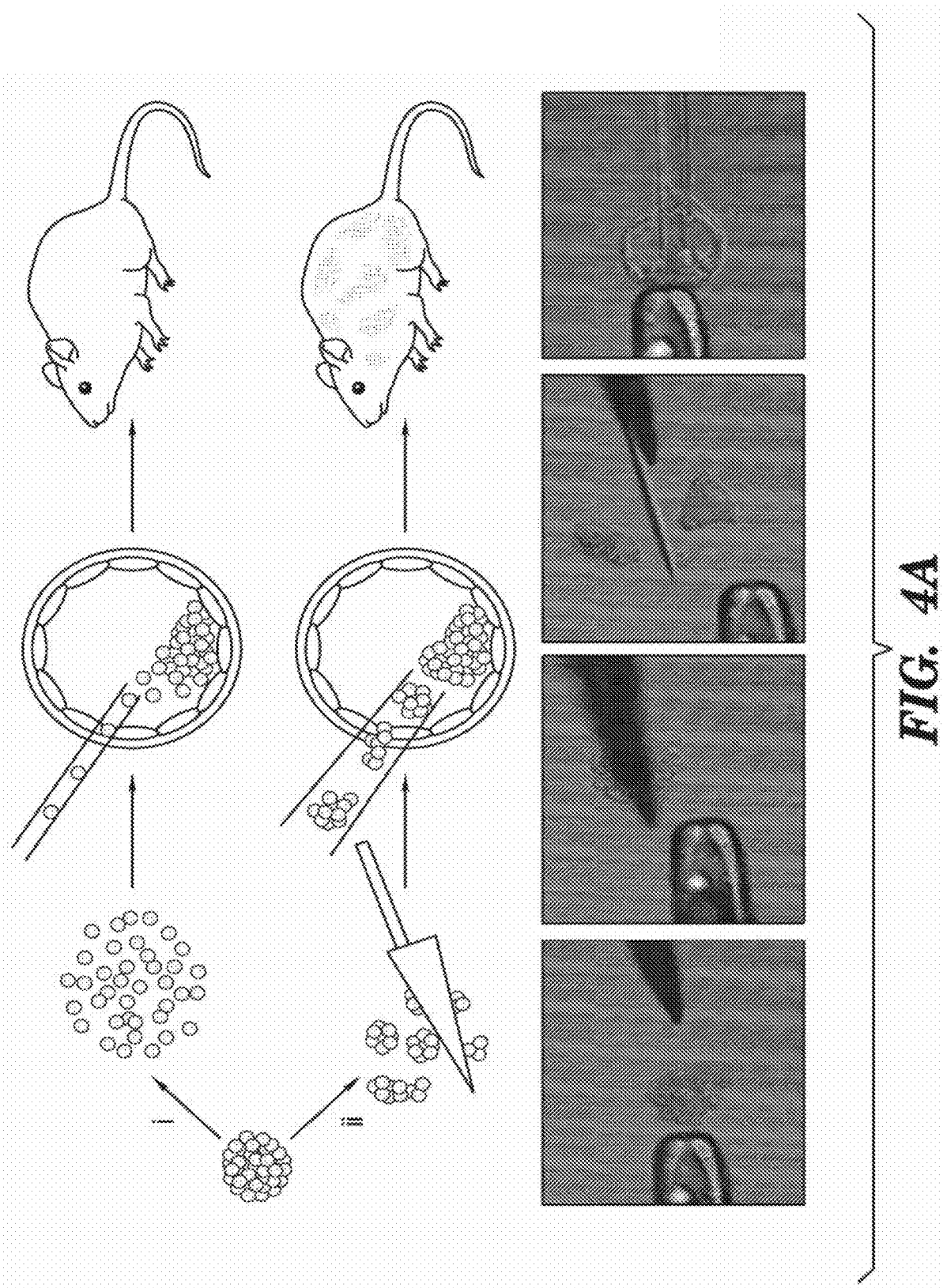
FIGS. 4A-4B depict chimera mouse generation from ACCs.
Figure 4B:
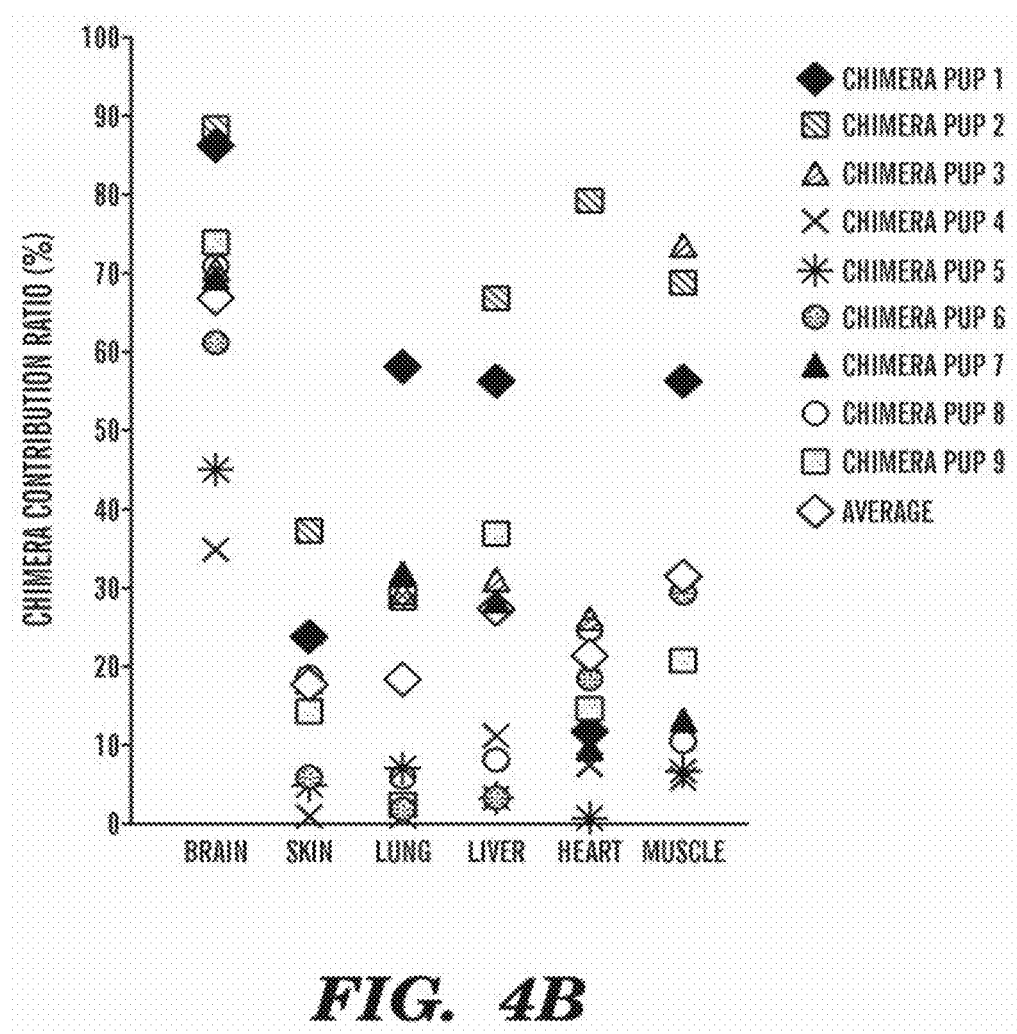

ACCs differentiated into cells representative of all three germ layers in vivo and in vitro. Therefore, the chimera contribution potency of ACCs was assessed. ACCs for use in chimera generation studies were prepared using CD45 positive cells derived from F1 GFP (C57BL/6GFP×DBA/2 or 129/SvGFP×C57BL/6GFP) or GOF. Because gene expression analysis had revealed that at day 7, ACCs expressed the highest level of pluripotent marker genes, day 7 ACCs were utilized for the chimera mouse generation study. Initially, conventional methods for chimera generation were utilized. ACs were dissociated into single cells via treatment with trypsin. The ACCs were then injected into blastocysts (FIG. 4A). Using this approach, the chimera contribution of dissociated ACCs was quite low (Table 1). Therefore ACCs without prior trypsin treatment, which often causes cellular damage 15, were injected into blastocysts. ACs were cut into small clusters using a micro-knife under the microscopy. Small clusters of ACs were then injected into blastocysts (FIG. 4A). Using this approach, the chimera contribution of ACCs dramatically increased (data not shown). Chimera mice generated with ACCs grew up healthy (data not shown) and germ line transmission has been observed. The chimera contribution rate of each tissue was analyzed by FACS. The results showed that ACCs derived from lymphocytes contributed to all tissue (FIG. 4B).

Figure 9:
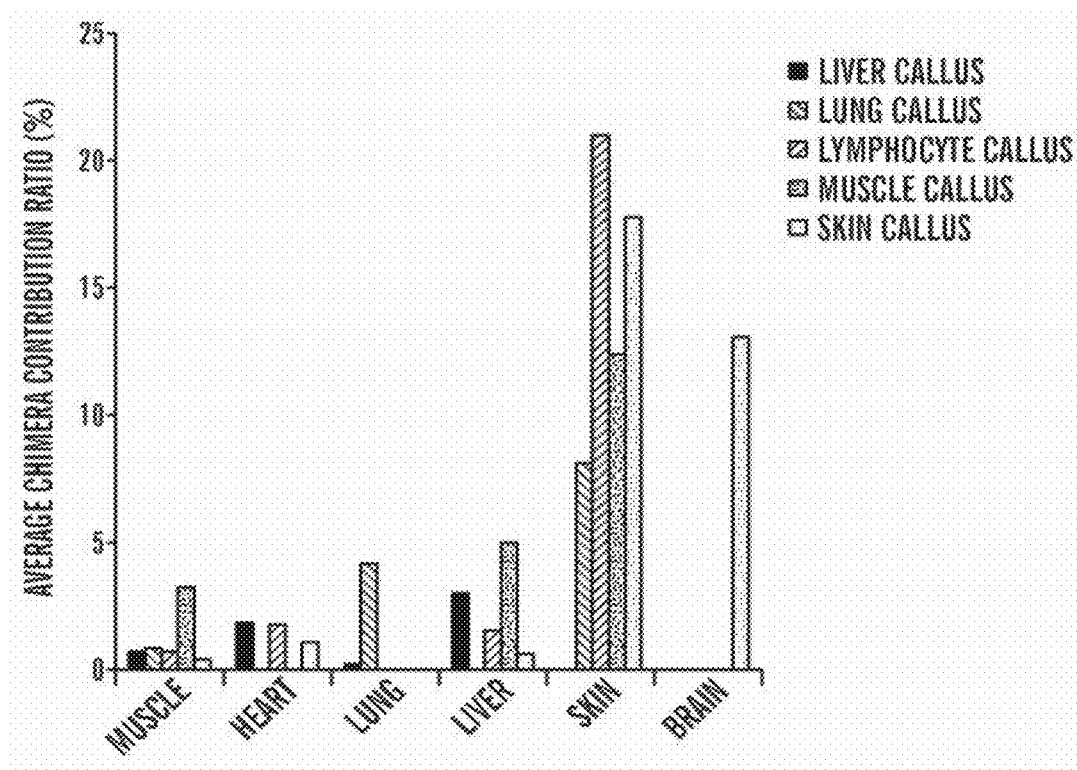
FIG. 9 depicts differentiation of ACCs. The graph depicts a chimera contribution analysis. Chimera fetuses generated with ACCs derived from various somatic cells were analyzed by FACS. Graph shows the average of 5 chimera fetuses at E13.5 to 15.5.
Figure 10:
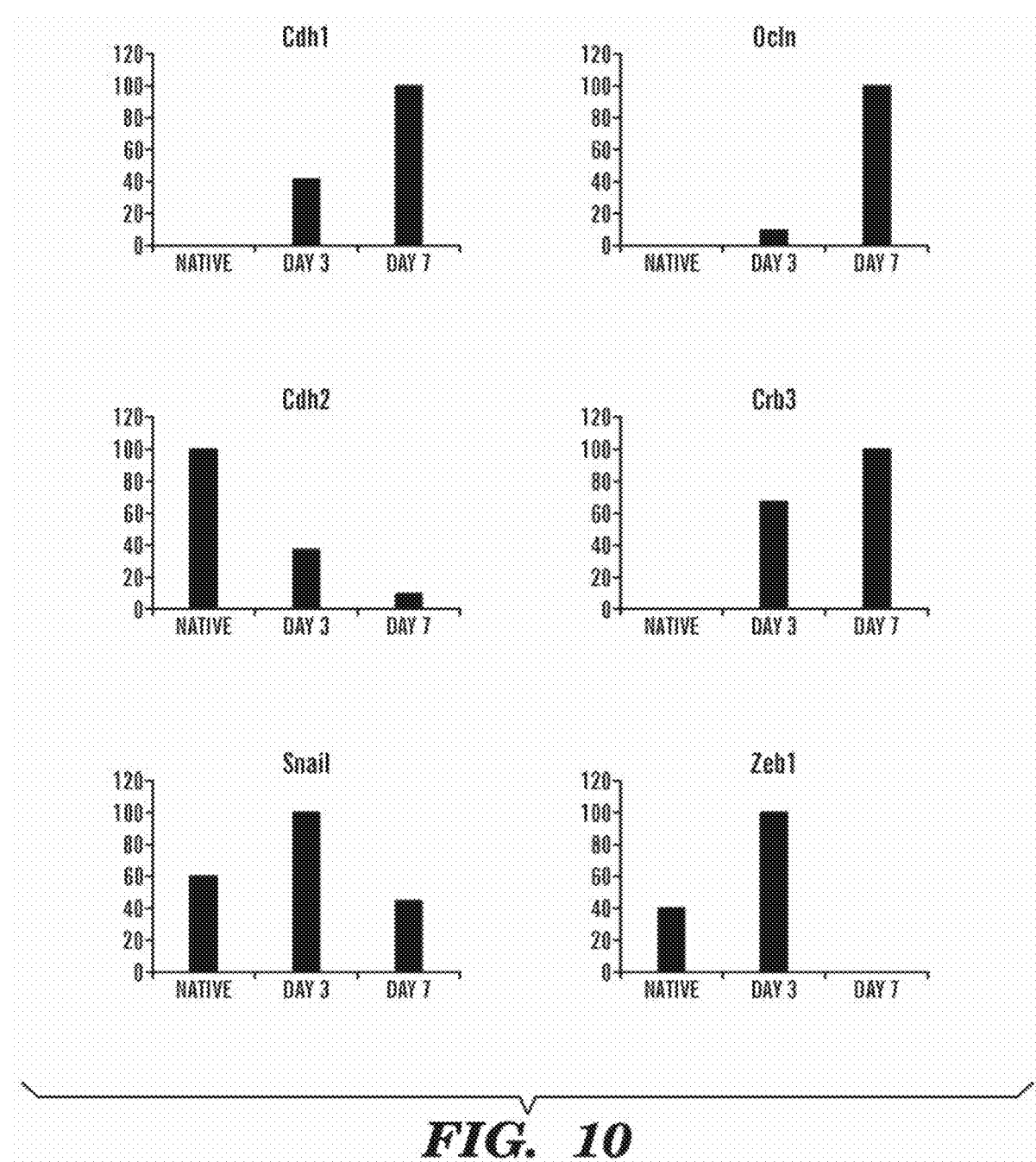
FIG. 10 demonstrates that stress treatment caused reprogramming to somatic cells via Mesenchymal-Epithelial Transition (MET). The expression of MET-related genes is shown in native cells, and in cells 3 and 7 days after stress treatment was begun. The y-axis shows % expression, normalized to the level in the sample with the expression level for that gene.
Figure 11:
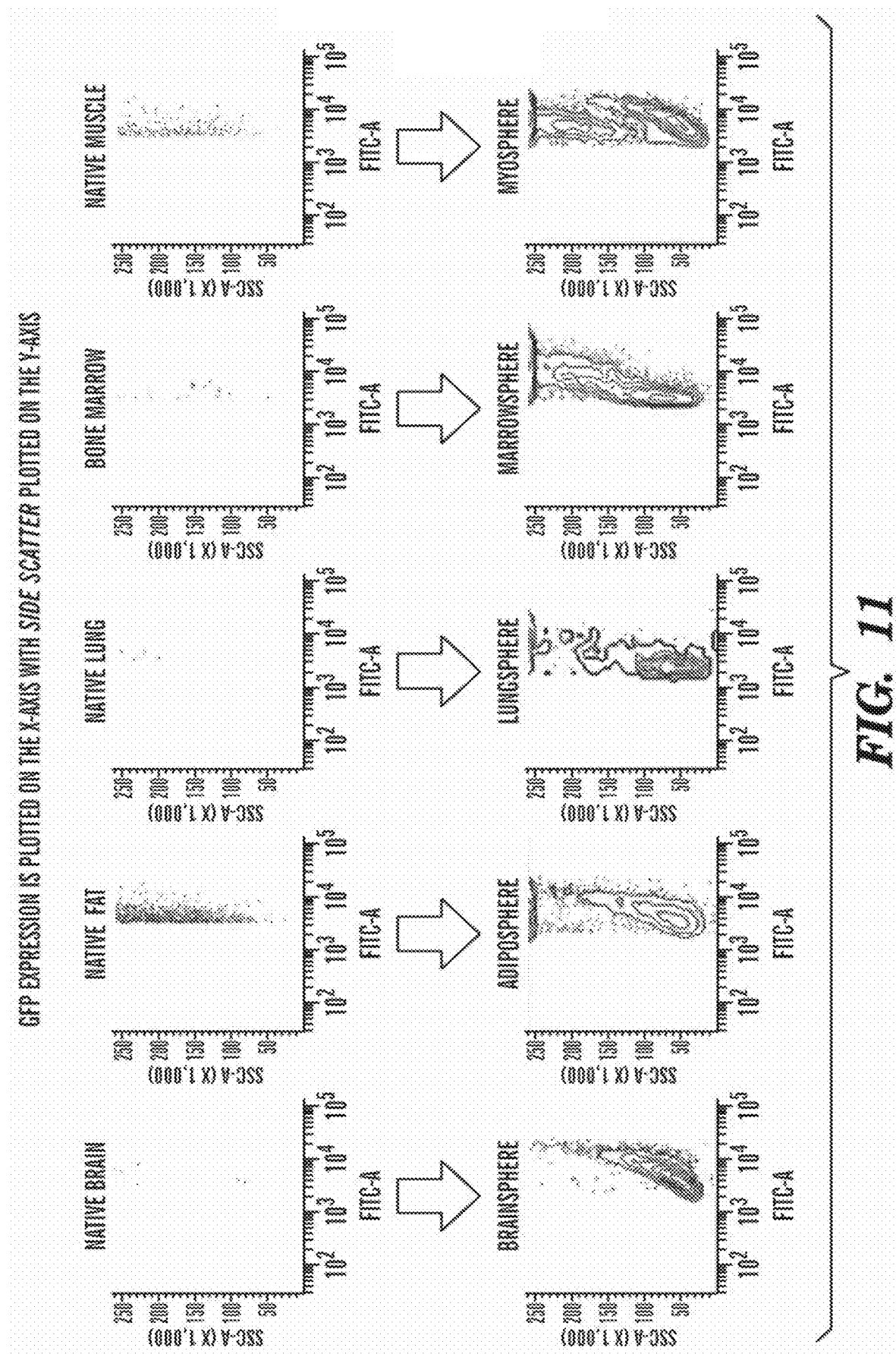
FIG. 11 depicts FACS analysis of cell populations before and after stress. GFP expression was evident, indicating generation of pluripotent cells, in post-stressed cell populations from each tested tissue type.

As demonstrated above, ACCs can be generated from various cells derived from all three germ layers (FIG. 7A-7B). In order to examine whether ACCs derived from various tissues had different differentiation tendencies, ACCs were generated from various tissues derived from F1GFP mice, and injected into ICR blastocysts. Then, using FACS, the contribution ratio of each tissue in the generated chimera mice was analyzed. It was found that ACCs derived from any tissue contributed to chimeric mouse generation (FIG. 9). In addition, the contribution ratio to skin, brain, muscle, fat, liver and lung was analyzed in chimera mice generated using ACCs derived from various tissues. ACCs derived from any tissue contributed to generate tissues representative of all three germ layers, and no differentiation tendency was observed (FIG. 9).

The generation of mice by tetraploid complementation, which involves injection of pluripotent cells in 4N host blastocysts, represents the most rigorous test for developmental potency because the resulting embryos are derived only from injected donor cells 16 ACCs were generated from lymphocytes derived from DBA×B6GFP F1 mice or 129/SvGFP×B6GFP F1. ACCs resulted in the generation of (mid) late-gastration 'all ACC embryos' after injection into 4N blastocysts (data not shown). Genotyping analysis demonstrated that 'all ACC embryos' had specific genes of strain which was utilized to generate ACCs. Thus, ACCs possessed the potential to generate a clonal body just like plant callus cells.

Discussion

Mammalian somatic cells exhibit the ability for animal callus (AC) formation as a result of exposure to significant external stimuli, in a fashion very similar to plants. The cells contained in these calli (animal callus cells, ACCs) have the ability to generate chimeric mice and to generate new embryos fully consisting of only cells generated from ACCs. The results described herein demonstrate that mammalian somatic cells regain the ability to differentiate into any of the three germ layers by external stimuli. This implies that somatic cells have a greater plasticity than previously believed. Furthermore, this study demonstrates the potential of somatic cell reprogramming without gene induction or the introduction of foreign proteins, and offers new insight into the potential of adult stem cells; representing a significant milestone in the elucidation of stem cell biology.

Materials and Methods

Tissue harvesting and Cell culture. For mature lymphocytes isolation, spleens derived from GOF mice or ICR mice were minced by scissors and mechanically-dissociated with pasture pipettes. Dissociated spleens were strain through a cell strainer (BD Biosciences, San Jose). Collected cells were re-suspended in DMEM medium and added the same volume of lympholyte (CEDARLANE®, Ontario, Canada), then centrifuged at 1000 g for 15 min. Lymphocytes layer was taken out and attained with CD45 antibody (ab25603, abcam, Cambridge, MA). CD45 positive cells were sorted by FACS Aria (BD Biosciences). Then, CD45 positive cells were treated with stress treatment (pH5.5 solution for 15 min) and plated into B27 medium supplemented with 1000 U LIF (Sigma) and 10 ng/ml FGF 2 (Sigma).

Exposure to external stimuli—stress treatment. To give a mechanical stress to mature cells, pasture pipette were heated and then stretched to create lumens approximately 50 microns in diameters, and then broken. Mature somatic cells were then triturated through these pipettes for 20 min, and cultured for 7 days. To provide a hypoxic stimulus to mature cells, cells were cultured in a 5% oxygen incubator for 3 weeks. An under nutrition stimulus was provided to mature cells, by culturing the cells in a basic culture medium for 3 weeks. To expose the mature cells to a physiological stress, they were treated with low pH (pH5.5) solution, and cultured for 7 days. Also, cells were given more serious damage. To create pores in mature cell membranes, cells were treated with SLO (Streptolysin 0).

SLO-treated cells were incubated in HBSS containing 10 µg/mL SLO at 37° C. for 50 mM and then cultured in culture medium without SLO for 7 days. Cells exposed to undernutrition stress were cultured in basal medium for 2 to 3 weeks. Cells exposed to "ATP" stress were incubated in HBSS containing 2.4 mM ATP at 37° C. for 15 mM and then cultured in culture medium for 7 days. Cells exposed to "Ca" stress were cultured in culture medium containing 2 mM $CaCl_2$ for 2 weeks.

Bisulfite sequence. For cells procured from GOF mice were dissociated into single cells. GFP positive cells collected using by FACS Aria. Genome DNA was extracted from ACCs and studied. Bisulfite treatment of DNA was done using the CpGenome DNA Modification Kit (Chemicon, Temecula, CA, http://www.chemicon.com) following the manufacturer's instructions. The resulting modified DNA was amplified by nested polymerase chain reaction PCR using two forward (F) primers and one reverse (R) primer: Oct4 (F1, GTTGTTTTGTTTTGGTTTTGGATAT (SEQ ID NO: 1; F2, ATGGGTTGAAATATTGGGTTTAT-TTA (SEQ ID NO: 2); R,CCACCCTCTAACCT-TAACCTCTAAC (SEQ ID NO: 3)). And Nanog (F1, GAG-GATGTTTTTTAAGTTTTTTTT (SEQ ID NO:4); F2, AATGTTTATGGTGGATTTTGTAGGT (SEQ ID NO: 5); R, CCCACACTCTATATCAATATAATAAC (SEQ ID NO:6)). PCR was done using TaKaRa Ex Taq Hot Start Version (RR030A). DNA sequencing was performed using M13 primer with the assistance of GRAS (The Genome Resource and Analysis Unit).

Immunohistochemistry. Cultured cells were fixed with 4% parafolmaldehyde and permeabilized with 0.1% Triton X-100/PBS prior blocking with 1% BSA solution (Life Technology, Tokyo, Japan). Secondary antibodies were goat anti-mouse or -rabbit coupled to Alexa-488 or -594 (Invitrogen). Cell nuclei were visualized with DAPI (Sigma). Slides were mounted with SlowFade Gold antifade reagent (Invitrogen).

Fluorescence-Activated Cell Sorting and Flow Cytometry. Cells were prepared according to standard protocols and suspended in 0.1% BSA/PBS on ice prior to FACS. PI (BD Biosciences) was used to exclude dead cells. Cells were sorted on a BD FACSAria SORP and analyzed on a BD LSRII with BD FACSDiva Software (BD Biosciences).

RNA Preparation and RT-PCR Analysis. RNA was isolated with the RNeasy Micro kit (QIAGEN). Reverse transcription was performed with the SupeSACript III First Strand Synthesis kit (Invitrogen). SYBR Green Mix I (Roche Diagnostics) was used for amplification, and samples were run on a Lightcycler-II Instrument (Roche Diagnostics).

Animal Studies. For tumorigenicity studies, cells suspended in 100 ml PBS were injected subcutaneously in the flanks of age-matched immunodeficient SCID mice. Mice were sacrificed and necropsied after 6 weeks.

ATP and ROS Assay. Intercellular ATP level was measured by the ATP Bioluminescence Assay Kit HS II (Roche) according to supplier's protocol. The luminescence intensity was measured by using a Gelomax 96 Microplate Luminometer (Promega, Madison, WI) and the luminescence readings were normalized by cell count. For measurement of ROS levels, cells were incubated in a medium contain 2 μM dihydroethidium (Molecular Probes) at 37° C. in dark for 15 minutes. Cells were then washed with PBS and suspended in PBS containing 0.5% BSA. The fluorescence intensity of 30000 cells was recorded with the help of a BD Biosciences LSR II (BD Bioscience, Spark, MD).

Chimera mice generation and analyses. Production of Diploid and Tetraploid Chimeras. Diploid embryos were obtained from ICR strain females mated with ICR males and tetraploid embryos were obtained from BDF1 strain females mated with BDF1 males. Tetraploid embryos were produced by the electrofusion of 2-cell embryos[17]. In this study, because trypsin treatment caused low chimerism, ACCs spherical colonies were cut into small pieces using a microknife under the microscopy, then small clusters of ACCs were injected into day 4.5 blastocyst by large pipette. Next day, the chimeric blastocysts were transferred into day 2.5 pseudopregnant females.

REFERENCES

1. Brockes, J. P. & Kumar, A. Plasticity and reprogramming of differentiated cells in amphibian regeneration. Nature reviews. Molecular cell biology 3, 566-574, doi:10.1038/nrm881 (2002).
2. Sinnott, J. J. & Burklund, C. W. The treatment of carotid insufficiency. The Nebraska state medical journal 45, 357-359 (1960).
3. Hanna, J. et al. Direct reprogramming of terminally differentiated mature B lymphocytes to pluripotency. Cell 133, 250-264, doi:10.1016/j.cell.2008.03.028 (2008).
4. Hockemeyer, D. et al. A drug-inducible system for direct reprogramming of human somatic cells to pluripotency. Cell stem cell 3, 346-353, doi:10.1016/j.stem.2008.08.014 (2008).
5. Kim, D. et al. Generation of human induced pluripotent stem cells by direct delivery of reprogramming proteins. Cell stem cell 4, 472-476, doi:10.1016/j.stem.2009.05.005 (2009).
6. Kim, J. B. et al. Direct reprogramming of human neural stem cells by OCT4. Nature 461, 649-643, doi:10.1038/nature08436 (2009).
7. Okabe, M. et al. Definitive proof for direct reprogramming of hematopoietic cells to pluripotency. Blood 114, 1764-1767, doi:10.1182/blood-2009-02-203695 (2009).
8. Ohbo, K. et al. Identification and characterization of stem cells in prepubertal spermatogenesis in mice small star, filled. Developmental biology 258, 209-225 (2003).
9. Ying, Q. L. et al. The ground state of embryonic stem cell self-renewal. Nature 453, 519-523, doi:10.1038/nature06968 (2008).
10. Ogawa, K., Matsui, H., Ohtsuka, S. & Niwa, H. A novel mechanism for regulating clonal propagation of mouse ES cells. Genes to cells: devoted to molecular & cellular mechanisms 9, 471-477, doi:10.1111/j.1356-9597.2004.00736.x (2004).
11. Gough, N. M. et al. LIF: a molecule with divergent actions on myeloid leukaemic cells and embryonic stem cells. Reproduction, fertility, and development 1, 281-288 (1989).
12. Hitoshi, S. et al. Primitive neural stem cells from the mammalian epiblast differentiate to definitive neural stem cells under the control of Notch signaling. Genes & development 18, 1806-1811, doi:10.1101/gad.1208404 (2004).
13. Tesar, P. J. et al. New cell lines from mouse epiblast share defining features with human embryonic stem cells. Nature 448, 196-199, doi:10.1038/nature05972 (2007).
14. Saretzki, G., Armstrong, L., Leake, A., *Lako*, M. & von Zglinicki, T. Stress defense in murine embryonic stem cells is superior to that of various differentiated murine cells. Stem Cells 22, 962-971, doi:10.1634/stemcells.22-6-962 (2004).
15. Mitalipova, M. M. et al. Preserving the genetic integrity of human embryonic stem cells. Nature biotechnology 23, 19-20, doi:10.1038/nbt0105-19 (2005).
16. Nagy, A., Rossant, J., Nagy, R., Abramow-Newerly, W. & Roder, J. C. Derivation of completely cell culture-derived mice from early-passage embryonic stem cells. Proceedings of the National Academy of Sciences of the United States of America 90, 8424-8428 (1993).
17. Nagy, A. et al. Embryonic stem cells alone are able to support fetal development in the mouse. Development 110, 815-821 (1990).

TABLE 1

Generation of chimera mice from ACCs

| Mouse strain | Cell preparation for injection | Culture period of SACs | No. of fertilized embryos injected | No. offspring | No. of chimeric mice obtained Total | High contribution** |
|---|---|---|---|---|---|---|
| BDF1 | Single | 7 day | 40 | 32 | 1 | 0 |
| BDF1 | Cluster | 7 day | 58 | 48* | 16 | 4 |
| 129B6F1 | Cluster | 7 day | 98 | 64 | 20 | 6 |
| GOF | Cluster | 7 day | 73 | 35 | 24 | 2 |
| GOF | Cluster | 10 day | 35 | 20 | 4 | 0 |

*All fetuses were collected at 13.5 dpc to 15.5 dpc and the contribution rate of ACCs into each organs was examined by FACS
**The contribution of SACs into each chimera was scored as high (>50% of the coat color of GFP expression)

TABLE 2

Primer Sequences.
The middle column contains, from top to bottom, SEQ ID NOs: 7-39 and the right hand column contains, from top to bottom, SEQ ID NOs: 40-72.

| Gene | 5' Primer | 3' Primer |
|---|---|---|
| Txni | gtcatccttgatctgcccct | gagacgacctgctacacctg |
| Bmi1 | ggtacttacgatgcccagca | tccctacctgactgcttacg |
| Prdx2 | ccctgaatatccctctgct | tatgtctgctcgtacccctt |
| Hspb1 | agatggctacatctctcggt | tcagacctcggttcatcttc |
| Hif3a | cactctggacttggagatgc | cttgaccttcgaaggacga |
| Hspa1b | cttgtcgttggtgatggtga | tcaaagcgcagaccacctcg |
| Hspa9a | gttgaagcagttaatatggc | gcatgtcgtccgcagtaact |
| Ercc4 | agatgagaccaacctggacc | tcgacttcgtcttgttcggt |
| Hpas1a | aggtggagatcatcgccaac | tctacctgttccgcgtctag |
| Gapdh | cgttgaatttgccgtgagtg | tggtgaaggtcggtgtgaac |
| Gpx2 | attgccaagtcgttctacga | gtaggacagaaacggatgga |
| Sod2 | aggtcgcttacagattgct | gtgtcgatcgttcttcact |
| Tgr | gtctctttagaaaagtgtga | attgcagctgcaaatccctg |
| Gsta | tacagctttcttcctggcca | tacgattcacggaccgtgcc |
| Pdha2 | atgtcagccttgtggaaatt | aacgataactgatccctggg |
| Gpx3 | gtctgacagaccaataccat | cagttctacctgtaggacag |
| Gpx4 | aacggctgcgtggtgaagcg | cctccttccaggtctccgga |
| Polg | ggacctcccttagagaggga | agcatgccagccagagtcact |
| Pol2 | acagtgccttcaggttagtc | actccaatctgagcaagacc |
| Tfam | gcatacaaagaagctgtgag | gttatatgctgaacgaggtc |
| Oct4 | tctttccaccaggcccccggct | tgcgggcggacatggggagatcc |
| Ecat1 | tgtggggccctgaaaggcgagctgagat | atgggccgccatacgacgacgctcaact |
| Esg1 | gaagtctggttccttggcaggatg | actcgatacactggcctagc |
| Nanog | caggtgtttgagggtagctc | cggttcatcatggtacagtc |
| ERas | actgccctcatcagactgctact | cactgccttgtactcgggtagctg |
| Gdf3 | gttccaacctgtgcctcgcgtctt | agcgaggcatggagagagcggagcag |

TABLE 2-continued

Primer Sequences.
The middle column contains, from top to bottom, SEQ ID NOs: 7-39 and the right hand column contains, from top to bottom, SEQ ID NOs: 40-72.

| Gene | 5' Primer | 3' Primer |
|---|---|---|
| Fgf4 | cgtggtgagcatcttcggagtgg | ccttcttggtccgcccgttctta |
| Rex1 | acgagtggcagtttcttcttggga | tatgactcacttccaggggggcact |
| Cripto | atggacgcaactgtgaacatgatgttcgca | ctttgaggtcctggtccatcacgtgaccat |
| Dax1 | tgctgcggtccaggccatcaagag | gggcactgttcagttcagcggatc |
| Sox2 | tagagctagactccgggcgatga | ttgccttaaacaagaccacgaaa |
| Klf4 | gcgaactcacacaggcgagaaacc | tcgcttcctcttcctccgacaca |
| Fgf5 | gctgtgtctcagggggattgt | cactctcggcctgtcttttc |

TABLE 3

Percent of cells demonstrating pluripotent phenotype after 1 week of stress treatment. Treatments are shown in the first column and the tissue of origin of the somatic cells is shown in the second row. Numbers are percentages.

| | 1 week-old | | | | | |
|---|---|---|---|---|---|---|
| | Bone Marrow | Brain | Lung | Muscle | Fat | Fibroblast |
| Control | 0 | 0 | 0 | 0 | 0 | 0 |
| Hypoxia | 2 | 3 | 3.2 | 2.8 | 1.6 | 1.2 |
| Trituration | 19.5 | 20.5 | 19.8 | 20.6 | 18.4 | 9.5 |
| SLO | 13.2 | 10.3 | 18.4 | 20.5 | 32.8 | 15.2 |
| undernutrition | 2 | 3.4 | 1.8 | 4.5 | 2.4 | 1.5 |
| ATP | 12.3 | 15.4 | 9.8 | 68.4 | 79.6 | 25.10 |
| Ca | 1.2 | 0.8 | 1.3 | 1.5 | 2.7 | 3.5 |

Example 2

Without wishing to be bound by theory, the methods described herein are contemplated to be activating a process related to apoptosis, or controlled cell death. Mild injury to cells can induce the activation of repair genes. Severe injury to cells can activate a previously undefined survival mechanism. It is contemplated that when cells are exposed to a significant stress, such as the stresses described herein, the cellular components (e.g. mitochondria, vesicles, nuclei, ribosomes, endoplasmic reticulum, exosomes, endosomes, cell membranes, mitochondria, lysosomes, ATP, proteins, enzymes, carbohydrates, lipids, etc) are released from the damaged cells into a "cellieu." Data described herein indicate that this "cellieu" can be capable of reconstituting and/or promoting the survival of cells. It is additionally contemplated, without wishing to be bound by theory, that mitochondria (and other organelles) are able to direct the reconstitution of the cells. Because of the small size, simplicity, ability to direct cell differentiation, and prokaryotic-like nature, mitochondria may survive stresses that prove lethal to the parent cell. Mitochondria can be released from the cell free, encapsulated in a membrane, and/or bound to other cellular components.

Alternatively, without wishing to be bound by theory, the nuclei can remain intact, encapsulated in a cell membrane which can comprise some mitochondria. These damaged cells with very little cytoplasm and very few organelles, which have lost the epigenetic control of the nucleus, can then interact and possibly fuse with organelles that have been extruded. This provides cells with the subcellular components necessary for growth and replication but the cells have lost epigenetic control, and therefore a more primitive (e.g. more pluripotent) state is induced.

What is claimed herein is:

1. A method for increasing the number of cells expressing one or more markers of pluripotency in a population comprising non-embryonic normal differentiated mammalian somatic cells not expressing markers of pluripotency comprising,
   without introduction of an exogenous gene, a transcript, a protein, a nuclear component or cytoplasm, or without cell fusion,
   subjecting the population of non-embryonic normal differentiated mammalian somatic cells to an effective amount of stress comprising between about 200 micromolar and about 200 millimolar adenosine triphosphate (ATP) at a pH between 4.5 and 6.8 to increase the levels of stress induced genes to increase the number of cells expressing one or more markers of pluripotency selected from the group consisting of Oct4, Nanog, E-cadherin, and SSEA in the population without lysing all of the cells, and
   screening for cells expressing the one or more markers of pluripotency in the population,
   wherein the cells are capable of proliferating.

2. The method of claim 1, further comprising selecting the cells expressing one or more markers of pluripotency.

3. The method of claim 2, wherein the marker is Oct4.

4. The method of claim 1, wherein the cell population is exposed to temperatures between freezing and below 35° C. or above 42° C. up to about 85° C.

5. The method of claim 1, wherein the membranes of the cells in the cell population are mechanically disrupted.

6. The method of claim 1, wherein the cell population is exposed to mechanical stress disrupting pores resulting in loss of between 50 and 90% of the cytoplasm or the mitochondria from the cell.

7. The method of claim 1 wherein the cell population is exposed to the stress for a period between about 1 min and about 1 hour.

8. The method of claim 4 wherein the temperatures are at or below freezing.

9. The method of claim 1 wherein the application of inducers of cell reprogramming of chromatin through epigenetic changes including demethylation and methylation of DNA and histones.

10. The method of claim 1 wherein the concentration of ATP is between about 2.4 millimolar and about 200 millimolar.

11. The method of claim 1, further comprising subjecting the population of non-embryonic differentiated somatic cells to oxygen deprivation.

12. The method of claim 11, wherein the cell population is exposed to the stress for a period between about 1 minute and three weeks.

* * * * *